(12) United States Patent
Boons et al.

(10) Patent No.: US 9,938,312 B2
(45) Date of Patent: Apr. 10, 2018

(54) COMPOUNDS AND METHODS FOR CHEMICAL AND CHEMO-ENZYMATIC SYNTHESIS OF COMPLEX GLYCANS

(75) Inventors: Geert-Jan Boons, Athens, GA (US); Zhen Wang, Arlington, MA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 1197 days.

(21) Appl. No.: 14/005,036

(22) PCT Filed: Mar. 23, 2012

(86) PCT No.: PCT/US2012/030408
§ 371 (c)(1),
(2), (4) Date: Oct. 17, 2013

(87) PCT Pub. No.: WO2012/135049
PCT Pub. Date: Oct. 4, 2012

(65) Prior Publication Data
US 2014/0051603 A1    Feb. 20, 2014

Related U.S. Application Data

(60) Provisional application No. 61/467,661, filed on Mar. 25, 2011.

(51) Int. Cl.
*C07H 13/04* (2006.01)
*C07H 15/18* (2006.01)

(52) U.S. Cl.
CPC .............. *C07H 13/04* (2013.01); *C07H 15/18* (2013.01)

(58) Field of Classification Search
None
See application file for complete search history.

(56) References Cited

U.S. PATENT DOCUMENTS

| | | | |
|---|---|---|---|
| 7,820,797 B2 | 10/2010 | Boons | |
| 8,563,523 B2 | 10/2013 | Boons | |
| 8,980,311 B2 | 3/2015 | Ingale et al. | |
| 9,211,345 B2 | 12/2015 | Boons et al. | |
| 9,309,276 B2 | 4/2016 | Boons | |
| 9,446,144 B2 | 9/2016 | Boons et al. | |
| 2007/0281865 A1* | 12/2007 | Blixt | C07H 5/06 506/9 |
| 2009/0041836 A1 | 2/2009 | Boons et al. | |
| 2009/0196916 A1 | 8/2009 | Ingale et al. | |
| 2011/0280893 A9 | 11/2011 | Boons | |
| 2012/0039984 A1 | 2/2012 | Boons et al. | |
| 2012/0142560 A1 | 6/2012 | Boons et al. | |
| 2014/0011987 A1 | 1/2014 | Boons | |
| 2014/0051603 A1 | 2/2014 | Boons et al. | |
| 2014/0212473 A1 | 7/2014 | Boons et al. | |
| 2015/0087806 A1 | 3/2015 | Boons et al. | |
| 2016/0060365 A1 | 3/2016 | Boons et al. | |
| 2017/0008977 A1 | 1/2017 | Boons et al. | |

FOREIGN PATENT DOCUMENTS

| | | |
|---|---|---|
| WO | WO 2007/079448 A2 | 7/2007 |
| WO | WO 2007/146070 A2 | 12/2007 |
| WO | WO 2009/035528 A2 | 3/2009 |
| WO | WO 2009/035528 A3 | 3/2009 |
| WO | WO 2010/002478 A2 | 1/2010 |
| WO | WO 2010/117803 A2 | 10/2010 |
| WO | WO 2012/135049 A1 | 10/2012 |

OTHER PUBLICATIONS

International Patent Application No. PCT/US2012/030408, filed Mar. 23, 2012; International Search Report / Written Opinion dated Jul. 26, 2012; 7 pages.
International Patent Application No. PCT/US2012/030408, filed Mar. 23, 2012; International Preliminary Report on Patentability dated Oct. 1, 2013; 5 pages.
Agard et al., "A strain-promoted [3+2] azide-alkyne cycloaddition for covalent modification of biomolecules in living systems," 2004, *J. Am. Chem. Soc.*, 126:15046-47.
Alvarez, et al. "Identification of ligand specificities for glycan-binding proteins using glycan arrays," 2006, *Methods Enzymol.*, 415:292-310.
Anisfeld et al., "A Convergent Approach to the Chemical Synthesis of Asparagine-Linked Glycopeptides," 1990, *J. Org. Chem.*, 55:5560-62.
Ban, et al. "On-chip synthesis and label-free assays of oligosaccharide arrays," Mar. 26, 2008, *Angewandte Chemie International Edition*, 47(18):3396-99.
Bartolozzi et al., "New approaches to the chemical synthesis of bioactive oligosaccharides," Oct. 2001, *Curr. Opin. Struct. Biol.*, 11(5):587-92.
Bejugam et al., "An efficient synthetic route to glycoamino acid building blocks for glycopeptide synthesis," Oct. 28, 2004, *Org. Lett.*, 6(22):4001-04.
Belser et al., "Contemporary North American influenza H7 viruses possess human receptor specificity: Implications for virus transmissibility," May 27, 2008, *Proc. Nat. Acad. Sci. USA*, 105(21):7558-63.
Beltran-Valero de Bernabe et al., "Mutations in the O-mannosyltransferase gene POMT1 give rise to the severe neuronal migration disorder Walker-Warburg syndrome," Nov. 2002, *Am. J. Hum. Genet.*, 71(5):1033-43.
Bennett et al. "Chemoenzymatic approaches to glycoprotein synthesis," Aug. 2007, *Chem. Soc. Rev.*, 36(8):1227-38.
Bertozzi et al., "Chemical glycobiology," Mar. 23, 2001, *Science*, 291(5512):2357-64.
Blixt et al., "Printed covalent glycan array for ligand profiling of diverse glycan binding proteins" Proc Natl Acad Sci USA, Dec. 7, 2004; 101(49):17033-8. Epub Nov. 24, 2004.
Blixt et al., "Chemoenzymatic synthesis of glycan libraries" Methods Enzymol, 2006; 415:137-53.
Bohorov et al., "Arraying glycomics: a novel bi-functional spacer for one-step microscale derivatization of free reducing glycans" Glycobiology, Dec. 2006; 16(12):21C-27C.
Boltje et al., "Opportunities and challenges in synthetic oligosaccharide and glycoconjugate research," Nov. 2009, *Nature Chemistry*, 1(8): 611-622.

(Continued)

*Primary Examiner* — Christopher M Gross
(74) *Attorney, Agent, or Firm* — Mueting, Raasch & Gebhardt, P.A.

(57) ABSTRACT

The present invention provides chemical and chemo-enzymatic methods for the synthesis of a wide array of complex asymmetric multi-antennary glycans.

17 Claims, 4 Drawing Sheets

(56) References Cited

OTHER PUBLICATIONS

Boltje et al., "Chiral-auxiliary-mediated 1,2-cis-glycosylations for the solid-supported synthesis of a biologically important branched alpha-glucan," Jul. 2010, *Nature Chemistry*, 2(7): 552-57.
Boltje et al., "Versatile set of orthogonal protecting groups for the preparation of highly branched oligosaccharides" Org Lett, Oct. 15, 2010; 12(20):4636-9.
Boons, "Recent developments in chemical oligosaccharide synthesis," 1996, *Contemp. Org. Synth.*, 3:173-200.
Boons et al., "Recent advances in O-sialylation," Dec. 13, 2000, *Chem. Rev.* 100(12):4539-66.
Boons. "Novel Approaches for the Synthesis of Glycoprotein Standards". U.S. Department of Health & Human Services Grant 1R01GM090269-01. Abstract.
Boons, "Beyond Metal and Azide Mediated Click Reaction: Applications to Glycoscience" ACS Spring Meeting, Claude S. Hudson Award in Carbohydrate Chemistry Symposium at the 241st National Meeting & Exposition of the American Chemical Society, Anaheim, CA. Mar. 27, 2011. Title Pages and Presentation. 33 pages.
Boons, "Combinatorial Carbohydrate Synthesis for Glycomics" ACS Spring Meeting, Abstract No. 2, Claude S. Hudson Award in Carbohydrate Chemistry Symposium at the 241st National Meeting & Exposition of the American Chemical Society, Anaheim, CA. Mar. 27, 2011. [retrieved on Dec. 14, 2016]. Retrieved from the Internet:<URL: http://acselb-529643017.us-west2.elb.amazonaws.com/chem/241nm/program/view.php?obj_id=75950&terms=>; 1 pg.
Borman, "New Approach to Glycosylation: Technique could facilitate one-pot and automated syntheses of carbohydrates," Chem. Eng. News, Aug. 22, 2005; 83(34):11.
Breloy et al., "Initiation of mammalian O-mannosylation in vivo is independent of a consensus sequence and controlled by peptide regions within and upstream of the alpha-dystroglycan mucin domain," Jul. 4, 2008, *The Journal of Biological Chemistry*, 283 (27): 18832-40.
Brockhausen, "Mucin-type O-glycans in human colon and breast cancer: glycodynamics and functions," Jun. 2006, *EMBO Rep.*, 7(6):599-604.
Brown et al., "Glycan antagonists and inhibitors: a fount for drug discovery," 2007 *Crit. Rev. Biochem. Mol. Biol.*, 42(6):481-515.
Bucior et al., "Carbohydrate-carbohydrate interactions in cell recognition," Oct. 2004, *Curr. Op. Struct. Biol.*, 14(5):631-37.
Bulter et al., "Enzymatic synthesis of nucleotide sugars," Feb. 1999, *Glycoconj. J.*, 16(2):147-59.
Burton et al., "Preparation of fluorinated galactosyl nucleoside diphosphates to study the mechanism of the enzyme galactopyranose mutase," 1997, *J. Chem. Soc., Perkin Trans.*, 1:2375-82.
Buskas et al., "Synthesis of a dimeric Lewis antigen and the evaluation of the epitope specificity of antibodies elicited in mice," Sep. 5, 2005, *Chem. Eur. J.*, 11(8):5457-67.
Buskas et al., "The immunogenicity of the tumor-associated antigen Lewis(y) may be suppressed by a bifunctional cross-linker required for coupling to a carrier protein," 2004, *Chem. Eur. J.*, 10:3517-24.
Buskas et al., "Glycopeptides as versatile tools for glycobiology," Aug. 2006, *Glycobiology*, 16(8):113R-136R.
Carpino, "1-Hydroxy-7-azabenzotriazole—an efficient peptide coupling additive," 1993, *J. Am. Chem. Soc.*, 115:4397-98.
Cato et al., "Highly efficient stereospecific preparation of Tn and TF building blocks using thioglycosyl donors and the Ph2SO/Tf20 promotor system," 2005, *J. Carbohydr. Chem.*, 24:503-16.
Chai et al., "High prevalence of 2-mono- and 2,6-di-substituted manol-terminating sequences among O-glycans released from brain glycopeptides by reductive alkaline hydrolysis," Aug. 1999, *Eur. J. Biochem.*, 263(3):879-88.
Chandrasekaran et al., "Glycan topology determines human adaptation of avian H5N1 virus hemagglutinin," Jan. 2008, *Nat. Biotechnol.*, 26(1):107-13.
Chen et al., "In vitro evolution of H5N1 avian influenza virus toward human-type receptor specificity" Virology, Jan. 5, 2012; 422(1):105-13. Epub Nov. 5, 2011.
Chiba et al., "Structures of sialylated O-linked oligosaccharides of bovine peripheral nerve alpha-dystroglycan. The role of a novel O-mannosyl-type oligosaccharide in the binding of alpha-dystroglycan with laminin," Jan. 24, 1997, *The Journal of Biological Chemistry*, 272(4):2156-62.
Chu et al., "A high sensitive fiber SERS probe based on silver nanorod arrays," Sep. 17, 2007, *Optics Express*, 15(19):12230-39.
Codee et al., "Efficient installation of beta-mannosides using a dehydrative coupling strategy," Jul. 21, 2005, *Org. Lett.*, 7(15):3251-54.
Cohen-Anisfeld et al., "A practical, convergent method for glycopeptide synthesis," 1993, *J Am. Chem. Soc.*, 115:10531-37.
Crich et al., "Are glycosyl triflates intermediates in the sulfoxide glycosylation method? A chemical and H-1; C-13, and F-19 NMR spectroscopic investigation," 1997, *J. Am. Chem. Soc.*, 119:11217-23.
Crich et al., "Direct stereoselective synthesis of beta-thiomannoside," Feb. 11, 2000, *J. Org. Chem.*, 65(3):801-05.
Crich et al., "1-Benzenesulfinyl piperidine/trifluoromethanesulfonic anhydride: a potent combination of shelf-stable reagents for the low-temperature conversion of thioglycosides to glycosyl triflates and for the formation of diverse glycosidic linkages" J Am Chem Soc, Sep. 19, 2001; 123(37):9015-20.
Dan et al., "Stereocontrolled synthesis of the pentasaccharide core structure of asparagine-linked glycoprotein oligosaccharide based on a highly convergent strategy," 1995, *Tetrahedron Lett.*, 36:7487-90.
Danishefsky et al., "Glycals in organic synthesis: the evolution of comprehensive strategies for the assembly of oligosaccharides and glycoconjugates of biological Consequence," 1996, *Angew. Chem. Int. Ed.* 35:1380-1419.
Davis, "Recent developments in oligosaccharide synthesis," 2000, *J. Chem. Soc., Perkin Trans.* 1:2137-60.
Davis. "Synthesis of glycoproteins," Feb. 2002, *Chem. Rev.*, 102(2):579-601.
Demchenko. "Stereoselective chemical 1,2-cis O-glycosylation: from 'sugar ray' to modern techniques of the $21^{st}$ century," 2003, *Synlett*, 1225-40.
Demchenko et al., "Synthesis and biological evaluation of *Rhizobium sin-1* lipid A derivatives," May 21, 2003, *J. Am. Chem. Soc.*, 125(2):6103-12.
De Paz, et al. "Oligosaccharide microarrays to map interactions of carbohydrates in biological systems," 2006, *Methods Enzymol.*, 415:269-92.
Ellervik et al., "Glycosylation with N-Troc-protected glycosyl donors," Jan. 11, 1996, *Carbohydr. Res.* 280(2):251-60.
Ellgaard et al., "Quality control in the endoplasmic reticulum," Mar. 2003, *Nat. Rev. Mol. Cell Biol.*, 4(3): 181-91.
Feizi et al. "Carbohydrate microarrays—a new set of technologies at the frontiers of glycomics," Oct. 2003, *Curr. Opin. Struct. Biol.*, 13(5):637-45.
Flitsch, "Synthetic Chemistry: Glycosylation with a Twist," Sep. 8, 2005, *Nature*, 437(7056):201-02.
Gabius et al., "From lectin structure to functional glycomics: principles of the sugar code" Trends Biochem Sci, Jun. 2011; 36(6):298-313.
Galan et al., "Glycosyltransferase activity can be selectively modulated by chemical modifications of acceptor substrates," 2004, *Bioorg. Med. Chem. Lett.* 14:2205-08.
Gamblin et al., "Glycoprotein synthesis: an update," Jan. 2009, *Chem. Rev.*, 109(1):131-63.
Garcia et al., "Evaluation and comparison of various PCR methods for detection of Mycoplasma gallisepticum infection in chickens," Mar. 2005, *Avian Dis.*, 49(1):125-32.
Gaunt et al., "Rational design of benzyl-type protecting groups allows sequential deprotection of hydroxyl groups by catalytic hydrogenolysis," 1998, *J. Org. Chem.*, 63:4172-73.
Gijsen et al., "Recent Advances in the Chemoenzymatic Synthesis of Carbohydrates and Carbohydrate Mimetics," Feb. 1, 1996, *Chem. Rev.* 96(1):443-74.

(56) References Cited

OTHER PUBLICATIONS

Gold et al., "Synthesis of Sugar Nucleotides by Application of Phosphoramidites," Dec. 5, 2008, *J. Org. Chem.* 73(23):9458-60.

Gridley et al., "Recent advances in the construction of beta-D-mannose and beta-D-mannosamine linkages," 2000, *J. Chem. Soc., Perkin Trans.*, 1:1471-91.

Guo, et al., "Chemical synthesis of GPis and GPI-anchored glycopeptides," 2004, *Eur. J. Org. Chem.*, 3585-96.

Haller et al., "Selectively protected disaccharide building blocks for modular synthesis of heparin fragments—part 2," 2002, *Eur. J. Org. Chem.* 2002:2033-38.

Haller et al., "Towards a modular approach for heparin synthesis," 2001, *J. Chem. Soc.,Perkin Trans.*, 1:814-22.

Hanashima et al., "Divergent synthesis of sialylated glycan chains: combined use of polymer support, resin capture-release, and chemoenzymatic strategies" Angew Chem Int Ed Engl, Jul. 4, 2005; 44(27):4218-24.

Hanson et al., "Chemoenzymatic synthesis of oligosaccharides and glycoproteins," Dec. 2004, *Trends Biochem. Sci.*, 29(12):656-63.

Hart et al., "Glycomics hits the big time" Cell, Nov. 24, 2010; 143(5):672-6.

Haslam et al., "Mass spectrometric analysis of N- and O-glycosylation of tissues and cells," Oct. 2006, *Curr. Opin. Struct. Biol.*, 16(5):584-91.

Haslam et al., "Characterizing the glycome of the mammalian immune system," Oct. 2008, *Immunology and Cell Biology*, 86(7):564-73.

Hattrup et al., "Structure and function of the cell surface (tethered) mucins," 2008, *Animal Review of Physiology*, 70:431-57.

He et al., "Stereoselective N-glycosylation by Staudinger ligation," Nov. 25, 2004, *Org. Lett.*, 6(24):4479-82.

Helenius et al., "Intracellular functions of N-linked glycans," Mar. 23, 2001, *Science*, 291(5512):2364-69.

Helenius et al., "Roles of N-linked glycans in the endoplasmic reticulum," 2004, *Annu. Rev. Biochem.* 73 :1019-1049.

Hirabayashi. "Concept, strategy and realization of lectin-based glycan profiling," Aug. 2008, *J. Biochem.*, 144(2):139-47.

Holeman, et al., "Carbohydrate diversity: synthesis of glycoconjugates and complex carbohydrates." 2004, *Curr. Opin. Biotechnol.* 15:615-22.

Honda et al., "C2-hydroxyglycosylation with glycal donors. Probing the mechanism of sulfonium-mediated oxygen transfer to glycal enol ethers," Jun. 26, 2002, *J. Am. Chem. Soc.* 124(25):7343-52.

Houseman et al., "Carbohydrate arrays for the evaluation of protein binding and enzymatic modification," 2002, *Chem. Biol.*, 9(4):443-54.

Ingale et al., "Robust immune responses elicited by a fully synthetic three-component vaccine," 2007, *Nat. Chem. Biol.*, 3:663-67.

Jansson et al., "2-(Trimethylsilyl) Ethyl Glycosides—Transformation into Glycopyranosyl Chlorides," 1990, *J. Org. Chem.*, 55:3181-85.

Karst et al. "Recent chemical and enzymatic approaches to the synthesis of glycosaminoglycan oligosaccharides," Oct. 2003, *Curr. Med. Chem.*, 10(19):1993-2031.

Kim et al., "Stereoselective Glycosylation Reactions with Chiral Auxillaries," Jan. 28, 2005, *Angewandte Chemie International Edition*, 44(6):947-49.

Kim et al., "A general strategy for stereoselective glycosylations" J Am Chem Soc, Aug. 31, 2005; 127(34):12090-7.

Kleene et al., "Glycans and neural cell interactions," Mar. 2004, *Nat. Rev. Neurosci.*, 5(3):195-208.

Kneipp et al., "Single molecule Raman scattering," Dec. 2006, *Applied Spectroscopy*, 60(12):322A-34A.

Koeller et al., "Enzymes for chemical synthesis," Jan. 11, 2001, *Nature*, 409(6817):232-40.

Koeller et al., "Synthesis of complex carbohydrates and glycoconjugates: enzyme-based and programmable one-pot strategies," 2000, *Chem. Rev.*, 100:4465-93.

Krusius et al., "Identification of an O-glycosidic mannose-linked sialylated tetrasaccharide and keratan sulfate oligosaccharides in the chondroitin sulfate proteoglycan of brain," Jun. 25, 1986, *J. Biol. Chem.*, 261(18):8237-42.

Kuduk et al., "Synthetic and immunological studies on clustered modes of mucin-related Tn and TF O-linked antigens: the preparation of a glycopeptide-based vaccine for clinical trials against prostate cancer." 1998, *J. Am. Chem. Soc.*, 120:12474-85.

Laurent et al., "Glycoarrays—tools for determining protein-carbohydrate interactions and glycoenzyme specificity" Chem Commun (Camb), Oct. 7, 2008; (37):4400-12.

Lepenies et al. "Applications of synthetic carbohydrates to chemical biology" Curr Opin Chem Biol, Jun. 2010; 14(3):404-11. Epub Mar. 12, 2010.

Leppanen et al., "A novel glycosulfopeptide binds to P-selectin and inhibits leukocyte adhesion to P-selectin," Aug. 27, 1999, *The Journal of Biological Chemistry*, 274(35):24838-48.

Leppanen et al., "Binding of glycosulfopeptides to P-selectin requires stereospecific contributions of individual tyrosine sulfate and sugar residues," 2000, *Glycobiology*, 10:1106-1107.

Lewis et al., "NeuA sialic acid 0-acetylesterase activity modulates a-acetylation of capsular polysaccharide in group B *Streptococcus*," 2007, *J. Biol. Chem.*, 282:27562-71.

Link et al., "Cell surface labeling of *Escherichia coli* via copper(1)-catalyzed [3+2] cycloaddition," 2003, *J. Am. Chem. Soc.*, 125(37):11164-65.

Liptàk et al., "Protecting Group Manipulations in Carbohydrate Synthesis," in *Carbohydrate Research Group of the Hungarian Academy of Sciences*. Elsevier Ltd. Debrecen, Hungary; 2007. pp. 203-213.

Logan et al., "Novel biosynthetic functions of lipopolysaccharide rfaJ homologs from Helicobacter pylori" Glycobiol, Jul. 2005; 15(7):721-33. Epub Apr. 6, 2005.

Maiti et al., "Chemical synthesis and proinflammatory responses of monophosphoryl lipid A adjuvant candidates" European J Org Chem., Jan. 1, 2010; 2010(1):80-91.

Manya et al., "Regulation of mammalian protein O-mannosylation: preferential amino acid sequence for O-mannose modification," Jul. 13, 2007, *The Journal of Biological Chemistry*, 282(28):20200-06.

Marino et al., "A systematic approach to protein glycosylation analysis: a path through the maze" Nat Chem Biol, Oct. 2010; 6(10):713-23.

Martin, "Dystroglycan glycosylation and its role in matrix binding in skeletal muscle," Aug. 2003, *Glycobiology*, 13(8):55R-66R.

Mast et al. "Family 47 alpha-mannosidases in N-glycan processing," 2006, *Methods Enzymol.*, 415:31-46.

Muir, "Semisynthesis of proteins by expressed protein ligation," 2003, *Annu. Rev. Biochem.*, 72:249-89.

Nana et al., "Mass spectrometric analysis of carbohydrate heterogeneity for the characterization of glycoprotein-based products," 2008, *Trends Glycosci. Glycotech.*, 20:97-116.

Naruchi et al., "Construction and structural characterization of versatile lactosaminoglycan-related compound library for the synthesis of complex glycopeptides and glycosphingolipids," Dec. 22, 2006, *J. Org. Chem.* 71(26):9609-21.

Nguyen et al., "Sulfide-mediated dehydrative glycosylation," 2001, *J. Am. Chem. Soc.* 123:8766-72.

Ning et al., "Visualizing metabolically labeled glycoconjugates of living cells by copper-free and fast huisgen cycloadditions," 2008, *Angew. Chem. Int. Ed.*, 47:2253-55.

North et al., "Mass spectrometry in the analysis of N-linked and O-linked glycans" Curr Opin Struct Biol, Oct. 2009; 19(5):498-506.

Ohtsubo et al., "Glycosylation in cellular mechanisms of health and disease," Sep. 8, 2006, *Cell*, 126(5):855-67.

Palcic, "Glycosyltransferases as biocatalysts" Curr Opin Chem Biol, Apr. 2011; 15(2):226-33.

Pang et al., "Human sperm binding is mediated by the sialyl-Lewis(x) oligosaccharide on the zona pellucida," Sep. 23, 2011, *Science*, 333(6050):1761-64.

Paulson et al., "Sweet spots in functional glycomics," May 2006, *Nat. Chem. Biol.*, 2(5):238-48.

(56) References Cited

OTHER PUBLICATIONS

Pearce et al., "Pathogenesis and transmission of swine origin A(H3N2)v influenza viruses in ferrets" Proc Natl Acad Sci U S A, Mar. 6, 2012; 109(10):3944-9. Epub Feb. 21, 2012.
Peters et al., "Solid-phase synthesis of a fucosylated glycopeptide of human-factor IX with a fucose-a-(1-0)-serine linkage," 1995, *J. Chem. Soc., Perkin Trans.*, 1:3017-22.
Prabhu et al., "New set of orthogonal protecting groups for the modular synthesis of heparan sulfate fragments," Dec. 25, 2003, *Org. Lett.*, 5(26):4975-78.
Raman et al., "Advancing glycomics: implementation strategies at the consortium for functional glycomics," 2006, *Glycobiology*, 16:82R-90R.
Raman et al., "Glycomics: an integrated systems approach to structure-function relationships of glycans," Nov. 2005, *Nat. Methods*, 2(11):817-24.
Ramasamy et al., "Oligosaccharide preferences of beta 1,4-galactosyltransferase-1: crystal structures of Met340His mutant of human betal,4-galactosyltransferase-1 with a pentasaccharide and trisaccharides of the N-glycan moiety," 2005, *J. Mol. Bioi.*, 353:53-67.
Ranzinger et al., "Glycome-DB.org: a portal for querying across the digital world of carbohydrate sequences" Glycobiology, Dec. 2009; 19(12):1563-7. Epub Sep. 16, 2009.
Rauvolfova et al., "Chemo-enzymatic synthesis of C-9 acetylated sialosides," Jul. 21, 2008, *Carbohydr. Res.*, 343 (10-11): 1605-11.
Rillahan et al., "Glycan microarrays for decoding the glycome" Annu Rev Biochem, 2011; 80:797-823.
Ritchie et al., "Glycosylation and the complement system," Feb. 2002, *Chem. Rev.*, 102(2):305-19.
Rogers et al., "Influenza C virus uses 9-O-acetyi-Nacetylneuraminic acid as a high affinity receptor determinant for attachment to cells," May 5, 1986, *J. Biol. Chem.*, 261(13):5947-51.
Roseman et al., "The mannose/N-acetylgalactosamine-4-SO4 receptor displays greater specificity for multivalent than monovalent ligands," May 18, 2001, *The Journal of Biological Chemistry*, 276(20): 17052-57.
Roth, "Protein N-glycolsylation along the secretory pathway: Relationship to organelle topography and function, protein quality control, and cell interactions," Feb. 2002, *Chem. Rev.*, 102(2):285-303.
Rudd et al., "Glycosylation and the immune system," Mar. 23, 2001, *Science*, 291:2370-76.
Sakagami et al., "A selective ring opening reaction of 4,6-0-benzylidene acetals in carbohydrates using trialkylsilane derivatives," 2000, *Tetrahedron Lett.*, 41:5547-51.
Santhanam et al., "Synthesis and biological evaluation of a lipid A derivative that contains an aminogluconate moiety," Oct. 4, 2004, *Chemistry*, 10(19):4798-807.
Sauerzapfe et al., "Chemo-enzymatic synthesis of poly-N-acetyllactosamine (poly-LacNAc) structures and their characterization for CGL2-galectin-mediated binding of ECM glycoproteins to biomaterial surfaces" Glycoconj J, Feb. 2009; 26(2):141-59.
Schachter, "The joys of HexNAc. The synthesis and function of N- and O-glycan branches," 2000, *Glycoconj. J.*, 17(7-9):465-83.
Schauer, "Achievements and challenges of sialic acid research," 2000, *Glycoconj. J.*, 17(9):485-99.
Schmaltz et al., "Enzymes in the Synthesis of Glycoconjugates," 2011, *Chemical Review*, 111:4259-307. epub Jul. 13, 2011.
Schmidt and Stumpp, "Glycosylimidate, 8. Synthese von 1-Thioglycosiden," Jul. 15, 1983 *Liebigs Ann. Chem.* 1983:1249-1256. English language abstract included.
Schmidt, "New methods for synthesis of glycosides and oligosaccharides—are there alternatives to the Koenigs-Knorr method," 1986, *Angew. Chem. Int. Ed. Engl.*, 25:212-35.
Schmidt et al., "Anomeric-oxygen activation for glycoside synthesis—the trichloroacetimidate method," 1994, *Adv. Carbohydr. Chem. Biochem.*, 50:21-123.
Schmidt et al., "Sweet new world: Glycoproteins in bacterial pathogens," Dec. 2003, *Trends Microbiol.*, 11(12):554-61.

Sears et al. "Toward automated synthesis of oligosaccharides and glycoproteins," Mar. 23, 2001, *Science*, 291(5512):2344-50.
Seeberger et al., "Solid-phase oligosaccharide synthesis and combinatorial carbohydrate libraries," Dec. 13, 2000, *Chem. Rev.*, 100:4349-94.
Serna et al., "Construction of N-glycan microarrays by using modular synthesis and on-chip nanoscale enzymatic glycosylation" Chemistry, Nov. 22, 2010; 16(44):13163-75.
Sjoberg et al., "Natural ligands of the B cell adhesion molecule CD22 beta can be masked by 9-O-acetylation of sialic acids," Jul. 1994, *The Journal of Cell Biology*, 126(2):549-62.
Sjolin et al., "Removal of Acyl Protective Groups from Glycopeptides: Base Does Not Epimerize Peptide Stereocenters and beta-Elimination is Slow," Jan. 26, 1996, *J. Org. Chem.*, 61(2):560-65.
Sjolin et al., "Use of fluorobenzoyl protective groups in synthesis of glycopeptides: beta-elimination of O-linked carbohydrates is suppressed," May 4, 2001, *J. Org. Chem.* 66(9):2957-65.
Smalheiser et al., "Structural analysis of sequences O-linked to mannose reveals a novel Lewis X structure in cranin (dystroglycan) purified from sheep brain," Sep. 11, 1998, *J. Biol. Chem.*, 273(37):23698-703.
Song et al., "Novel fluorescent glycan microarray strategy reveals ligands for galectins," Jan. 30, 2009, *Chem. Biol.*, 16(1):36-47.
Spik et al., "Primary structure of two sialylated triantennary glycans from human serotransferrin" FEBS Lett, Apr. 8, 1985; 183(1):65-9.
Stalnaker et al., "Site-mapping and characterization of O-glycan structures on alpha-dystroglycan isolated from rabbit skeletal muscle" J Biol Chem, Aug. 6, 2010; 285(32):24882-91. Epub May 27, 2010.
Stevens et al., "Structure and receptor specificity of the hemagglutinin from an H5N1 influenza virus" Science, Apr. 21, 2006; 312(5772):404-10. Epub Mar. 16, 2006.
Stevens et al., "Glycan microarray technologies: tools to survey host specificity of influenza viruses," Nov. 2006, *Nat. Rev. Microbiology*, 4(11): 857-64.
Sun et al., "Carbohydrate and protein immobilization onto solid surfaces by sequential Diels-Alder and azide-alkyne cycloadditions," 2006, *Bioconjugate Chem.* 17(1):52-57.
Sun et al., "Pre-activation-based one-pot synthesis of an alpha-(2,3)-sialylated core-fucosylated complex type bi-antennary N-glycan dodecasaccharide" Chemistry, 2008; 14(23):7072-81.
Taylor et al., "Paradigms for glycan-binding receptors in cell adhesion," Oct. 2007, *Curr. Opin. Cell. Biol.*, 19(5):572-77.
Teo et al., "Glycopeptide-specific monoclonal antibodies suggest new roles for O-GlcNAc" Nat Chem Biol, May 2010; 6(5):338-43. Epub Mar. 21, 2010.
Tsukamoto et al., "Synthesis of novel 25-substituted milbemycin A(4) derivatives and their acaricidal activity against *Tetranychus urticae*," Jan. 1997, *Biosci., Biotechnol., Biochem.*, 61(10):1650-57.
Turner et al., "Heats O Hydrogenation .9. Cyclic Acetylenes and Some Miscellaneous Olefins," 1972, *J. Am. Chem. Soc.*, 95:790-92.
Unverzagt et al.," Synthesis of glycopeptides and neoglycoproteins containing the fucosylated linkage region of-N-glycoproteins," Nov. 1994, *Bioorg. Med. Chem.*, 2(11): 1189-1201.
Unverzagt et al., "Synthesis of multiantennary complex type N-glycans by use of modular building blocks" Chemistry, Nov. 16, 2009; 15(45):12292-302.
Van Berkel et al., "Metal-free triazole formation as a tool for bioconjugation," Sep. 3, 2007, *ChemBioChem*, 8(13):1504-08.
Van Kooyk et al., "Protein-glycan interactions in the control of innate and adaptive immune responses," Jun. 2007, *Nat. Immunol.*, 9(6):593-601.
Van Reeuwijk et al., "POMT2 mutations cause alpha-dystroglycan hypoglycosylation and Walker-Warburg syndrome," Dec. 2005, *J. Med. Genet.*, 42(12):907-12.
Varki, "Biological roles of oligosaccharides: all of the theories are correct," Apr. 1993, *Glycobiology*, 3(2):97-130.
Wang et al., "Chemoenzymatic synthesis of GDP-L-fucose and the Lewis X glycan derivatives" Proc Natl Acad Sci U S A., Sep. 22, 2009; 106(38): 16096-101.
Watt et al., "A convergent strategy for the preparation of N-glycan core di-, tri-, and pentasaccharide thioaldoses for the site-specific

(56) References Cited

OTHER PUBLICATIONS glycosylation of peptides and proteins bearing free cysteines," Jan. 22, 2004, *Carbohydr. Res.*, 339(2):181-93.
Watt et al., "Site-specific glycosylation of an aglycosylated human IgG1-Fc antibody protein generates neoglycoproteins with enhanced function," Sep. 2003, *Chemistry & Biology*, 10(9):807-14.
Weerapana et al., "Asparagine-linked protein glycosylation: from eukaryotic to prokaryotic systems," Jun. 2006, *Glycobiology*, 16(6):91R-101R.
Werz et al., "Exploring the structural diversity of mammalian carbohydrates ("Glycospace") by statistical databank analysis," Oct. 19, 2007, *ACS Chem. Biol.*, 2(10):685-91.
Wittmann et al., "1H-tetrazole as catalyst in phosphomorpholidate coupling reactions: Efficient synthesis of GDP-fucose, GDP-mannose, and UDP-galactose," Apr. 4, 1997, *J. Org. Chem.*, 62(7):2144-47.
Wong et al., "Assembly of oligosaccharide libraries with a designed building block and an efficient orthogonal protection-deprotection strategy," 1998, *J. Am. Chem. Soc.*, 120:7137-38.
Yu et al., "Glycosyl trifluoroacetimidates. Part 1: Preparation and application as new glycosyl donors" Tetrahedron Letters 42, 2001; 2405-2407.
Yuen et al., "Brain contains HNK-1 immunoreactive O-glycans of the sulfoglucuronyl lactosamine series that terminate in 2-linked or 2,6-linked hexose (mannose)," Apr. 4, 1997, *The Journal of Biological Chemistry*, 272(14):8924-31.
Zachara et al., "The emerging significance of O-GlcNAc in cellular regulation," Feb. 2002, *Chem. Rev.*, 102(2):431-38.
Zaia, "Mass spectrometry and the emerging field of glycomics," Sep. 22, 2008, *Chem. Biol.*, 15(9):881-92.
Zaia, "Mass spectrometry of oligosaccharides," 2004, *Mass Spectrom. Rev.*, 23(3):161-227.
Zhang, et al., "Synthesis of Double-Chain Bis-Sulfone Neoglycolipids of the 2'Deoxyglobotriose, 3'-Deoxyglobotriose, and 6'-Deoxyglobotriose," 1995, *J. Org. Chem.*, 60:7304-15.
Zhang et al., "Efficient and practical syntheses of mannose tri-, tetra-, penta-, hexa-, hepta-, and octasaccharides existing in N-glycans," Feb. 21, 2002, *Tetrahedron: Asymmetry*, 13:243-52.
Zhang et al., "Modulation of innate immune responses with synthetic lipid A derivatives," Apr. 25, 2007, *J. Am. Chem. Soc.* 129(16):5200-16.
Zhang et al., "Innate immune responses of synthetic lipid A derivatives of Neisseria meningitides," 2008, *Chemistry*, 14(2):558-69.
Zhang et al., "Synthetic tetra-acylated derivatives of lipid A from Porphyromonas gingivalis are antagonists of human TLR4," Sep. 21, 2008, *Org. Biomol. Chem.*, 6(18):3371-81.
Zhu et al., "A highly efficient synthetic strategy for polymeric support synthesis of Le(x), Le(y), and H-type 2 oligosaccharides," Jun. 1, 2001, *Chem Eur J*, 7(11):2382-89.
Zhu et al., "A new set of orthogonal-protecting groups for oligosaccharide synthesis on a polymeric support," 2000, *Tetrahedron: Asymmetry*, 11:199-205.
Zhu et al., "New principles for glycoside-bond formation," Jan. 28, 2009, *Angewandte Chemie International Edition*, 48(11): 1900-34.
Albericio et al., "Coupling reagents and activation," in *Methods in enzymology-solid-phase peptide synthesis*. Fields (Ed.) Academic Press: New York; 1997. 289:104-26.
Aoki-Kinoshita, "Using glycome databases for drug discovery," 2008, *Exp. Opin. Drug. Discov.*, 3:877-90.
Aroca. *Surface Enhanced Vibrational Spectroscopy*, 2006, J Wiley & Sons, Chichester. Cover page, title page and table of contents.
Barondes et al., "Galectins. Structure and function of a large family of animal lectins." Aug. 19, 1994, *The Journal of Biological Chemistry*, 269(33):20807-10.
Boebel et al., "Probing the mechanism of sulfoxide-catalyzed hemiacetal activation in dehydrative glycosylation," Jul. 22, 2005, *J. Org. Chem.* 70(15):5818-26.
Boebel et al., "Sulfoxide covalent catalysis: application to glycosidic bond formation," 2003, *Angewandte Chemie International Edition*, 42:5874-77.

Boons et al., "Glycosyl phosphates: A new latent-active anomeric phosphorylation strategy," 1996, *Synlett*, 310-312.
Boons, "Strategies in oligosaccharide synthesis," 1996, *Tetrahedron*, 52:1095-121.
Carey, *Biochemical Applications of Raman and Resonance Raman Spectroscopies*, Academic Press, New York, 1982. Cover page, title page and table of contents.
Carpino et al., "9-Fiuorenylmethoxycarbonyl Amino-Protecting Group," 1972, *J. Org. Chem.*, 37:3404-09.
Carraway et al. "Cell signaling through membrane mucins," Jan. 2003, *Bioessays*, 25(1):66-71.
Chaney et al., "Aligned silver nanorod arrays produce high sensitivity surface-enhanced Raman spectroscopy substrates," 2005, *Appl. Phys. Lett.*, 87:31908.
Chen et al., "UDP-N-acetylglucosamine:alpha-3-D-mannoside beta-1, 2-N-acetylglucosaminyltransferase I and UDP-N-acetylglycosamine:alpha-6-D-mannoside beta-1, 2-N-acetylglucosaminyltransferase II in Caenorhabditis elegans," 2002, *Biochim. Biophys. Acta*, 1573:271-79.
Chiu et al., "In vivo targeting function of N-linked oligosaccharides with terminating galactose and N-acetylgalactosamine residues," 1994, *The Journal of Biological Chemistry*, 269:16195-202.
Cooper, "Galectinomics: finding themes in complexity," Sep. 19, 2002, *Biochim. Biophys. Acta*, 1572(2-3):209-31.
Coste et al. "Pybop—a new peptide coupling reagent devoid of toxic byproduct," 1990, *Tetrahedron Lett.*, 31:205-08.
Crocker et al., "Siglecs and their roles in the immune system," Apr. 2007, *Nat. Rev. Immunol.*, 7(4):255-66.
Dempski et al., "Oligosaccharyl transferase: gatekeeper to the secretory pathway," Dec. 2002, *Curr. Opin. Chem. Biol.*, 6(6):844-50.
De Vries et al., "The influenza A virus hemagglutinin glycosylation state affects receptor-binding specificity" Virology, Jul. 20, 2010; 403(1):17-25. Epub May 2, 2010.
Deras et al, "Synthesis of a high-mannose-type glycopeptide analog containing a glucose-asparagine linkage," Jul. 7, 1998, *Bioorg. Med. Chem. Lett.*, 8(13):1763-66.
Doores et al., "Direct deprotected glycosyl-asparagine ligation," Apr. 7, 2006, *Chem. Commun.(Camb)*, (13):1401-1403.
Driskell et al., "Infectious agent detection with SERS-active silver nanorod arrays prepared by oblique angle deposition," 2008, *IEEE Sensors J.*, 8:863-70.
Driskell et al., "Rapid microRNA (miRNA) detection and classification via surface-enhanced Raman spectroscopy (SERS)," 2008, *Biosens. Bioelectron.*, 24:917-22.
Driskell et al., "The use of aligned silver nanorod Arrays prepared by oblique angle deposition as surface enhanced Raman scattering substrates," 2008, *J. Phys. Chem. C*, 112:895-901.
Dwek, "Glycobiology: Toward Understanding the Function of Sugars," Mar. 28, 1996, *Chem. Rev.*, 96(2):683-720.
Endo, "O-mannosyl glycans in mammals," Dec. 6, 1999, *Biochim. Biophys. Acta*, 1473(1):237-46.
Feberwee et al., "Comparison of culture, PCR, and different serologic tests for detection of Mycoplasma gallisepticum and Mycoplasma synoviae infections," 2005, *Avian Dis.*, 49:260-68.
Felidj et al., "Controlling the optical response of regular arrays of gold particles for surface-enhanced Raman scattering," 2002, *Phys. Rev. B*, 65:075419.
Fraser-Reid et al. "n-Pentenyl glycosides in organic chemistry: a contemporary example of serendipity," 1992, *Synlett*, 927-42.
Freeze, "Genetic Defects in the Human Glycome" Nat Rev Genet, Jul. 2006; 7(7):537-51.
Freeze, "Congenital Disorders of Glycosylation: CDG-I, CDG-II, and beyond," Jun. 2007, *Curr. Mol. Med.*, 7(4):389-96.
Garcia et al., "Direct glycosylations with 1-hydroxy glycosyl donors using trifluoromethanesulfonic anhydride and diphenyl sulfoxide," 1997, J. Am. Chem. Soc., 119:7597-98.
Gildersleeve et al., "Scavenging byproduct in the sulfoxide glycosylation reaction: application to the synthesis of Cillamycin 0." 1999, *J. Am. Chem. Soc.*, 121:6176-82.
Green et al., "SERS substrates fabricated by island lithography: The silver/pyridine system," 2003, *J. Phys. Chem. B*, 107:13015-21.

(56) References Cited

OTHER PUBLICATIONS

Gupta et al., "High enhancement factor gold films for surface enhanced Raman Spectroscopy," 2003, *Chem. Physics Lett.*, 374:302-06.
Hanisch, "O-glycosylation of the mucin type," Feb. 2001, *Biol. Chem.*, 382(2):143-49.
Hansen et al., "NetOglyc: prediction of mucin type O-glycosylation sites based on sequence context and surface accessibility," 1998, *Glycoconj.*, 15:115-30.
Haynes et al., "Nanosphere lithography: A versatile nanofabrication tool for studies of size-dependent nanoparticle optics," 2001, *J. Phys. Chem. B*, 105:5599-5611.
Henry et al., "Dystroglycan inside and out," 1999, *Curr. Opin. Cell Biol.*, 11:602-07.
Hollingsworth et al., "Mucins in cancer: protection and control of the cell surface," Jan. 2004, *Nat. Rev. Cancer*, 4(1):45-60.
Houseman et al., "The role of ligand density in the enzymatic glycosylation of carbohydrates presented on self-assembled monolayers of alkanethiolates on gold," 1999, *Angew. Chem. Int. Ed.* 38:782-85.
Inazu et al., "A New Simple Method for the Synthesis of N(Alpha)-Fmoc-N(Beta)Glycosylated-L-Asparagine Derivatives," 1993, *Synlett*, 869-870.
Itakura et al., "Systematic comparison of oligosaccharide specificity of Ricinus communis agglutinin I and Erythrina lectins: a search by frontal affinity chromatography" J Biochem, Oct. 2007; 142(4):459-69. Epub Jul. 25, 2007.
Jansson et al., "2-(Trimethylsilyl) Ethyl Glycosides .3. Synthesis, Anomeric Deblocking, and Transformation into 1,2-Trans 1-O-Acyl Sugars," 1988, *J. Org. Chem.* 53:5629-47.
Jonke et al., "Solid-phase oligosaccharide synthesis of a small library of N-glycans" Chemistry, Jan. 23, 2006; 12(4):1274-90.
Kahl et al., "Analysis of plasmon resonance and surface-enhanced Raman scattering on periodic silver structures," 2000, *Phys. Rev. B*, 61:14078-88.
Karamanska et al., "Surface plasmon resonance imaging for real-time, label-free analysis of protein interactions with carbohydrate microarrays," Jan. 2008, *Glycoconj. J.*, 25(1):69-74.
Kelly et al., "The optical properties of metal nanoparticles: The influence of size, shape, and dielectric environment," 2003, *J. Phys. Chem. B*, 107:668-77.
Kerker et al., "Effect of Aggregates on Extinction and Surface-Enhanced Raman-Scattering Spectra of Colloidal Silver," 1984, *J. Phys. Chem.*, 88:3168-70.
Kneipp et al, "Extremely large enhancement factors in surface-enhanced Raman scattering for molecules on colloidal gold clusters," 1998, *Applied Spectroscopy*, 52:1493-97.
Kneipp et al. (Ed.), *Surface-Enhanced Raman Scattering: Physics and Applications*, Springer-Verlag: Berling, Germany; 2006. Cover page, title page and table of contents.
Konig et al., "A New Method for Synthesis of Peptides- Activation of Carboxyl Group with Dicyclohexylcarbodiimide Using 1-Hydroxybenzotriazoles as Additives," 1970, *Chem. Ber.* 103:788-91.
Kunkel et al., "Structural and functional analysis of the surface protein of human coronavirus OC43," Jul. 1993, *Virology*, 195(1):195-202.
Kunz et al., "Protecting-Group-Dependent Stability of Intersaccharide Bonds-Synthesis of a Fucosyi-Chitobiose Glycopeptide," 1988, *Angew. Chem. Int. Ed. Engl.*, 27:1697-1699.
Lairson et al., "Glycosyltransferases: structures, functions, and mechanisms," 2008, *Annu. Rev. Biochem.*, 77:521-55.
Lamblin et al. "Human airway mucin glycosylation: a combinatory of carbohydrate determinants which vary in cystic fibrosis," Sep. 2001, *Glycoconj. J.*, 18(9):661-84.
Liu et al., "Galectins as modulators of tumour progression," Jan. 2005, *Nat. Rev. Cancer*, 5(1):29-41.
Liu et al., "Angle dependent surface enhanced Raman scattering obtained from a Ag nanorod array substrate," 2006, *Appl. Phys. Lett.*, 89:173134.

Long, *Raman Spectroscopy*, McGraw-Hill: New York; 1977. Cover page, title page and table of contents.
MacIndoe et al., "A unique and highly facile method for synthesising disulfide linked neoglycoconjugates: a new approach for remodelling of peptides and proteins," 1998, *Chem. Commun.*, 847-848.
Mandal et al., "Investigation of 9-0-acetylated sialoglycoconjugates in childhood acute lymphoblastic leukaemia," 2000, *Br. J. Haematol.*, 110:801-12.
Matrosovich et al., "Avian influenza A viruses differ from human viruses by recognition of sialyloligosaccharides and gangliosides and by a higher conservation of the HA receptor-binding site," 1997, *Virology*, 233:224-34.
McCreery, *Raman Spectroscopy for Chemical Analysis*, John Wiley & Sons, Inc.: New York; 2000. Cover page, title page and table of contents.
Michele et al. "Post-translational disruption of dystroglycan-ligand interactions in congenital muscular dystrophies," Jul. 25, 2002, *Nature*, 418(6896):417-22.
Michele et al., "Dystrophin-glycoprotein complex: post-translational processing and dystroglycan function," 2003, *J. Biol. Chem.*, 278:15457-60.
Miyamoto, "Clinical applications of glycomic approaches for the detection of cancer and other diseases," Dec. 2006, *Curr. Opin. Mol. Ther.*, 8(6):507-13.
Mizuno et al., "A simple method for the synthesis of N-beta-glycosylated-asparagine and -glutamine derivatives," 1999, *Synthesis*, 162-165.
Moskovits. "Surface-enhanced Rama spectroscopy: a brief retrospective," 2005, *J. Raman Spectros.*, 36:485-96.
Mrksich et al., "Biospecific Adsorption of Carbonic-Anhydrase to Self-Assembled Monolayers of Alkanethiolates That Present Benzenesulfonamide Groups on Gold," 1995, *J. Am. Chem. Soc.*, 117:12009-10.
Mulvaney et al., "Three-layer substrates for surface-enhanced Raman scattering: preparation and preliminary evaluation," 2003, *J. Raman Spectros.*, 34:163-71.
Muntoni et al., "Defective glycosylation in muscular dystrophy," Nov. 2, 2002, *Lancet*, 360(9343):1419-21.
Nie et al., "Probing Single Molecules and Single Nanoparticles by Surface-Enhanced Raman Scattering," Feb. 21, 1997, *Science*, 275(5303):1102-06.
Nikoobakht et al., B., "Surface-enhanced Raman scattering of molecules adsorbed on gold nanorods: off-surface plasmon resonance condition," 2002, *Chem. Phys. Lett.*, 366:17-23.
Paulsen. "Advances in selective chemical syntheses of complex oligosaccharides," 1982, *Angew. Chem. Int. Ed. Engl.*, 21:155-73.
Plante, et al., "Development of an automated oligosaccharide synthesizer," 2003, *Adv. Carbohydr. Chem. Biochem.* 58:35-54.
Rabinovich et al., "Galectins and their ligands: amplifiers, silencers or tuners of the inflammatory response?" Jun. 2002, *Trends Immunol.*, 23(6):313-20.
Revell et al., "Self-assembled carbohydrate monolayers: Formation and surface selective molecular recognition," 1998, *Langmuir*, 14:4517-24.
Rief et al., "Single Molecule Force Spectroscopy on Polysaccharides by Atomic Force Microscopy," Feb. 28, 1997, *Science*, 275(5304):1295-97.
Rosen et al., "The Selectins and Their Ligands," Oct. 1994, *Curr. Opin. Cell Biol*, 6(5):663-73.
Sasaki et al., "Detection of O-mannosyl glycans in rabbit skeletal muscle alpha-dystroglycan," Nov. 27, 1998, *Biochim. Biophys. Acta*, 1425(3):599-606.
Sentandreu et al., "Characterization of Oligosaccharides Attached to Threonine and Serine in a Mannan Glycopeptide Obtained from Cell Wall of Yeast," 1969, *Carbohydr. Res.*, 10:584-85.
Shanmukh et al., "Identification and classification of respiratory syncytial virus (RSV) strains by surface-enhanced Raman spectroscopy and multivariate statistical techniques," Mar. 2008, *Anal. Bioanal. Chem.*, 390(6):1551-55.
Shanmukh et al., "Rapid and sensitive detection of respiratory virus molecular signatures using a silver nanorod array SERS substrate," Nov. 2006, *Nano Lett.*, 6(11):2630-36.

(56) References Cited

OTHER PUBLICATIONS

Smith et al., "Surface plasmon resonance imaging studies of protein-carbohydrate interactions," May 21, 2003, *J. Am. Chem. Soc.*, 125(20):6140-48.
Spinke et al., "Molecular Recognition at Self-Assembled Monolayers—the Construction of Multicomponent Multilayers," 1993, *Langmuir*, 9:1821-25.
Spinke et al., "Molecular Recognition at Self-Assembled Monolayers—Optimization of Surface Functionalization," 1993, *J. Chem. Phys.*, 99:7012-19.
Stockle et al., "Sub-wavelength Raman spectroscopy on isolated silver islands," 2000, *Vib. Spectros.*, 22:39-48.
Taniguchi et al., "Decoding sugar functions by identifying target glycoproteins," Oct. 2006, *Curr. Opin. Struct. Biol.*, 16(5):561-66.
Teo et al., "Generation of O-GlcNAc specific monoclonal antibodies using a novel synthetic immunogen" The FASEB Journal, Apr. 2010; 24(1): Supple 904.7.
Timmer et al., "Probing glycomics," Feb. 2007, *Curr. Opin. Chem. Biol.*, 11(1):59-65.
Toshima et al. "Recent progress in O-glycosylation methods and its application to natural-products synthesis," 1993, *Chem. Rev.*, 93:1503-31.
Traving et al., "Structure, function and metabolism of sialic acids," Dec. 1998, *Cell Mol. Life Sci.*, 54(12):1330-49.
Unverzagt, "Chemoenzymatic Synthesis of a Sialylated Undecasaccharide—Asparagine Conjugate" Angew. Chem. Int. Ed. Engl., 1996; 35(20): 2350-2353.
Varki et al. (Ed.), *Essentials of Glycobiology* $2^{nd}$ *Edition*. Cold Spring Harbor Laboratory Press: Cold Spring Harbor, New York; 2009. Cover page, title page and table of contents.
Whitesell et al., "Enzymatic Grooming of Organic Thin-Films," 1994, *Angew. Chem. Int. Ed. Eng.*, 33:871-73.
Wong et al., "Enzymes in Organic-Synthesis -Application to the Problems of Carbohydrate-Recognition .2," 1995, *Angew. Chem., Int. Ed. Engl.* 34:521-46.
Wuts and Greene (Eds.), *Greene's Protective Groups in Organic Synthesis, Fourth Edition*. John Wiley & Sons: Hoboken, NJ; 2007. Cover page, title page and table of contents.

\* cited by examiner

COMPOUNDS AND METHODS FOR CHEMICAL AND CHEMO-ENZYMATIC SYNTHESIS OF COMPLEX GLYCANS

This application is the § 371 U.S. National Stage of International Application No. PCT/US2012/030408, filed 23 Mar. 2012, which claims the benefit of U.S. Provisional Application Ser. No. 61/467,661, filed Mar. 25, 2011, which are incorporated herein by reference in their entireties.

STATEMENT OF GOVERNMENT RIGHTS

This invention was made with government support under Grant No. 1R01GM090269-01 awarded by the National Institutes of Health. The government has certain rights in the invention.

BACKGROUND

There is a growing appreciation that posttranslational modifications, such as protein glycosylation, dramatically increase polypeptide complexity and function (Rudd et al., 2001 Science 291:2370-2376; Varki, 1993 Glycobiology 3:97-130; Dwek, 1996 Chem. Rev. 96:683-720; Roth, 2002 Chem. Rev. 102:285-303; Ritchie et al., 2002 Chem. Rev. 102:305-319; Zachara and Hart, 2002 Chem. Rev. 102:431-438; Bertozzi and Kiessling, 2001 Science 291:2357-2364; Kleene and Schachner, 2004 Nat. Rev. Neurosci. 5:195-208; Bucior and Burger, 2004 Curr. Op. Struct. Biol. 14:631-637; Schmidt et al., 2003 Trends Microbiol. 11:554-561). For example, almost all cell surface and secreted proteins are modified by covalently-linked carbohydrate moieties and the glycan structures on these glycoproteins have been implicated as essential mediators in processes such as protein folding, cell signaling, cell migration, fertilization, embryogenesis, neuronal development, hormone activity, and the proliferation of cells and their organization into specific tissues (Taylor and Drickamer, 2007 Curr. Opin. Cell. Biol. 19:572-577). In addition, overwhelming data supports the relevance of glycosylation in pathogen recognition, inflammation, innate immune responses, and the development of autoimmune diseases and cancer (Ohtsubo and Marth, 2006 Cell 126:855-867; Brockhausen, 2006 EMBO Rep. 7:599-604; Brown et al., 2007 Crit. Rev. Biochem. Mol. Biol. 42:481-515; Crocker et al., 2007 Nat. Rev. Immunol. 7:255-266; van Kooyk and Rabinovich, 2008 Nat. Immunol. 9:593-601). The importance of protein glycosylation is also underscored by the developmental abnormalities observed in a growing number of human disorders (known as Congenital Disorders of Glycosylation or CDGs), caused by defects in the glycosylation machinery (Freeze, 2007 Curr. Mol. Med. 7:389-396).

Almost all naturally occurring protein glycosylations can be classified as either N-glycosides whereby N-acetyl glucosamine is linked to the amide side chain of an asparagine, or as O-glycosides whereby a saccharide is linked to the hydroxyl of serine, threonine or tyrosine (Buskas et al., 2006 Glycobiology 16:113R-136R). The biosynthesis of N-linked oligosaccharides occurs in the endoplasmic reticulum (ER) and Golgi complex. In the ER, a dolichol-linked $Glc_3Man_9GlcNAc_2$ oligosaccharide precursor is biosynthesized and transferred en bloc to an Asn-X-Ser/Thr sequon on newly synthesized polypeptides through the action of the multi-subunit oligosaccharide transferase complex (Dempski and Imperiali, 2002 Curr. Opin. Chem. Biol. 6:844-850; Weerapana and Imperiali, 2006 Glycobiology 16:91R-101R). Subsequent trimming and processing of the transferred oligosaccharide results in a $Man_3GlcNAc_2$ core structure, which is transported to the medial stacks of the Golgi complex where maturation of the oligosaccharide gives rise to extreme structural diversity (Ellgaard and Helenius, 2003 Nat. Rev. Mol. Cell Biol. 4:181-191; Helenius and Aebi, 2004 Annu Rev. Biochem. 73:1019-1049; Helenius and Aebi, 2001 Science 291:2364-9; Mast and Moremen, 2006 Methods Enzymol. 415:31-46); (Essentials of Glycobiology. 2nd edition. Varki et al., ed., Cold Spring Harbor (NY): Cold Spring Harbor Laboratory Press; 2009). The complexity of N-glycan structures is largely based on the cell-specific expression of a collection of glycosyl transferases that specify the extension of oligosaccharide structures onto the trimmed $Man_3GlcNAc_2$ core structure. The switch from structural uniformity in the ER to diversification in the Golgi complex coincides with a marked change in glycan function. In the early secretory pathway, the glycans have a common role in the promotion of protein folding, quality control, and certain sorting events. This is in contrast to their roles in the Golgi complex, in which they are modified to perform a wide spectrum of functions displayed by the mature glycoproteins.

The first enzyme needed for the biosynthesis of complex N-linked glycans is GlcNAcT-I, which adds a β(1-2)GlcNAc moiety to the core mannoside to produce a hybrid structure (Schachter, 2000 Glycoconj. J. 17:465-483; Chen et al., 2002 Biochim. Biophys. Acta 1573:271-279). Further processing of the resulting saccharide by mannosidases creates the precursor for GlcNAcT-II, which catalyzes the conversion of a hybrid structure into the precursor for complex N-glycan biosynthesis. Thus, each of the GlcNAc moieties of the resulting compound is converted into a complex bi-antennary structure. The formation of multi-antennary structures, require additional GlcNAc moieties that are added by GlcNAcT-IV, V and VI. Each of the resulting GlcNAc moieties can be extended into a complex oligosaccharide that can be quite diverse in structure. Furthermore, GlcNAcT-III can add a bisecting moiety that cannot be extended by further monosaccharide moieties. Collectively, the GlcNAcT's can create N-glycans that have as many as five branches (Schachter, 2000 Glycoconj. J. 17:465-483; Chen et al., 2002 Biochim. Biophys. Acta 1573:271-279). Finally, further diversification can take place by the addition of a core α(1-6)-fucoside to the GlcNAc moiety linked to the side chain of Asn. It is important to note that the action of one glycosyl transferase can preclude the action of another one and therefore only a subset of linkages performed by the GlcNAc transferases can occur on any one N-glycan. For example, GlcNAcT-V requires the prior activation by GlcNAcT-II. GlcNAcT-III and V are mutually exclusive as the action of one may inhibit the action of the other. The mode of GlcNAcT-VI is not well understood but may require prior branching by GlcNAcT-II and GlcNAcT-V.

SUMMARY

The present invention provides chemical and chemo-enzymatic methods for the synthesis of a wide array of oligosaccharides. The chemical and chemo-enzymatic methods of the invention include a chemical synthesis phase, and an optional enzymatic synthesis phase.

In the chemical phase of the synthesis, an orthogonally protected oligosaccharide core is sequentially deprotected and linked with one, two, three, four, or five or more glycosyl donors resulting in an extended oligosaccharide which is a complex bi-, tri-, tetra- or penta-antennary glycan (collectively referred to herein as a "multi-antennary" glycan) having two, three, four or five branching arms, respectively. This resulting multi-antennary glycan, known herein as the "enzymatic precursor," can be deprotected and/or unmasked in order to yield a final oligosaccharide product, or it can be partially or entirely deprotected and selectively extended enzymatically in an enzymatic phase to yield a final complex oligosaccharide product. The chemically synthesized multi-antennary glycan is termed an "enzymatic precursor" because it is the reactant upon which subsequent selective enzymatic extension is performed during the optional enzymatic phase of the synthesis.

In one aspect, the invention provides an orthogonally protected oligosaccharide core structure. In one embodiment, the oligosaccharide core structure is a branched trisaccharide, exemplified as formula (I). The branched trisaccharide is formed from three mannose units, (Man₃), and is preferably α-D-mannopyranosyl-(1→6)-[α-D-mannopyranosyl-(1→3)]-D-mannopyranose (or pyranoside), more preferably α-D-mannopyranosyl-(1→6)-[α-D-mannopyranosyl-(1→3)]-β-D-mannopyranose (or pyranoside). A protected glucosamine moiety is optionally present at the C-4 position of the central or branching mannoside of the trimannoside.

A preferred orthogonally protected branched trisaccharide contains at least two orthogonal protecting groups, and has the formula (I):

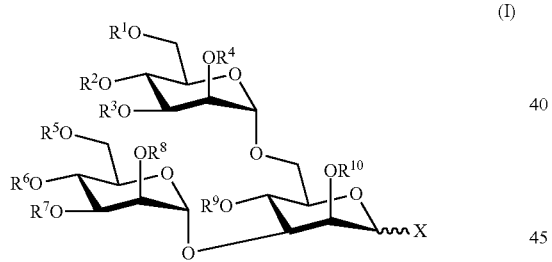

(I)

wherein each of $R^1$, $R^4$, $R^6$, and $R^8$ is independently an orthogonal protecting group or a permanent protecting group; wherein the orthogonal protecting group is preferably selected from levulinoyl (Lev); 9-fluorenylmethoxycarbonyl (Fmoc); allyloxycarbonyl (Alloc); 2-naphthylmethyl (Nap) or 1-naphthylmethyl (1-Nap); benzoyl (Bz); difluorobenzoyl (dfBz); pivaloyl levulinoyl (PivLev); pivaloyl benzoyl (PivBz); para-methoxybenzyl ether (PMB); methoxy phenyl ether (MP); allyl ether (Allyl); chloroacetyl ester (ClAc); trichloroacetyl ester (Cl₃Ac), trifluoroacetyl ester (F₃Ac); and silyl ethers such as t-butyldimethyl silyl (TBS), t-butyldiphenyl silyl, 2-(trimethylsilyl)ethoxymethyl ether (SEM) and texyldimethyl silyl (TDS); and wherein the permanent protecting group is stable under conditions used to remove the orthogonal protecting groups and is preferably benzyl ether (Bn) or acetyl ester (Ac);

each of $R^2$, $R^3$, $R^5$, $R^7$, and $R^{10}$ is independently a permanent protecting group that is stable under conditions used to remove the orthogonal protecting groups and is preferably benzyl ether (Bn) or acetyl ester (Ac);

$R^9$ is an orthogonal protecting group; a permanent protecting group; or a saccharide, preferably a glucosamine including an N-acetyl glucosamine (GlcNAc) or a derivative thereof; wherein the glucosamine is preferably a protected and/or masked glucosamine derivative containing at least one permanent protecting group and/or at least one masking group;

X is —OR¹⁵ or —SR¹⁶;

$R^{15}$ is H, alkyl, cycloalkyl, substituted alkyl or cycloalkyl, alkenyl, substituted alkenyl, alkynyl, substituted alkynyl, aryl or substituted aryl; a protecting group such as a silyl or substituted silyl, preferably thexyldimethylsilyl (TDS), t-butyldimethylsilyl (TBS), t-butyldiphenyl silyl (TBDPS), triisopropylsilyl (TIPS), trimethylsilyl (TMS), or triethylsilyl (TES); methyl (Me), acetyl (Ac), benzyl (Bn), 2-naphthylmethyl (Nap) or 1-naphthylmethyl (1-Nap); an anomeric spacer or linker; a fluorous tag; or an anomeric leaving group such as trichloroacetimidate —C(NH)—CCl₃, phenyltrifluoroacetimidate —C(NPh)-CF₃, trifluoroacetimidate —C(NH)—CF₃; thioformimidate, thioalkyl, thiophenyl, or S-glycosyl N-phenyltrifluoroacetimidate; and $R^{16}$ is H, alkyl, cycloalkyl, substituted alkyl or cycloalkyl, alkenyl, substituted alkenyl, alkynyl, substituted alkynyl, aryl, or substituted aryl, preferably methyl, ethyl, phenyl, tosyl, or tolyl.

Protecting groups recited herein are intended to be exemplary and nonlimiting; additional protecting groups (temporary or permanent, orthogonal, masking, hydroxyl-functional, amino-functional, and the like) are well-known to the skilled artworker and can be employed in the chemical and chemo-enzymatic methods of the invention. See, e.g., Greene's Protective Groups in Organic Synthesis (Wuts and Greene (Eds.), *Greene's Protective Groups in Organic Synthesis, Fourth Edition*. John Wiley & Sons: Hoboken, N.J.; 2007).

Compound 110 is an exemplary orthogonally protected branched trisaccharide core:

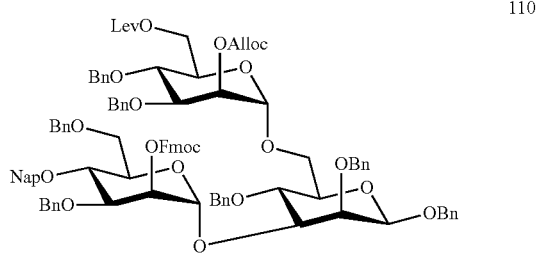

110

In another embodiment, the oligosaccharide core further optionally contains one or two glycoside moieties linked to the reducing end of the branched trimannoside core structure to form a tetrasaccharide or a pentasaccharide, respectively. The one or two glycoside moieties linked to the reducing end of the trimannoside core structure are preferably protected or masked glucosamine moieties (GlcNR) such as GlcNAc or a derivative thereof. When a glucosamine, GlcNAc or a derivative thereof (e.g., a protected or masked form thereof) is present at the reducing end of the oligosaccharide core, it is optionally modified by a fucoside at position C-6.

A preferred orthogonally protected branched pentasaccharide contains at least two orthogonal protecting groups and has the formula (II):

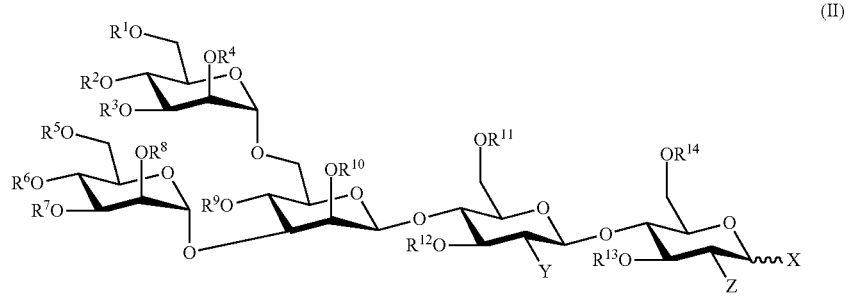

(II)

wherein $R^1$, $R^2$, $R^3$, $R^4$, $R^5$, $R^6$, $R^7$, $R^8$, $R^9$, $R^{10}$, and X are as in formula (I);

each of $R^{11}$, $R^{12}$, and $R^{13}$ is independently a permanent protecting group that is stable under conditions used to remove the orthogonal protecting groups and is preferably benzyl (Bn) or acetyl (Ac);

$R^{14}$ is a permanent protecting group that is stable under conditions used to remove the orthogonal protecting groups and is preferably benzyl (Bn) or acetyl (Ac); or a protected fucoside moiety;

Y and Z are each independently —$N_3$ or —$NHR^{17}$; and $R^{17}$ is H or a protecting group preferably selected from the group consisting of 9-fluorenylmethoxycarbonyl (Fmoc), allyloxycarbonyl (Alloc), [2,2,2-Trichloroethoxycarbonyl] (Troc), trichloroacetyl (TCA), trifluoroacetyl (TFA), acetyl (Ac), phthalimido (Phth), carbobenzyloxy (Cbz) or tert-butoxycarbonyl (Boc).

Compound 1 is an exemplary orthogonally protected branched pentasaccharide core:

groups preferably do not cause cleavage of other protecting groups present on the disaccharide building block. In other embodiments, however, a particular order of cleavage is observed in order to sequentially cleave each orthogonal protecting group.

The oligosaccharide core structure is optionally equipped with a spacer or linker at the C-1 position (at the reducing end) to facilitate conjugation chemistry. The invention is not limited to a particular anomeric spacer, which can be selected based upon the intended purpose for including the spacer. The spacer can function as a chain terminating linker. Inclusion of a spacer is useful, for example, for the fabrication of oligosaccharide arrays and for the preparation of immunogens. Exemplary spacers include —$(CH_2)_n$NRCbz and —$[(CH_2)_2$—O—$(CH_2)_2]_n$NRCbz where n=3-6 and R=Bn, Ph, or H, fluorous linkers, and linkers or spacers that are attached to or are activated for attachment to a solid support.

1

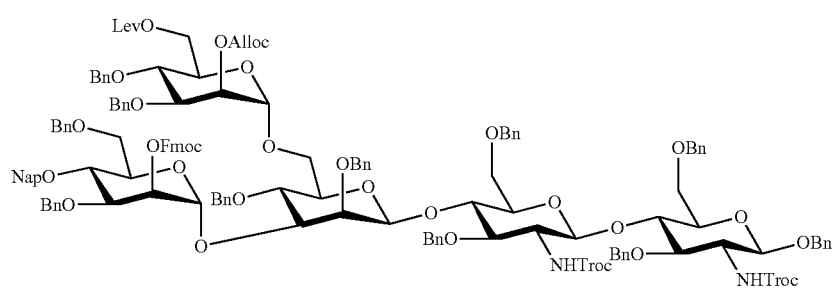

It should be understood that the invention further includes a tetrasaccharide, as in formula (II), which has "X" at the anomeric center in place of the second glucosamine at the reducing end.

Silyl or substituted silyl groups that are O-linked at the anomeric carbon to form silyl ethers are preferably cleavable with HF/pyridine and tetrahydrofuran (THF) or tetrabutylammonium fluoride (TBAF)/acetic acid/THF or moderately strong acetic conditions. Silyl or substituted silyl groups function as temporary protecting groups when O-linked at the anomeric carbon of the disaccharide and higher order saccharides of the invention.

Alkyl, alkenyl and alkynyl may include one, two, three, four, five, six, seven, eight, nine, ten, eleven, twelve or more carbon atoms. Aryl includes any aromatic hydrocarbon including phenyl, benzyl, tosyl and the like.

In some embodiments, conditions effective to cause cleavage of each of the different orthogonal protecting In another aspect, the invention includes a method for making an orthogonally protected oligosaccharide core. An exemplary synthesis of a branched pentasaccharide core is shown in Scheme 1, which can readily be modified by one of skill in the art, using the same monomeric building blocks, to make a trisaccharide core or tetrasaccharide core described herein.

In another aspect, the invention provides protected and/or masked monosaccharide and disaccharide glycosyl donors which have utility for extending the branched trisaccharide, tetrasaccharide and pentasaccharide core to yield multi-antennary glycans. The glycosyl donors contain one or more hydroxyl groups protected by a permanent protecting group (such as benzyl ether, OBn) and/or masked by a masking group (such as an acetyl ester, OAc).

In one embodiment, the glycosyl donor is a protected and/or masked glucosamine having the formula (III):

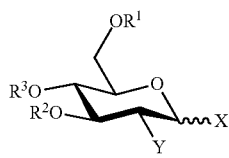

(III)

wherein $R^1$, $R^2$, and $R^3$ are each independently a masking group or a permanent protecting group; wherein the masking group is preferably an acyl (e.g., acetyl) such as —C(O)$R^3$, or a carbonate, such as —C(O)O$R^3$; wherein $R^3$ is an aliphatic group or an aromatic/aryl group; and wherein the permanent protecting group is preferably benzyl (Bn); and wherein the masking group and permanent protecting group are both stable under conditions used to remove orthogonal protecting groups; and Y and X are as in formula (I).

In a preferred embodiment, $R^1=R^2=R^3$.

Compounds 4 and 5 are exemplary glucosamine glycosyl donors:

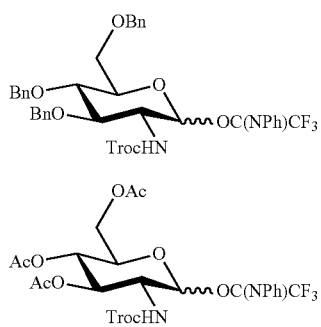

4

5

In another embodiment, the glycosyl donor is a protected and/or masked lactosamine having the formula (IV):

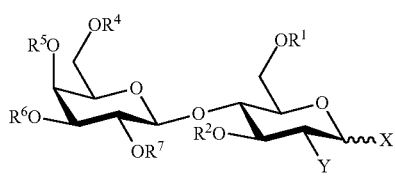

(IV)

wherein each of $R^1$, $R^2$, $R^4$, $R^5$, $R^6$, and $R^7$ are each independently a masking group or a permanent protecting group; wherein the masking group is preferably an acyl (e.g., acetyl) such as —C(O)$R^3$, or a carbonate, such as —C(O)O$R^3$; wherein $R^3$ is an aliphatic group or an aromatic/aryl group; and wherein the permanent protecting group is preferably benzyl (Bn); and wherein the masking group and permanent protecting group are both stable under conditions used to remove orthogonal protecting groups; and Y and X are as in formula (I).

In a preferred embodiment, $R^1=R^2$ and $R^4=R^5=R^6=R^7$; in another preferred embodiment, $R^1=R^2=R^4=R^5=R^6=R^7$.

Compounds 2 and 3 are exemplary lactosamine glycosyl donors:

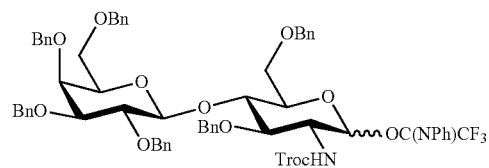

2

3

In the chemical method of the invention, and in the chemical phase of the chemo-enzymatic method of the invention, the orthogonally protected oligosaccharide core is sequentially deprotected and linked with one, two, three, four, five or more glycosyl donors in a chemical synthesis resulting in a complex bi-, tri-, tetra- or penta-antennary glycan (collectively referred to herein as a "multi-antennary" glycan) which has two, three, four or five branching arms, respectively. The orthogonally protected oligosaccharide core is selectively deprotected in a series of reactions that remove protecting groups. A deprotection sequence is utilized such that cleavage conditions for the orthogonal protecting group being removed do not cause cleavage of other protecting groups that are present on the oligosaccharide core. For example, in some embodiments it may be advantageous to cleave one particular orthogonal protecting group before another, if the cleavage conditions for the second protecting group would cause cleavage of the first protecting group as well. In preferred embodiments, orthogonal protecting groups can be removed in any order.

Cleavage of an orthogonal protecting group converts the oligosaccharide core into a glycosyl acceptor. As each orthogonal protecting group is cleaved, the deprotected site(s), which are typically hydroxyl(s), become available for glycosylation with a glycosyl donor to effect chain extension. The remaining protecting groups are removed in later reaction steps, yielding a deprotected multi-antennary glycan, known herein as the "enzymatic precursor," from which all protecting groups have been removed except those being used to "mask" the glycan during the optional subsequent enzymatic phase of the chemo-enzymatic synthesis. The masking groups (e.g., the acyl esters and/or carbonates) are positioned on one or more of the glycan's "arms." Masking disables the glycosyl-accepting properties of the oligosaccharide at those positions. In addition, many glycosyl transferases are known to recognize N-acetyl lactosamine (LacNAc) but not N-acetyl glucosamine (GlcNAc). The enzymatic phase of the chemo-enzymatic synthesis takes advantage of the fact that these enzymes will only glycosylate the non-acetylated lactosamine arm(s) and not the acetylated lactosamine and terminal GlcNAc moieties. The deprotected, masked glycan is now ready to serve as a substrate for the selected carbohydrate processing enzymes during the enzymatic phase of the chemo-enzymatic method of the invention. It should be clear that a large number of multi-antennary glycans can be produced using the method of the invention, which can be collected to form a chemical library. The oligosaccharides produced using the invention, as well as chemical libraries containing these oligosaccharides, are also included in the invention.

Exemplary embodiments of the synthesis of multi-antennary glycans from orthogonally protected oligosaccharide core molecules are shown in Schemes 3 and 4. As each orthogonal protecting group is removed to reveal a free hydroxyl (thereby converting the oligosaccharide into a glycosyl acceptor), the glycosyl donor of interest is attached using an appropriate promoter such as trifluoromethanesulfonic acid (TfOH) or trimethylsilyl trifluoromethanesulfonate (TMSOTf) (which are especially useful for imidates), and an organic solvent, such as dichloromethane, diethyl ether, acetonitrile or dichloroethane, at an appropriate temperature to effect glycosylation. See, e.g., Schmidt et al., 2003 Trends Microbiol. 11:554-561; and Schmidt, 1986 Angew. Chem. Int. Ed. Engl. 25:212-235; Zhu et al., 2009, Angew. Chem. Int. Ed. Engl., 48, 1900-1934 (describing suitable promoters and catalysts). After the required orthogonal protecting groups have been removed and chain extension is complete, any remaining orthogonal and permanent protecting groups are chemically removed. The resulting oligosaccharide will be "masked" at selected positions in order to provide control over enzymatic extension in the enzymatic phase. In this fashion, entire libraries of asymmetric bi-, tri-, tetra- and penta-antennary "enzymatic precursor" oligosaccharides are produced.

In the enzymatic phase of the chemo-enzymatic synthesis of the invention, which is optional, further chain extension is effected enzymatically. The multi-antennary oligosaccharide is linked successively with one or more carbohydrate processing enzymes. At any point in the enzymatic phase, masking groups (typically, acetyl) can be removed in order to make the previously masked end(s) available for chain extension reactions. The researcher can specify the identity and order of use of the carbohydrate processing enzymes so as to achieve synthesis of a desired complex glycan. In addition to extending the chain(s), carbohydrate processing enzymes may be used to trim or remodel the glycan during synthesis so as to achieve the desired product. Exemplary enzymatic syntheses are shown in Schemes 5, 6 and 7, below. Entire libraries of asymmetric, multi-antennary glycans, such as N-glycans, can be produced.

The wide variety of multi-antennary complex glycans that can be produced using the method of the invention has many scientific and medical applications. Scientific knowledge of the biological roles of various carbohydrates has been hampered by the lack of reliable synthetic methods, and the present invention provides a rapid and effective synthesis of complex glycans for use in research, drug screening, diagnostics and the like. The compounds of the invention can be used to make glycan microarrays and as components of other research tools useful, for example, in the study of glycomics. They may also be used for the preparation of glycopeptides, glycoproteins, antibodies, and other glycoconjugates. They can be linked to a multivalent scaffold to increase affinity for a carbohydrate binding protein. An exemplary synthesis of an oligosaccharide with a potential biomedical use, a compound found in oocytes, is described below.

DETAILED DESCRIPTION OF ILLUSTRATIVE EMBODIMENTS

Figure 1:
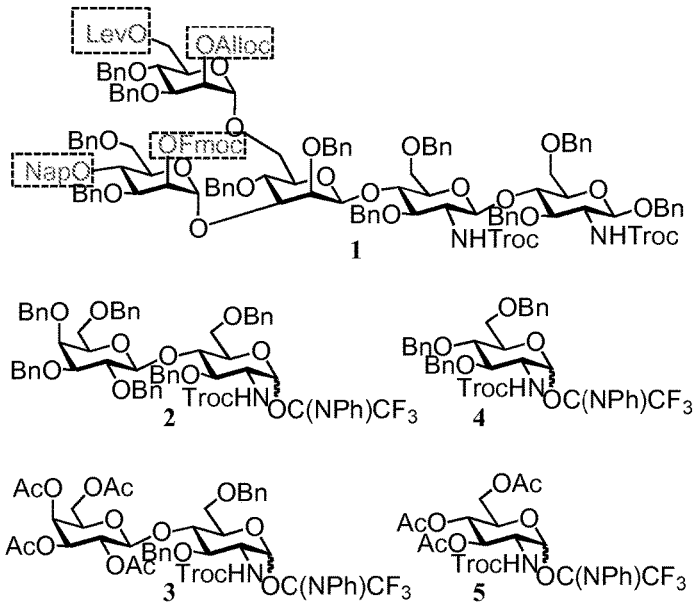
FIG. 1 shows an exemplary orthogonal protected core pentasaccharide (1) and exemplary glycosyl donors (2-5) for extension; orthogonal protecting groups are indicated in hatched boxes.

Glycomics is an emerging field of integrated research to study structure-function relationships of complex carbohydrates. Key glycomics technologies include mass spectrometric profiling of glycan structures isolated from cells and tissues (Haslam et al., 2006 Curr. Opin. Struct. Biol. 16:584-591; Nana et al., 2008 Trends Glycosci. Glycotech. 20:97-116; Zaia, 2004 Mass Spectrom. Rev. 23:161-227), glycogene microarray technology for measuring the expression levels of glycoenzymes and glycan-binding proteins and screening for glycan-protein interactions using glycan and lectin array technologies (Paulson et al., 2006 Nat. Chem. Biol. 2:238-248; Miyamoto, 2006 Curr. Opin. Mol. Ther. 8:507-513; Feizi et al., 2003 Curr. Opin. Struct. Biol. 13:637-645; de Paz et al., 2006 Methods Enzymol. 415:269-292; Alvarez and Blixt, 2006 Methods Enzymol. 415:292-310; Hirabayashi, 2008 J. Biochem. 144:139-147). The diverse data sets generated by the use of these technologies are beginning to provide an understanding of the fundamental structure-function relationships of glycans. Critical components that enable this process are bioinformatics platforms that store, integrate, process, and disseminate the data in a meaningful way (Raman et al., 2005 Nat. Methods 2:817-824; Raman et al., 2006 Glycobiology 16:82R-90R; Aoki-Kinoshita, 2008 Exp. Opin. Drug Discov. 3:877-890).

In many cases, well-defined oligosaccharides can only be obtained by chemical- or enzymatic synthesis. Although these approaches are still plagued with problems, synthetic compounds are increasingly being used to address important problems in glycobiology research and for vaccine and drug discovery. In this respect, new leaving groups for the anomeric center have been developed, which can be introduced under mild reaction conditions and are sufficiently stable for purification and storage for a considerable period of time. The most commonly employed glycosyl donors include anomeric fluorides, trichloroacetimidates, and thioglycosides. Convergent synthetic strategies that allow the convenient assembly of complex oligosaccharides from properly protected building units involving a minimum number of synthetic steps have become available.

Despite these advances, the synthesis of N-linked oligosaccharides is plagued by many difficulties. In this respect, chemical oligosaccharide synthesis involves elaborate and lengthy protecting group and glycosylation procedures and even in specialized laboratories the preparation of one compound takes, in general, takes many months to as much as a year to complete. This problem is compounded by the fact that synthetic efforts are generally focused on the preparation of one-compound-at-the-time. Although enzymatic approaches have been successfully employed for the facile extension of synthetic core structures (Buskas et al., 2006 Glycobiology 16:113R-136R; Muir, 2003 Annu Rev. Biochem. 72:249-289), they can only provide symmetrical structures (i.e., the same oligosaccharide extension at each branching point of a bi- or tri-antennary structure). Combined these problems have made it difficult to prepare libraries of complex bi-, tri- and tetra-antennary N-linked oligosaccharides for glycomics research.

The need for efficient approaches for oligosaccharide synthesis has stimulated the development of chemo-enzymatic methods (Hanson et al., 2004 Trends Biochem. Sci. 29:656-663; Wong et al., 1995 Angew. Chem., Int. Ed. Engl. 34:521-546; Koeller and Wong, 2001 Nature 409:232-240; Gijsen et al., 1996 Chem. Rev. 96:443). The enzymatic methods bypass the need for protecting groups since the enzymes control both the regio- and stereo-selectivity of glycosylation. Two basic approaches for enzymatic oligosaccharide synthesis are available, namely, the use of glycosyl transferases and reverse activity of glycosyl hydrolases. Glycosyl transferases are essential enzymes for oligosaccharide biosyntheses and transfer a sugar residue from a sugar-nucleotide mono- and di-phosphate to a maturing oligosaccharide chain. These enzymes are highly regio- and stereoselective and can be obtained by cloning and overexpression. The use of these enzymes combined with sophisticated methods to regenerate sugar nucleotides has led to the preparation of large collections of complex oligosaccharides and glycopeptides. The power of synthesis using glycosyltransferases was, for example, elegantly demonstrated by the construction of a range of glycopeptides derived from the N-terminus of P-Selectin Glycoprotein Ligand-1 (Leppanen et al., 1999 J. Biol. Chem. 274:24838-24848; Leppanen et al., 2000 Glycobiology 10:1106-1107), which is part of a family of adhesion proteins involved in the inflammatory cascade. A serious limitation of current chemo-enzymatic synthetic approaches is that it does not provide entry into biologically important asymmetrically branched oligosaccharides.

The present invention provides chemical and chemo-enzymatic methods for the synthesis of a wide array of oligosaccharides, including asymmetrically branched glycans. The chemo-enzymatic method of the invention includes a chemical synthesis phase, and an optional enzymatic synthesis phase. Initially, an orthogonally protected oligosaccharide core is sequentially deprotected and linked with one, two, three, four, or more glycosyl donors in a chemical synthesis resulting in a complex bi-, tri-, tetra- or penta-antennary glycan (collectively referred to herein as a "multi-antennary" glycan) which has two, three, four or five branching arms, respectively. The glycosyl donors contain one or more hydroxyl groups protected by a permanent protecting group (such as benzyl, Bn, which forms a benzyl ether) and/or masked by a masking group (such as acetyl, Ac, to form an acetyl ester). This resulting multi-antennary glycan, known herein as the "enzymatic precursor," can be deprotected and/or unmasked in order to yield a final oligosaccharide product, or it can be selectively extended enzymatically in an enzymatic phase to yield a final complex oligosaccharide product. The chemically synthesized multi-antennary glycan is termed an "enzymatic precursor" because it is the reactant upon which subsequent selective enzymatic extension is performed during the optional enzymatic phase of the synthesis.

The novel chemical compounds described herein, including the oligosaccharide core compounds, the enzyme precursor compounds, and the final oligosaccharide products, as well as all intermediate compounds described herein, are also included in the invention, as are their methods of making and methods of use.

In a preferred embodiment, the chemical synthesis phase occurs prior to the enzymatic synthesis phase. Employing a chemical synthesis phase prior to the enzymatic phase advantageously permits the synthesis of an asymmetric enzymatic precursor, which in turn permits the synthesis of biologically relevant asymmetrically branched oligosaccharides. It should be understood that enzymatic synthesis may optionally precede chemical synthesis, and further that multiple alternating chemical and enzymatic synthesis phases can be utilized as desired for the production of any particular oligosaccharide.

Oligosaccharide Core

The oligosaccharide core, which functions as a reactant in the chemical synthesis phase of the synthetic methods of the invention, is a branched oligosaccharide. Preferably, it is a branched trisaccharide, tetrasaccharide, pentasaccharide, hexasaccharide or heptasaccharide. In one embodiment, the trisaccharide core is a branched trimannoside core ($Man_3$), preferably α-D-mannopyranosyl-(1→6)-[α-D-mannopyranosyl-(1→3)]-D-mannopyranose (or pyranoside). A protected glucosamine moiety is optionally present at the C-4 position of the central or branching mannoside of the trimannoside.

The oligosaccharide core optionally contains one or two glycoside moieties linked to the reducing end of the trimannoside core structure to form a tetrasaccharide or a pentasaccharide. The one or two glycoside moieties linked to the reducing end of the trimannoside core structure are preferably protected glucosamine moieties (GlcNR) such as GlcNAc or a derivative thereof. When a glucosamine, GlcNAc or a derivative thereof is present at the reducing end of the oligosaccharide core, it is optionally modified by a fucoside at position C-6. A preferred oligosaccharide core is the pentasaccharide $Man_3GlcNAc_2$. An example of a preferred pentasaccharide is compound 1 (FIG. 1).

The oligosaccharide core is orthogonally protected with two, three, four or five orthogonal protecting groups. Preferably, four different orthogonal protecting groups are used. The orthogonal protecting groups are positioned at hydroxyl groups on the two terminal moieties that form the non-reducing ends of the oligosaccharide core. More specifically, orthogonal protecting groups are positioned at hydroxyl groups at one or more of the following ring positions: C-2 of the 1,6-linked mannoside, C-6 of the 1,6 linked mannoside, C-2 on the 1,3-linked mannoside, C-4 on the 1,3-linked mannoside, and C-4 of the central mannoside. As noted above, in N-linked glycans there is optionally an additional bisecting protected glucosamine moiety at the C-4 position of what is, in the tetrasaccharide or pentasaccharide embodiment, the central mannoside moiety. When two orthogonal protecting groups are used, a biantennary glycan can be produced; when three orthogonal protecting groups are used, a biantennary or triantennary glycan can be produced; and when four orthogonal protecting groups are used, a biantennary, triantennary or tetraantennary glycan can be produced. Using four orthogonal protecting groups on the oligosaccharide core thus affords the most flexibility during synthesis. "Orthogonal" protecting groups, as that term is used herein, are those that can be sequentially removed, preferably but not necessarily in any order, and include, without limitation, levulinoyl (Lev); 9-fluorenylmethoxycarbonyl (Fmoc); allyloxycarbonyl (Alloc); 2-naphthylmethyl (Nap) or 1-naphthylmethyl (1-Nap); benzoyl (Bz);

difluorobenzoyl (dfBz); pivaloyl levulinoyl (PivLev); pivaloyl benzoyl (PivBz); para-methoxybenzyl ether (PMB); methoxy phenyl ether (MP); allyl ether (Allyl); chloroacetyl ester (ClAc); trichloroacetyl ester ($Cl_3Ac$), trifluoroacetyl ester ($F_3Ac$); and silyl ethers such as t-butyldimethyl silyl (TBS), t-butyldiphenyl silyl, 2-(trimethylsilyl)ethoxymethyl ether (SEM) and texyldimethyl silyl (TDS). For example, in compound 1 (FIG. 1), para-methoxybenzyl or methoxy phenyl can replace Nap; Allyl can replace Alloc; ClAc and/or $Cl_3Ac$ and $F_3Ac$ may replace Fmoc; and any of the silyl groups (SEM, TBS, TDS, etc.) may replace Nap or Lev.

The other hydroxyl groups on the oligosaccharide core, that is, the ones that are not orthogonally protected, are preferably protected with permanent protecting groups. Permanent protecting groups are stable to the reaction conditions used to remove orthogonal protecting groups, but can be removed at the final stage of the chemical synthesis phase. An exemplary permanent protecting group is benzyl (Bn). Various protecting groups (orthogonal, temporary and permanent) as wells linkers, spacers and other derivatizing agents suitable for use in the compounds and methods of the invention are described in International Patent Publication WO2010/117803, published Oct. 14, 2010.

The reducing end of the oligosaccharide core can be permanently protected, as with OBn group as shown for compound 1 (FIG. 1), or it can be linked to a spacer or linker. More particularly, the reducing end of the oligosaccharide core can be —OR wherein R is H, alkyl, cycloalkyl, substituted alkyl or cycloalkyl, alkenyl, substituted alkenyl, alkynyl, substituted alkynyl, aryl or substituted aryl, such as methyl, ethyl, phenyl, tosyl or tolyl; a silyl or substituted silyl, including thexyldimethylsilyl (TDS), t-butyldimethylsilyl (TBS), t-butyldiphenyl silyl (TBDPS), triisopropylsilyl (TIPS), trimethylsilyl (TMS), or triethylsilyl (TES); a protecting group such as methyl (Me), acetyl (Ac), benzyl (Bn), 2-naphthylmethyl (NAP) or 1-naphthylmethyl (1-NAP); an anomeric spacer or linker; a fluorous tag; or an anomeric leaving group such as trichloroacetimidate —C(NH)—$CCl_3$, phenyltrifluoroacetimidate —C(NPh)-$CF_3$, trifluoroacetimidate —C(NH)—$CF_3$; thioformimidate, thioalkyl, thiophenyl, or S-glycosyl N-phenyltrifluoroacetimidate. For example, the anomeric center can be protected by a silyl ether, for example as a thexyldimethyl silyl (TDS) glycoside. This functionality can easily be removed by treatment with hydrogen fluoride pyridine complex in tetrahydrofuran without affecting the other protecting groups. The resulting lactol can then be converted into a trichloroacetimidate by employing potassium carbonate ($K_2CO_3$) or cesium carbonate ($Cs_2CO_3$) or NaH and trichloroacetonitrile in DCM (Prabhu et al., Org. Lett. 2003, 5, 4975-4978), thereby activating the molecule as a glycosyl donor. Alternatively, the anomeric center can be protected via a covalent linkage to a spacer, preferably a (C1-C8) amino benzyloxycarbonyl protected spacer, such as an α-anomeric N-(benzyl)benzyloxycarbonyl protected aminopentenyl spacer. The spacer or linker is optionally functionalized, allowing for further derivatization or chemical reaction such as linkage to a substrate, a protein, another carbohydrate, or any other desired compound. Alternatively, the spacer or linker may be covalently linked to a substrate such as a bead, gel, surface and the like, thereby permitting immobilization of the oligosaccharide during the chemical and/or enzymatic synthesis phases. In some embodiments the reducing end of the oligosaccharide core can contain an anomeric leaving group, so as to enable the oligosaccharide core to function as a glycosyl donor.

If the oligosaccharide core includes one or more glucosamine residues, the amino moieties of the glucosamine residues are protected or masked, for example using an amine functional protecting group such as Troc, trichloroacetyl (TCA), trifluoroacetyl (TFA), phthalimido (Phth), azide, or acetyl (Ac).

Glycosyl Donor

In the chemical phase of the synthetic methods, the orthogonally protected oligosaccharide core is sequentially deprotected and linked with two or more glycosyl donors under conditions to selectively extend the oligosaccharide. Orthogonal protecting groups can be removed sequentially, one at a time. In some embodiments, orthogonal protecting groups can be sequentially removed in any order (corresponding to a strict definition of orthogonality); however, in other embodiments, although the orthogonal protecting groups can be removed sequentially, not every possible deprotection sequence will be effective. For example, there may be a protecting group A that can be removed without affecting B, but not the other way around, as when A is more base labile than B. Thus, it should be understood that as the term "orthogonal" or "orthogonally" is used here in, it specifies that sequential removal can occur, but not necessarily in all possible orders. One at a time, protecting groups are removed and the oligosaccharide core is linked with a glycosyl donor. Up to four, five or even more orthogonal protecting groups can be present on a single oligosaccharide core, and thus up to four, five or even more glycosyl donors can be employed, in sequential reactions, thereby generating a enzymatic precursor oligosaccharide that has up to five non-reducing ends (antennae or "arms").

Glycosyl donors are typically monosaccharides or disaccharides. Preferred glycosyl donors include protected and/or masked glucosamine (a monosaccharide) and lactosamine (a disaccharide that contains glucosamine). Particularly preferred glycosyl donors for use in the chemical phase of the synthesis are compounds 2, 3, 4 and 5 shown in FIG. 1. The amine group of the glucosamine moiety is protected with an amine functional protecting group, such as Troc, TFA, TCA, Phth or azide; or it may be masked with Ac. The reducing end of the glycosyl donor preferably contains an anomeric leaving group, such as trichloroacetimidate —C(NH)—$CCl_3$, phenyltrifluoroacetimidate —C(NPh)-$CF_3$, trifluoroacetimidate —C(NH)—$CF_3$; thioformimidate, thioalkyl, thiophenyl, or S-glycosyl N-phenyltrifluoroacetimidate.

The ring hydroxyls of the glycosyl donor are either protected with a permanent protecting group, such as benzyl, Bn, or they are masked with a masking group such as an acetyl ester (OAc). Stable, non-labile esters and carbomates are typically good masking groups. More generally, a masking group can be —C(O)R or —C(O)OR where R is an aliphatic group, or an aromatic/aryl group. Masking groups are known to the art and are stable to conditions used to remove orthogonal protecting groups; they are also stable to conditions used later in the chemical synthesis to remove so-called "permanent" hydroxyl and amine protecting groups, such as benzyl ethers and Troc carbamate. They can remain in place during the enzymatic phase of the synthesis to block enzymatic extension of the oligosaccharide at those sites. When and if desired, at any point in the enzymatic synthesis, masking groups can be removed (for example, Ac can be removed by deacetylation) so as to allow for enzymatic extension at that position at that stage of the enzymatic synthesis. Which hydroxyls are protected, and which are masked, is determined by the synthetic sequence that is to be carried out. In some embodiments of the glycosyl donor, the ring hydroxyls are protected but not masked (see, e.g., compounds 2 and 4); in other embodiments, the ring hydroxyls are masked but not protected (see, e.g., compound 5); and in yet other embodiments, some ring hydroxyls are masked, while others are protected (see, e.g., compound 3). It should be understood that especially in the case of disaccharide glycosyl donors (such as lactosamine), the ring hydroxyls can be either all protected, all masked, or some protected and some masked.

"Enzyme Precursor" Oligosaccharide

At the end of the chemical synthesis phase of the synthetic method of the invention, the chemically synthesized multi-antennary oligosaccharide is deprotected; that is, any remaining permanent hydroxyl and amino protecting groups (the amines may be, for example, acetylated) are removed. The deprotected multi-antennary oligosaccharide is typically a complex, asymmetric oligosaccharide that is now ready to be extended in the optional enzymatic phase of the chemo-enzymatic synthesis, and thus is termed an "enzyme precursor" oligosaccharide. The enzyme precursor oligosaccharide preferably contains masking groups positioned at one or more ring hydroxyls and/or amines which function to prevent a carbohydrate processing enzyme from extending the chain at that position. It will be remembered that enzymatic extension produces the same oligosaccharide extension at each branching point of a bi- or tri-antennary structure, but that this can be prevented or controlled via the use of masking groups. By chemically producing asymmetric "enzyme precursors" having masking groups at strategic positions, and having chain extensions derived from GlcNAc and LacNAc, the enzymatic extension of the oligosaccharide can be controlled.

Figure 2:
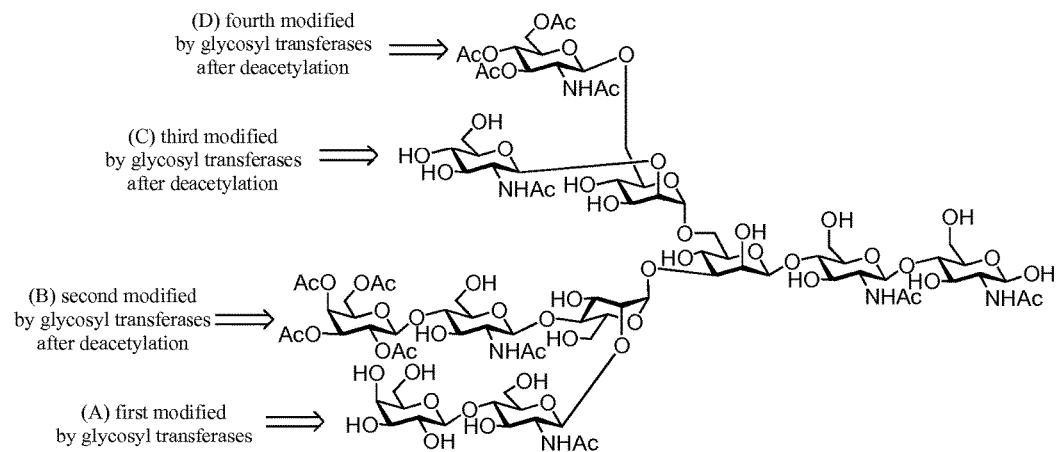
FIG. 2 shows an exemplary complex tetra-antennary glycan where each branching arm can be selectively modified.

The number of different orthogonal protecting groups used on the oligosaccharide core determines the how many branches the enzyme precursor oligosaccharide contains. Thus, when four orthogonal protecting groups are used, a tetra-antennary glycan can be produced (see, for example, FIG. 2). Of course, a tri-antennary or bi-antennary glycan can be produced from that same oligosaccharide core if one or two orthogonal protecting groups are removed without reaction with a glycosyl donor. See, e.g., compounds 27 and 32, which are tri-antennary enzyme precursor oligosaccharides produced from a tetra-orthogonally protected core molecule, wherein an Alloc protecting group and a Nap protecting group, respectively, were removed without linking a glycosyl donor at those respective sites. When three orthogonal protecting groups are used and extended by glycosyl donors, a maximum of three branches (i.e., a triantennary glycan) can be produced, and so on. Other glycosyl donors besides the GlcNAc and LacNAc donors described herein can also be used, including branched glycosyl donors, thereby further increasing the branching of the resulting multi-antennary glycan.

Enzymatic Phase

Protecting groups per se are not needed in the enzymatic phase of the chemo-enzymatic synthesis since enzymes control both the regio- and stereo-selectivity of glycosylation. However, carbohydrate processing enzymes generally will add the same oligosaccharide extension at each arm, typically at arms having the same monosaccharide unit at the nonreducing end, of a bi-, tri- or tetra-antennary structure. Thus, in order to achieve the most control over the enzymatic phase of the synthesis, the enzymatic precursor compound is preferably masked by a masking group on any arm that would otherwise serve as a substrate for the enzyme, but is not intended to be extended in that round of enzymatic synthesis.

One surprising result of this work is that the carbohydrate processing enzymes were still able to effectively extend one arm of the glycan while the other arm(s) were protected with acetyl esters. It was not known in advance whether the masking groups would interfere with the glycosyl accepting properties of the unmodified arms; the enzymes might still have been active, but not able to recognize the arms that do not contain the masking groups. However, in all cases tested, the enzymes functioned as intended to catalyze extensions of the exposed arm(s).

Carbohydrate processing enzymes useful in the enzymatic phase of the chemo-enzymatic method include, for example, glycosyl transferases, glycosidases and sulfotransferases. Glycosyl transferases transfer a sugar residue from a sugar-nucleotide mono- and di-phosphate to a maturing oligosaccharide chain. Exemplary carbohydrate processing enzymes include glycosyltransferases, such as glucosyltransferases (GlcTs) and glucouronyltransferases (GlcATs), mannosyltransferases (ManTs), sialyltransferases (SiaTs), galactosyltransferases (GalTs), fucosyltransferases (FecTs) and N-acetylhexoaminyltransferases (GlcNAct and GalNAcT); glycosidases such as glycoside hydrolyases, including exo-glycosidases and endo-glycosidases; and glycosynthases such as exo-glycosynthases and endo-glycosynthases. See Schmaltz et al., Chem Rev 2001, 111, 4259-4307). Some carbohydrate processing enzymes are commercially available; others can be isolated from organisms that produce them, or cloned, expressed, and isolated. Carbohydrate processing enzymes can be found in all organisms including microorganisms such as bacteria and protists, yeasts, fungi, plants, and animals, including humans. The invention is not limited by the type of carbohydrate processing enzyme or its source. The particular carbohydrate processing enzymes selected for use in the enzymatic synthesis phase of the chemo-enzymatic synthetic method are determined and defined by the particular end-product oligosaccharide that is desired.

Enzymatic extension depends on an adequate supply of monosaccharide glycosyl donors in order to extend the growing multi-antennary oligosaccharide in each round of enzymatic synthesis. Disaccharide or higher order glycosyl donors may be used. Examples of glycosyl donors useful in the enzymatic phase of the chemo-enzymatic method of the invention include CMP-sialic acid, CMP-Neu5Ac, GDP-Fuc, UDP-GlcNAc, UDP-Gal, UDP-GalNAc, and the like. Advantageously, derivatives of glycosyl donors that have been modified for use in subsequent chemical or enzymatic reactions can be employed for enzymatic chain extension. For example, a glycosyl donor can contain an azido- or alkyne group, making it suitable for us in click chemistry. The resulting oligosaccharides, as well as oligosaccharide intermediates, can optionally be further enzymatically modified by sulfates using appropriate sulfotransferases.

Final Oligosaccharide Product

The oligosaccharide produced by chemical or chemoenzymatic synthesis described herein is a complex, asymmetric, multi-antennary glycan. The resulting multi-antennary glycan can contain 8, 9, 10, 11, 12, 13, 14, 15, 16, 17, 18, 19, 20 or even more monosaccharide residues, in almost limitless combination, composition, order, linkage position and linkage stereochemistry ($\alpha$, $\beta$).

Importantly, the synthetic methods describe herein, and in particular the chemo-enzymatic technology described herein, make it possible to conveniently prepare libraries of complex asymmetrically substituted N-glycans. An important feature of the technology is the use of a core oligosaccharide, exemplified by compound 1 in FIG. 1, which at selected branching positions is modified by orthogonal protecting groups, making it possible to selectively modify each of the desired hydroxyls of the core oligosaccharide with a unique saccharide structure using chemical glycosylation methodology. The chemo-enzymatic synthetic strategy of the invention exploits the fact that many relevant enzymes do not recognize a terminal GlcNAc, and that extension by $\beta$-1,4-Gal to produce LacNAc is required to produce an arm that can be extended by the relevant enzymes.

This technology thus not only allows many different complex glycans to be synthesized from the same oligosaccharide core, but also even from the same enzyme precursor oligosaccharide, by changing the type and order of the enzymatic reactions used in the enzyme phase. The chemo-enzymatic method of the invention additionally allows a researcher to envision a complex, multi-antennary oligosaccharide product, then readily synthesize that product by combining known enzymatic specificities with orthogonal chemical synthesis as described herein.

EXAMPLES

The present invention is illustrated by the following examples. It is to be understood that the particular examples, materials, amounts, and procedures are to be interpreted broadly in accordance with the scope and spirit of the invention as set forth herein.

Example 1. Chemo-Enzymatic Reactions

We have developed a chemo-enzymatic technology that makes it possible to conveniently prepare libraries of complex asymmetrically substituted N-glycans. A key feature of the technology will be the use of the core oligosaccharide 1, which at key branching positions, is modified by the orthogonal protecting groups Lev, Fmoc, Alloc, and 2-naphtyl methyl ether (Nap) (FIG. 1), which makes it possible to selectively modify each of the key hydroxyls of the core pentasaccharide with a unique saccharide structure using chemical glycosylation methodology.

We have observed difficulties when highly complex oligosaccharide donors were attached to core compound 1. To address this difficulty, we describe here a novel chemoenzymatic approach in which the relatively simple LacNAc and GlcNAc donors 2-5 are used for chemical glycosylation of compound 1. After removal of the protecting groups except the acetyl esters, a "precursor" oligosaccharide is obtained where each antenna can be selectively extended by glycosyl transferases to give a large number of highly complex asymmetrically substituted bi-, tri-, and tetra-antennary glycans. Selective enzymatic modification at each branching point will be feasible because each of these positions will be modified by a unique saccharide moiety. In this respect, GlcNAc or LAcNAc are recognized by different glycosyl transferases and C-3 acetylated LAcNAc and GlcNAc, are not recognized by glycosyl transferases. The latter moieties can, however, become acceptors for glycosyl transferases by removal of the acetyl ester.

As a generic example, oligosaccharide 1 is a "precursor" structure for complex tetra-antennary glycans (FIG. 2) that can easily be prepared by sequential removal of the orthogonal protecting groups combined with chemical glycosylations with glycosyl donors 2-5 and removal of the Troc and benzyl. The acetyl esters of the terminal moieties B and D will not be cleaved. A key feature of the resulting compound is that each of the four branching points is modified by a different extension saccharide and, hence, it offers an exciting opportunity to selectively modify each branching arm by a unique oligosaccharide using a range of glycosyl transferases. Our strategy is based on the fact that the enzymes will only glycosylate the non-acetylated lactosamine arm and not the acetylated lactosamine and terminal GlcNAc moieties. Furthermore, it is known that terminal GlcNAc moieties are not recognized by the various sialyl and fucosyl transferases. Thus, for example, the non-acetylated lactosamine moiety can first be modified by an $\alpha(2-3)$- or $\alpha(2-6)$-sialic acid moiety employing a relevant and commercially available sialyl transferase. Next, the resulting sialylated lactosamine moiety can be selectively fucosylated using an $\alpha(1-3)$-fucosyl transferase to give a $SLe^x$ structure. Alternatively, a $Le^y$ motif can be installed by selective glycosylation of the non-acetylated lactosamine moiety by an $\alpha(1-2)$ and $\alpha(1-3)$ fucosyltransferase, and a type 1 structure can be installed by using an $\alpha(1-3)$-N-acetyl galactosylamine transferase and an $\alpha(1-2)$ fucosyltransferases. The next step of the synthesis may entail selective glycosylation of the non-acetylated GlcNAc moiety by extension with a $\beta(1-4)$-galactosyl residue using an appropriate galactosyl transferase. The resulting LacNAc residue can then selectively be modified with various sialyl- and fucosyl moieties as described above. Next, the acetyl esters will be removed using mild basic conditions and the resulting free LacNAc and GlcNAc moieties, can sequentially be modified using appropriate glycosyl transferases as described above.

Chemical Synthesis of Orthogonally Protected Core Oligosaccharide 1.

Orthogonally protected pentasaccharide 1 was prepared from monosaccharide building blocks 6, 7, 11, 14 and 17 (Scheme 1). Thus, mannosyl donor 6 was coupled with glucosamine acceptor 7 using the Crich protocol (Crich and Li, 2000 J. Org. Chem. 65:801-805; Crich and Sun, 1997 J. Am. Chem. Soc. 119:11217-11223) to provide $\beta$-mannoside 8 as the predominant compound. In this glycosylation, thioglycoside 6 was first activated with BSP and triflic anhydride in the presence of a hindered base to give an $\alpha$-anomeric triflate intermediate, which upon addition of sugar alcohol 7, was displaced to provide a $\beta$-mannoside. The anomeric TDS group of 8 was removed by treatment with HF in pyridine to give lactol 9, which was converted into a trifluoro-N-phenylimidate 10 by treatment with N-phenyltrifluoroacetimidoyl chloride in the presence of DBU. A TfOH mediated glycosylation (Schmidt, 1986 Angew. Chem. Int. Ed. Engl. 25:212-235) of 10 with 11 gave trisaccharide 12 in an excellent yield as only the β-anomer. Next, the NAP ether was removed by oxidation with DDQ in a mixture of DCM and water and the resulting alcohol 13 was coupled with glycosyl donor 14 using TfOH as the activator resulting in the formation of tetrasaccharide 15 in high yield. The benzylidene acetal of 15 was regioselectively opened using triethylsilane and PhBCl$_2$ to provide glycosyl acceptor 16, which was coupled with 17 using standard conditions to provide target compound 1.

Scheme 1. Synthesis of orthogonally protected core pentasaccharide 1.

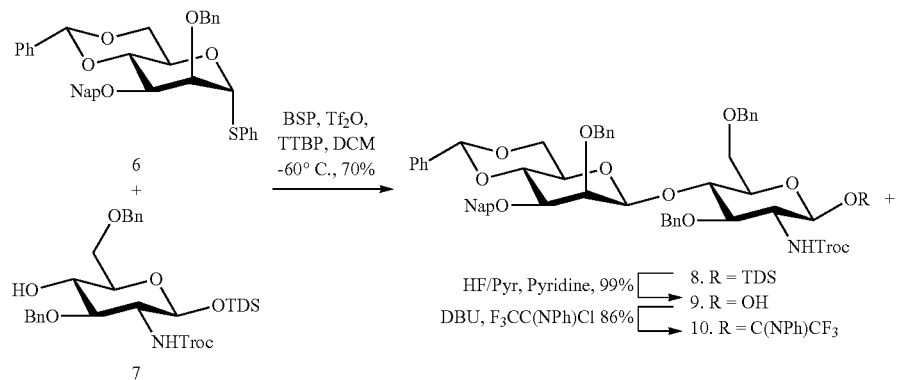

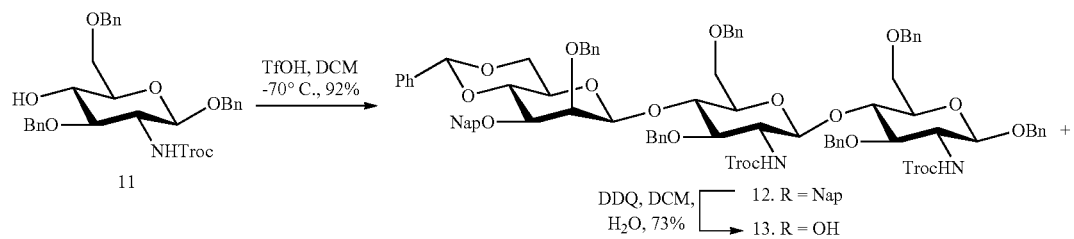

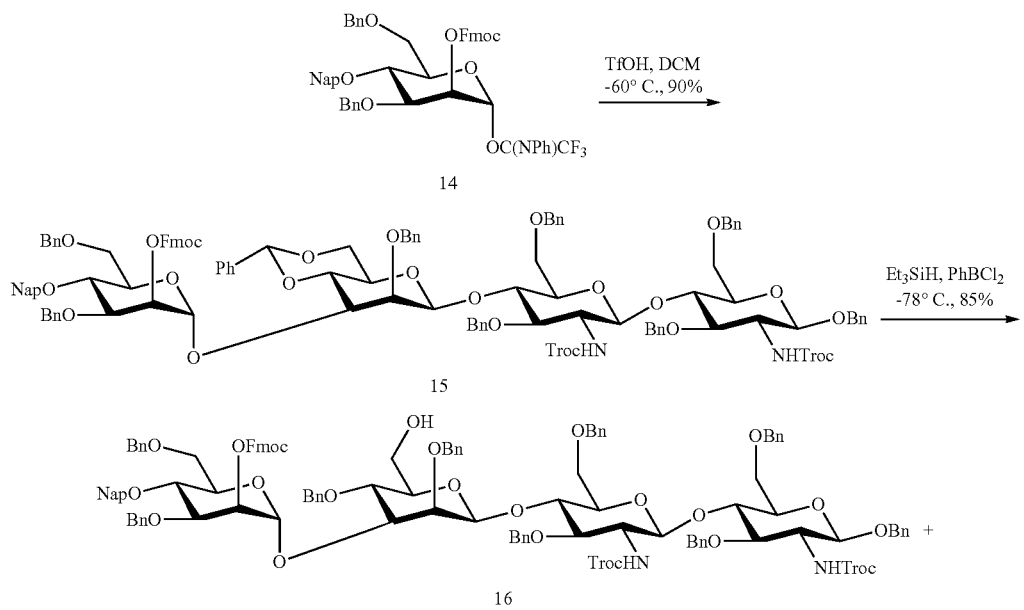

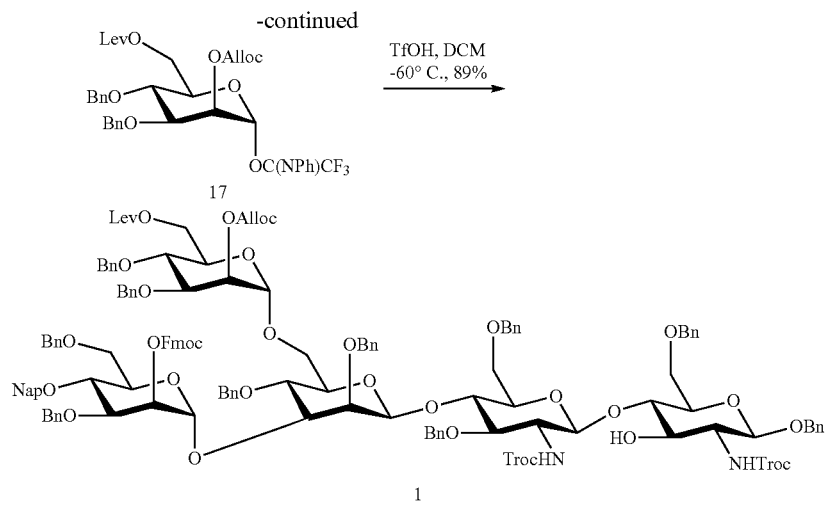

Next, the orthogonality of the four temporary protecting groups of 1 was examined (Scheme 2). Thus, the Fmoc group of 1 could be selectively removed by employing the hindered base $Et_3N$ in DCM resulting in the clean formation of compound 18. Compound 19 was isolated in high yield by oxidation of the Nap ether of 1 with DDQ in a mixture of DCM and water (Gaunt et al., 1998 J. Org. Chem. 63:4172-4173). The Alloc functionality of 1 could be readily cleaved by treatment with $Pd(PPh_3)_4$ (Tsukamoto et al., 1997 Biosci. Biotechnol. Biochem. 61:1650-1657) to give compound 20 and finally, treatment of 1 with the nucleophilic base hydrazine acetate in DCM (Zhu and Boons, 2000 Tetrahedron: Asymmetry 11:199-205; Zhu and Boons, 2001 Chem. Eur. J. 7:2382-2389) resulted in cleavage of the Lev ester without affecting the other protecting groups providing pentasaccharide 21 in a yield of 85%.

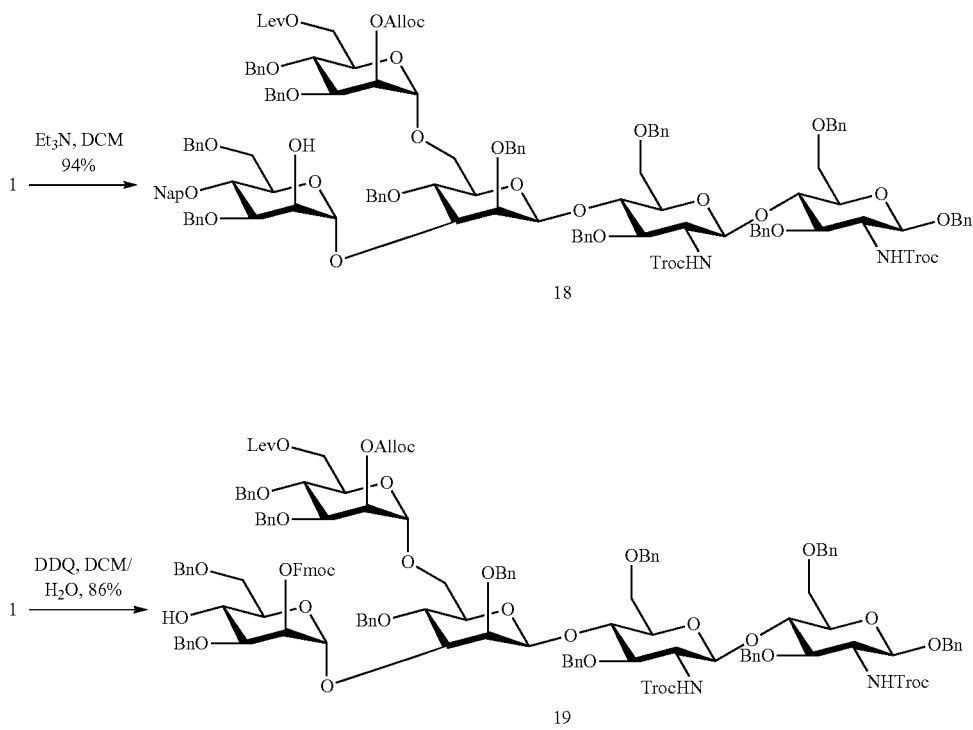

Scheme 2. Versatility of core pentasacchride (1)-Deprotection of Orthogonal groups (Fmoc, Nap, Alloc and Lev)

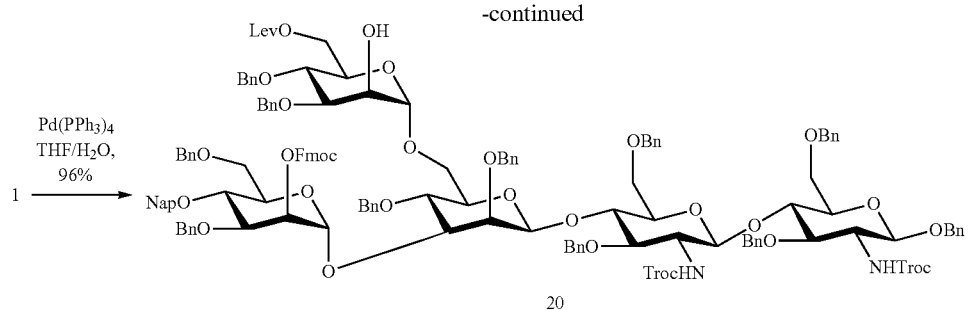

Having demonstrated the orthogonality of the temporary protecting groups, attention was focused on the preparation of tri-antennary oligosaccharides 27 (Scheme 3) and 32 (Scheme 4). Thus, glycosyl acceptor 18 was coupled with O-benzylated LacNAc donor 2 using TfOH as the promoter to give heptasaccharide 22 in a yield of 97%. The NAP ether of 22 was removed by treatment with DDQ in a mixture of DCM and water the hydroxyl of the resulting acceptor 23 was coupled with partially acetylated glycosyl donor 3 to afford 24. The next step of the assembly entailed the removal of the Lev ester of 24 by treatment with hydrazine acetate in DCM and the hydroxyl of the resulting compound 25 was coupled with GlcNAc donor 4 using standard activation conditions to provide decasaccharide 26. Partial deprotection of the latter compound was easily accomplished by a four-step procedure to give target compound 27 and entailed removal of the Troc groups with Zn in acetic acid, acetylation of the resulting free amines with acetic anhydride in methanol, cleavage of the Alloc function by treatment with Pd(PPh$_3$)$_4$ (Tsukamoto et al., 1997 Biosci. Biotechnol. Biochem. 61:1650-1657) and finally catalytic hydrogenolysis of the benzyl ethers.

Scheme 3. Synthesis of Decasacchride 27 by the sequential removal of orthogonal protecting groups of pentasacchride 18, followed by glycosylations with donors 2-4.

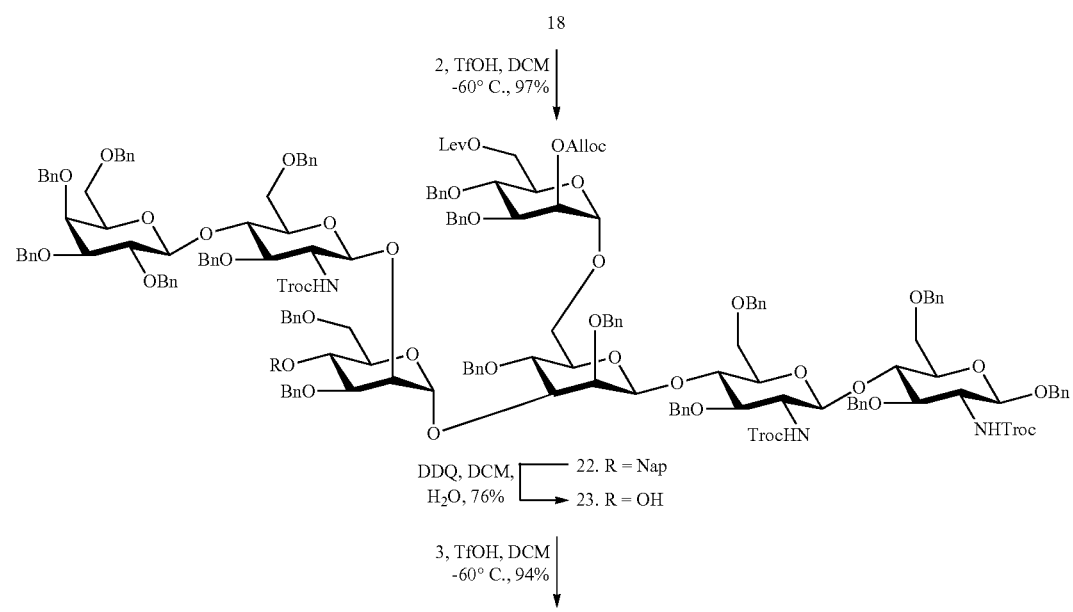

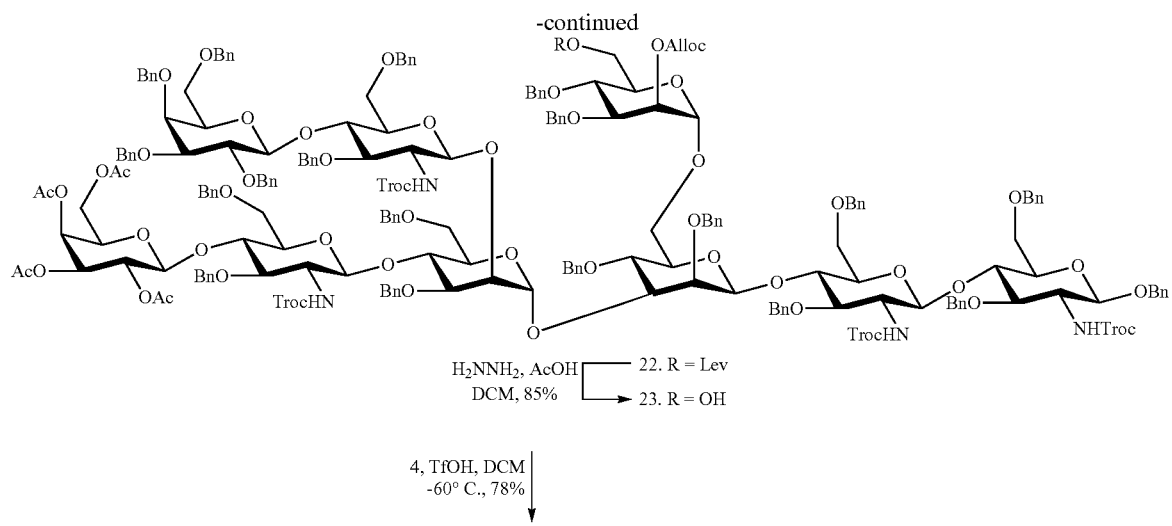
-continued
22. R = Lev
H₂NNH₂, AcOH
DCM, 85%
→ 23. R = OH
4, TfOH, DCM
-60° C., 78%
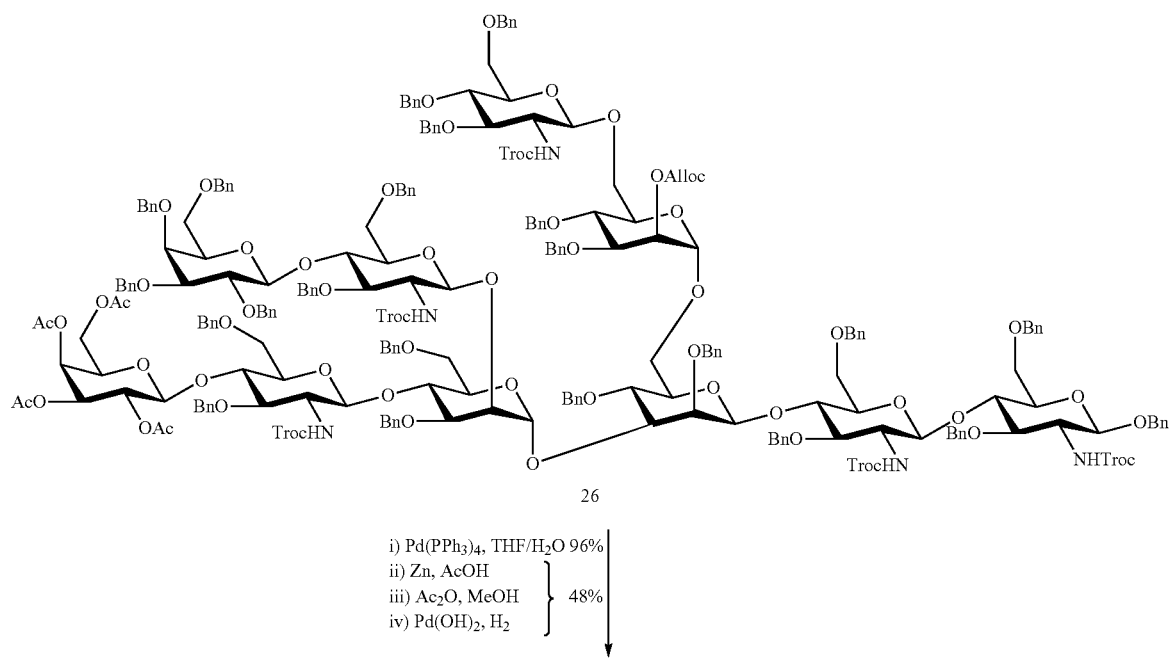
26
i) Pd(PPh₃)₄, THF/H₂O 96%
ii) Zn, AcOH
iii) Ac₂O, MeOH  } 48%
iv) Pd(OH)₂, H₂
27

Decasaccharide 32 could be prepared by a similar strategy starting from compound 22. In this case, the Alloc protecting group was removed using Pd(PPH₃)₄ and the resulting acceptor 28 was glycosylated with 3 using standard conditions to provide nonasaccharide 29. Next, the Lev ester of 29 was cleaved with hydrazine acetate to give compound 30, which was coupled with 4, to give fully protected decasaccharide 31. Partial deprotection of 31 to give target compound 32 was accomplished by treatment with Zn in acetic acid to remove the Troc functions, acetylation of the resulting free amines with acetic anhydride in methanol and catalytic hydrogenolysis of the 2-naphtyl methyl ether and the benzyl ethers.

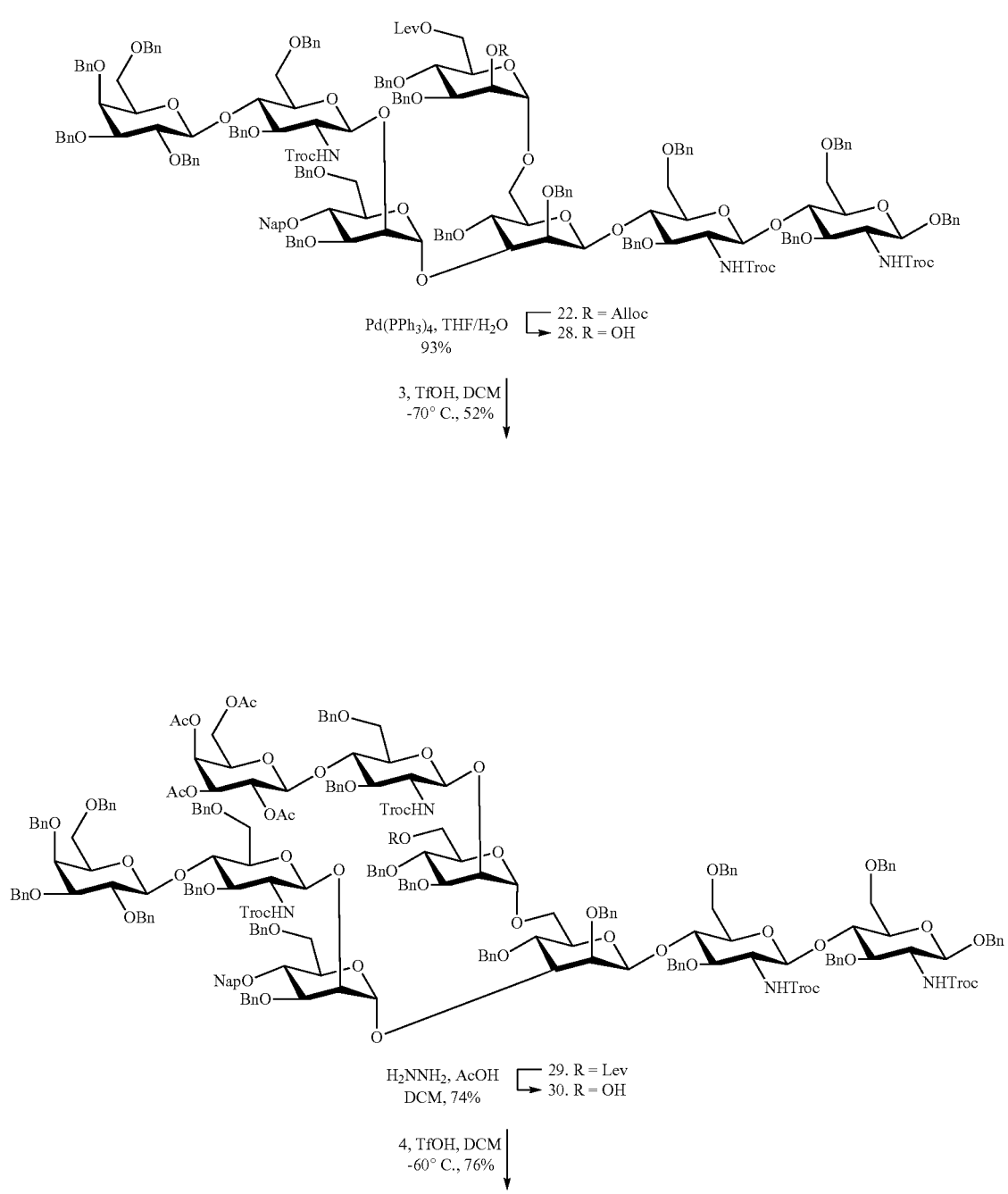

Scheme 4. Synthesis of Decasacchride 32 by the sequential removal of orthogonal protecting groups of Heptasacchride 22, followed by glycosylations with donors 3,4.

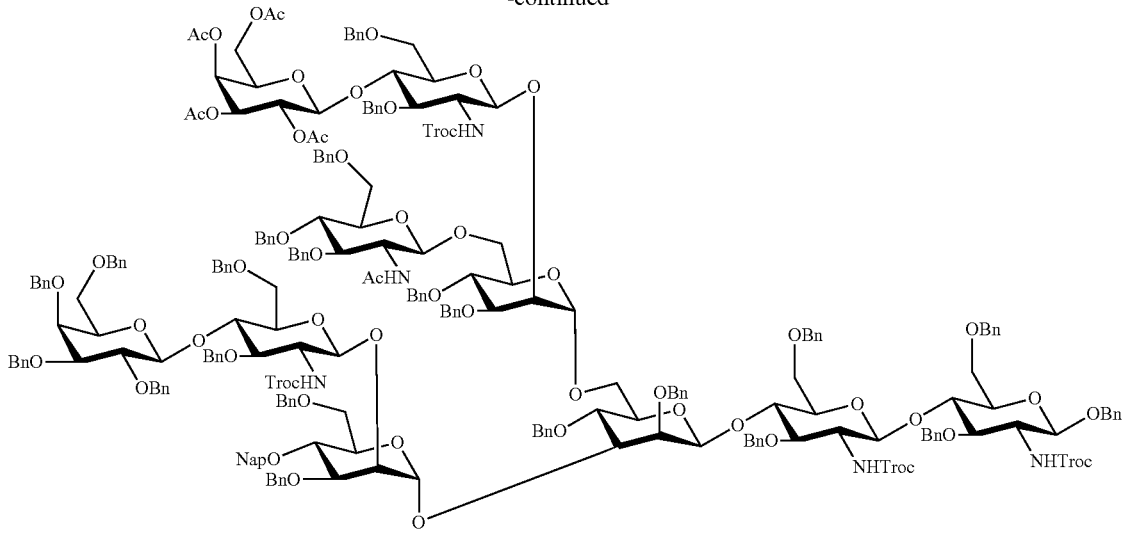

31 i) Zn, AcOH  
ii) Ac₂O, MeOH } 49%  
iii) Pd(OH)₂, H₂  90%

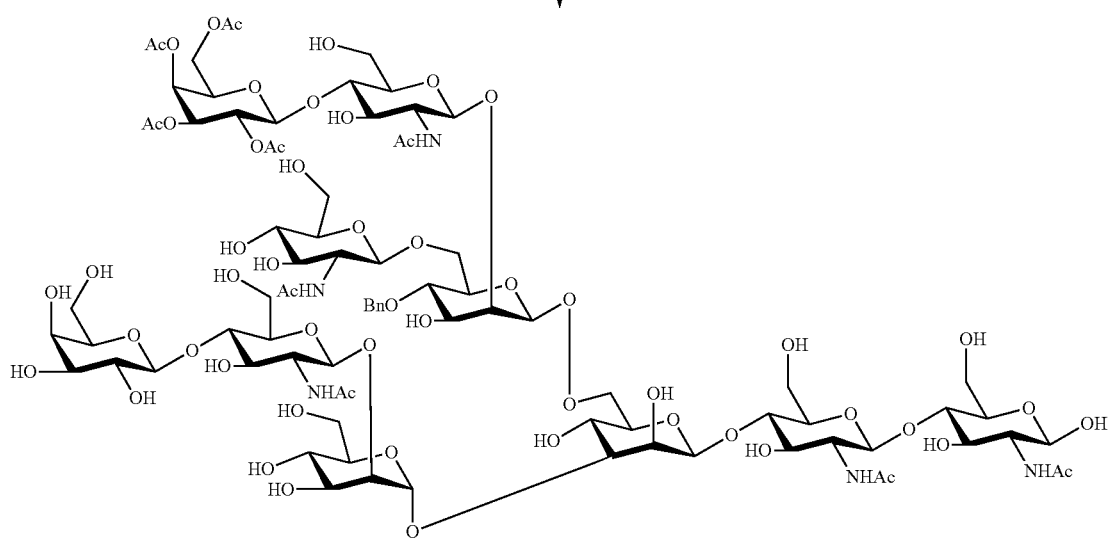

32

Enzymatic modifications to provide asymmetrically substituted N-glycans.

Figure 3:
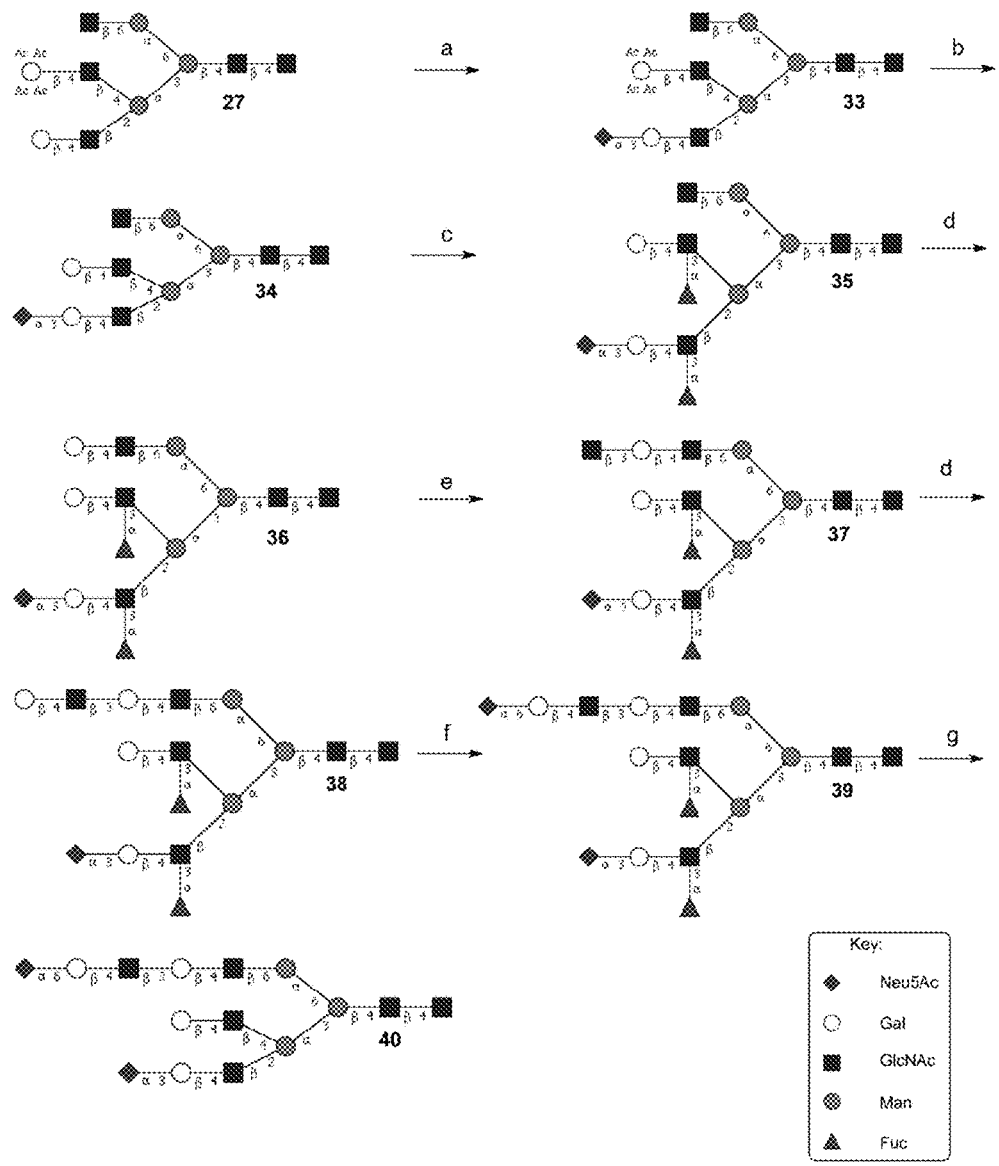
FIG. 3 shows Scheme 5, enzymatic modifications of decasaccharide 27 to form various asymmetrical glycans; a) rST3Gal-III, CMP-Neu5Ac; b) NH$_4$OH, H$_2$O; c) HPα1-3FucT, GDP-Fuc; d) GalT-1, UDP-Gal; e) HP-39(β1-3GlcNAcT), UDP-GlcNAc; f) ST6Gal-I, CMP-Neu5Ac; g) α1-3,4Fucosidase.
Figure 4:
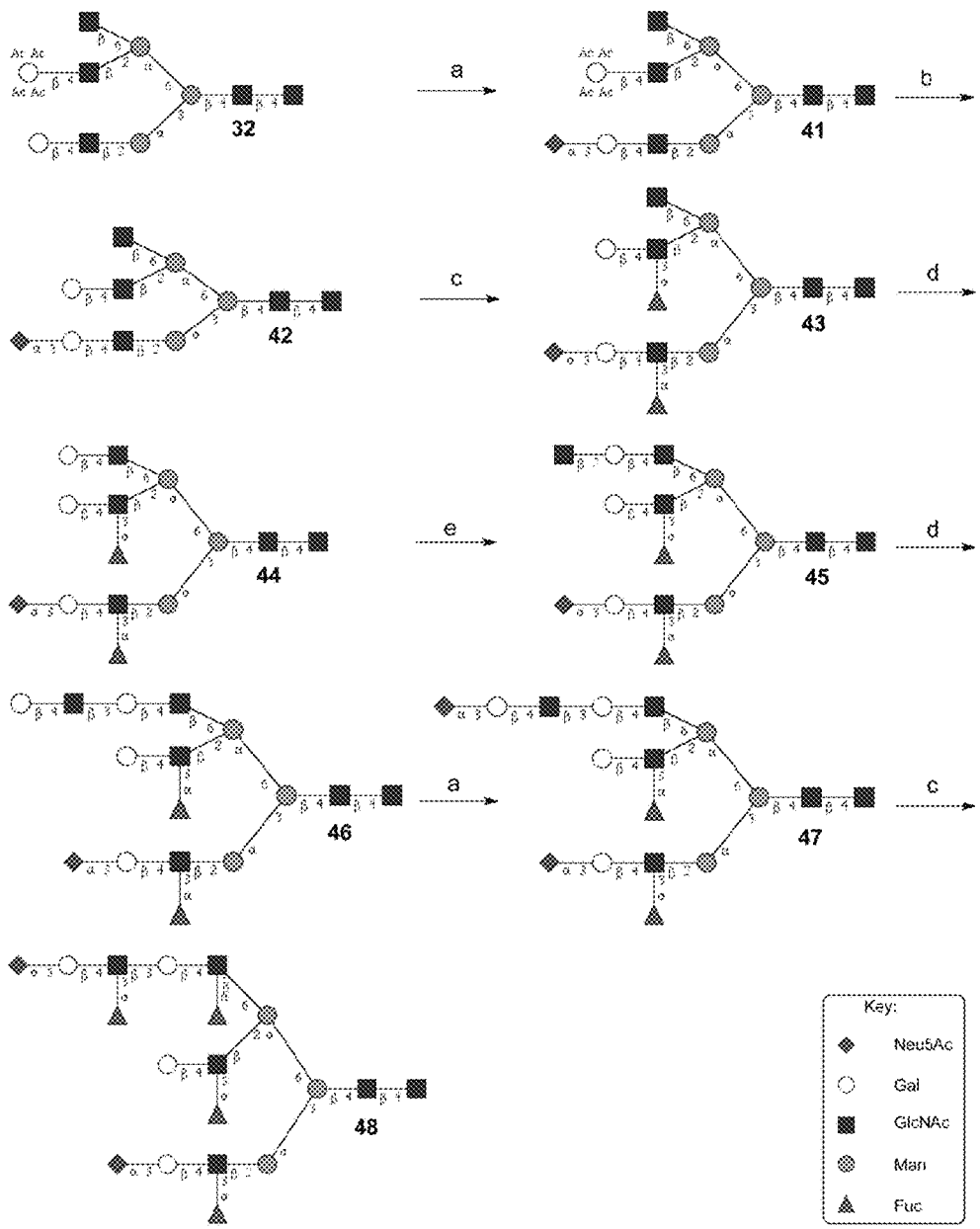
FIG. 4 shows Scheme 6, enzymatic modifications of decasaccharide 32 to form asymmetrically substituted glycans; a) rST3Gal-III, CMP-Neu5Ac; b) NH$_4$OH, H$_2$O; c) HPα1-3FucT, GDP-Fuc; d) GalT-1, UDP-Gal; e) HP-39(β1-3GlcNAcT), UDP-GlcNAc.

The "precursor" oligosaccharides 27 (Scheme 5; FIG. 3) and 32 (Scheme 6; FIG. 4) were employed for further extension by glycosyl transferases. Thus, the LacNAc moiety of decasaccharide 27 was selectively sialylated by using rST3Gal-III, CMP-Neu5Ac and Calf Intestine Alkaline Phosphatase (CIAP) to give compound 33. This enzyme did not modify the acetylated LacNAc arm and terminal GlcNAc moiety. Next, the acetyl moieties of 33 were removed by treatment with aqueous ammonia and treatment of the resulting compound 34 with α1,3-fucosyltransferase (α3FucT) resulted in fucosylation of the LacNAc and sialyl-LacNAc arms providing bis-fucosylated derivative 35. The GlcNAc moiety at the C-6 antenna was extended to a LacNAc moiety by employing β1-4-galactosyltransferase (GalT-1), UDP-Gal and CIAP to give 36. Treatment of 36 with β1-3-N-acetylglucosaminyltransferase (β1-3Glc-NAcT), UDP-GlcNAc and CIAP resulted in selective addition of a β(1-3) linked GlcNAc moiety to the LAcNAc arm and importantly the Le$^x$ arm of compound was unaffected by this enzyme. The β1-6 branch was further extended by the action of GalT-1 and ST6Gal-1 to provide compound 39, which has a unique oligosaccharide structure at each of the three antennae. The compound can be remodeled by glycosidases and for example treatment of 39 with α1-3,4-Fucosidase gave compound 40. In this approach, the fucosides served as a blocking group to allow selective extension of the C-6 antenna. After each step, the compound was purified by size exclusion chromatography over Sephadex G-25 and the resulting compound characterized by NMR, Mass spectrometry and methylation analysis. These analyses demonstrated homogeneity of all compounds.

Compounds 41-48 were prepared starting from precursor decasaccharide 32. Thus, 32 was sialylated using rST3Gal-III to provide 41, which was deacetylated to provide 42 which was further extended respectively by α1-3FucT, β1-44GalT, β1-3GlcNAcT, β1-4GalT, rST3Gal-III and finally α1-3FucT to give 48.

Figure 5:
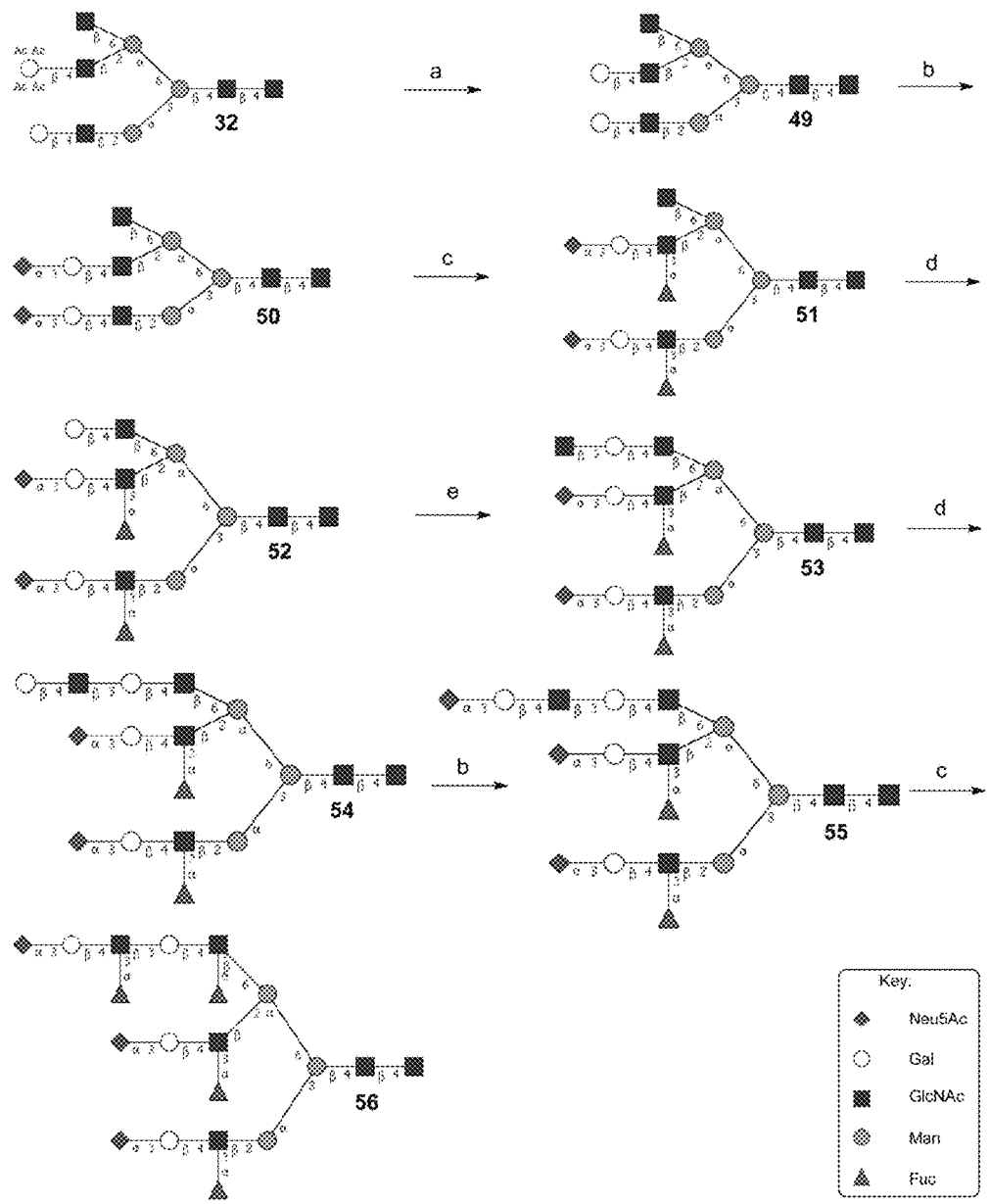
FIG. 5 shows Scheme 7, enzymatic modifications of decasaccharide 32 to form eicosasaccharide 56; a) NH$_4$OH, H$_2$O; b) rST3Gal-III, CMP-Neu5Ac; c) HPα1-3FucT, GDP-Fuc; d) GalT-1, UDP-Gal; e) HP-39(β1-3GlcNAcT), UDP-GlcNAc.

Compounds 27 and 32 could also be employed to make tri-antennary structures that have two different arms. For example, compound 56, which has been found on the human oocytes (Pang eta 1, 2011 Science 333:1761-1764) was synthesized by deacetylation of 32 to give 50, which was further extended, respectively by rST3Gal-III, α1-3FucT, β1-4GalT, β1-3GlcNAcT, β1-4GalT, rST3Gal-III and finally α1-3FucT (Scheme 7; FIG. 5).

Example 2. Experimental Procedures

Chemical Syntheses

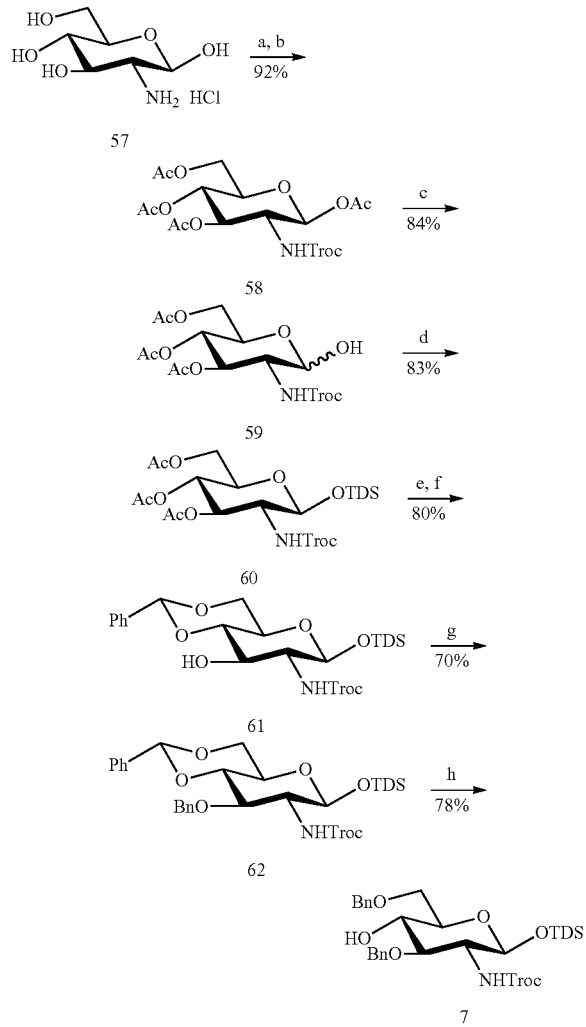

Reagents: a) TrocCl, NaHCo$_3$/H$_2$O, rt, 5 h; b) Ac$_2$O, pyridine, rt, overnight;
c) Hydrazine acetate, DMF, rt, overnight; d) TDSCl, imidazole, DMF, rt, 16 h;
e) NaOMe, Guanidine hydrochloride, MeOH/DCM, rt, 40 mins;
f) PhCH(OMe)$_2$, CSA, CH$_3$CN, rt, 2 h; g) BnBr, Ag$_2$O, MS-4Å, rt, 30 h;
h) Et$_3$SiH/TfOH, DCM, -78° C., 1 h A solution of β-D-glucosamine 57 (40 g, 186 mmol) and solid NaHCO$_3$ (46.8 g, 558 mmol) were put into H$_2$O (360 mL). The mixture was vigorously stirred at room temperature for 30 min and then 2,2,2-Trichloroethyl chloroformate (30 mL, 223 mmol) was added dropwise to the solution over a period of 30 min. The mixture was stirred at room temperature for another 4 h and filtered to give a yellowish solid. The resulting solid (54 g, 150 mmol) was dissolved in pyridine (200 mL) and then cooled down to 0° C., followed by slow addition of acetic anhydride (88 ml, 900 mmol). The mixture was stirred at room temperature overnight and quenched by ethanol (100 mL) at 0° C. The mixture was stirred at room temperature overnight and was concentrated. The resulting residue was diluted with EtOAc (500 mL) and then washed with saturated aqueous solution of NaHCO$_3$, 10% of HCl, water and then dried over Na$_2$SO$_4$, filtered and concentrated to dryness under vacuo without further purification. The obtained solid 58 (60 g, 115 mmol) was dissolved in DMF (300 mL) and hydrazine acetate (11.6 g, 127 mmol) was added. The mixture was stirred at room temperature overnight and then concentrated to dryness. The resulting residue was diluted with EtOAc (500 mL) and then washed with saturated aqueous solution of NaHCO$_3$ and water. The organic phase was dried over Na$_2$SO$_4$, filtered and concentrated to dryness. Silica gel column chromatography (3:2 hexanes-EtOAc) afforded compound 59 (46.3 g, 84%). 59 (29 g, 60.3 mmol), Chloro(dimethyl)thexylsilane (17.8 mL, 90.5 mmol), imidazole (8.2 g, 120.6 mmol) were dissolved in DMF (150 mL). The mixture was stirred at room temperature for 16 h and then concentrated to dryness. The resulting residue was diluted with EtOAc (500 mL) and then washed with saturated aqueous NH$_4$Cl and then dried over Na$_2$SO$_4$, filtered and the solvents were removed in vacuum. Silica gel column chromatography (3:2 hexanes-EtOAc) afforded compound 60 as white solid (31.2 g, 83%). Compound 60, NaOCH$_3$, and Guanidine chloride (0.1 M, 200 mL) were stirred at room temperature for 40 min under N$_2$ and then was neutralized with Amberlite IR-120 and concentrated to dryness. The resulting residue (31.5 g, 63.4 mmol), benzaldehyde dimethyl acetal (10.47 mL, 69.7 mmol) and camphorsulfonic acid (3 g, 12.7 mmol) in anhydrous CH$_3$CN (200 mL) was stirred at room temperature for 2 h and then the reaction was quenched by Et$_3$N. The reaction mixture was diluted with EtOAc (500 mL) and washed with a saturated aqueous solution of NaHCO$_3$, water and then dried over Na$_2$SO$_4$, filtered and concentrated. Silica gel column chromatography (3:1 hexanes-EtOAc) afforded 61 as white solid (29.8 g, 80%). $^1$H-NMR (500 MHz, CDCl$_3$): δ 0.00-0.01 (m, 6H, TDS), 0.70-0.74 (m, 12H, TDS), 1.46-1.49 (m, 1H, TDS), 3.05 (br, 1H, 3-OH), 3.20-3.30 (m, 2H, H-2, H-4), 3.40 (t, 1H, J=9.5 Hz, H-6b), 3.60 (t, 1H, J=9.5 Hz, H-6a), 3.78-3.81 (m, 1H, H-5), 4.13 (dd, 1H, J=10.5 Hz, 5.0 Hz, H-3), 4.51-4.63 (m, 3H, NH, 2Troc), 4.97 (d, 1H, J=7.5 Hz, H-1), 5.37 (s, 1H, PhCH), 7.22-7.27 (m, 3H), 7.35-7.37 (m, 2H); $^{13}$C-NMR (75 MHz, CDCl$_3$): δ −3.4, −1.9, 18.5, 18.6, 20.0, 24.8, 34.0, 60.7, 66.2, 68.6, 70.8, 74.9, 81.5, 95.2, 96.2, 101.9, 126.5, 128.4, 129.4, 137.1, 154.5.

Compound 61 (26 g, 44.5 mmol) was dissolved in DCM (200 mL). To this solution, acid washed 4 Å molecular sieve, Benzyl bromide (13.2 mL, 0.11 mol) and freshly prepared Silver (II) oxide (20.6 g, 2 eq, 89 mmol) were added at room temperature. The reaction was protected from light and stirred at room temperature for 30 hours at which point it was filtered through Celite to remove the Silver (II) oxide and concentrated. Silica gel chromatography (4:1 hexanes-EtOAc) afforded compound 62 (21 g, 70%). $^1$H-NMR (500

MHz, CDCl$_3$): δ 0.00-0.03 (m, 6H, TDS), 0.72-0.76 (m, 12H, TDS), 1.47-1.52 (m, 1H, TDS), 3.18-3.23 (m, 1H, H-4), 3.32-3.36 (m, 1H, H-2), 3.60-3.70 (m, 2H, H-6a, H-6b), 4.18 (dd, 1H, J=10.5 Hz, 5.0 Hz, H-3), 4.50-4.56 (m, 2H, Troc), 4.57 (d, 1H, J=12.0 Hz, Bn), 4.78 (d, 1H, J=12.0 Hz, Bn), 4.81 (d, 1H, J=7.5 Hz, H-1), 4.92 (br, 1H, NH), 5.46 (s, 1H, PhCH), 7.13-7.20 (m, 5H), 7.24-7.30 (m, 3H), 7.37-7.39 (m, 2H); $^{13}$C-NMR (75 MHz, CDCl$_3$): δ −3.4, −1.8, 18.5 (×2), 20.0 (×2), 24.8, 34.0, 60.1, 66.0, 68.8, 74.3, 74.6, 76.4, 82.7, 95.4, 95.9, 101.2, 126.1, 127.8, 128.2, 128.3, 128.4, 129.0, 137.4, 138.2, 153.8.

Compound 62 (6.0 g, 8.9 mmol) was dissolved in DCM (200 mL) and the solution was cooled down to −78° C., followed by sequential addition of Triethylsilane (4.54 mL, 28.5 mmol) and TfOH (2.3 mL, 25.8 mmol). The mixture was stirred at −78° C. for 1 h and then quenched by MeOH/Et$_3$N (5 mL/each). The resulting mixture was washed by saturated aqueous NaHCO$_3$ and H$_2$O and concentrated. Silica gel chromatography (4:1 hexanes-EtOAc) afforded compound 7 (4.7 g, 78%). $^1$H-NMR (500 MHz, CDCl$_3$): δ 0.00-0.04 (m, 6H, TDS), 0.71-0.75 (m, 12H, TDS), 1.46-1.52 (m, 1H, TDS), 3.00 (br, 1H, 4-OH), 3.22-3.31 (m, 2H, H-6b), 3.54-3.58 (m, 4H, H-3, H-4, H-5, H-6a), 3.40-3.47 (m, 2H, Troc), 4.51-4.66 (m, 5H, H-1, Bn), 5.01-5.03 (br, 1H, NH), 7.13-7.22 (m, 10H); $^{13}$C-NMR (75 MHz, CDCl$_3$): δ−3.5, −1.9, 18.4, 18.5, 19.9, 20.0, 24.7, 33.9, 59.0, 70.3, 72.3, 73.5, 74.0, 74.4, 80.4, 95.3, 95.5, 127.5, 127.6, 127.7, 127.9, 128.3, 128.4, 137.8, 138.3, 153.9.

Compound 62 (5 g, 7.4 mmol) was dissolved in pyridine (70 mL). The mixture was cooled to 0° C., followed by addition of HF (35 mL, 65-70% in pyridine). The mixture was stirred at room temperature overnight and then was diluted in EtOAc (200 mL), washed with 10% of CuSO$_4$, saturated aqueous NaHCO$_3$ and H$_2$O. The organic layer was dried over Na$_2$SO$_4$, filtered and concentrated. Silica gel column chromatography (6:1 hexane-EtOAc) afforded compound 63 as a white solid (3.84 g, 97%). Compound 63 (1.9 g, 3.57 mmol), Cl$_3$CCN (7.15 mL, 71.4 mmol) and DCM (100 mL) was cooled down to 0° C. DBU (0.11 mL, 0.71 mmol) was added and the mixture was stirred at room temperature for 1 h. The mixture was concentrated. Silica gel column chromatography (6:1 hexanes-EtOAc) afforded the corresponding imidate 64 (1.47 g, 61%) as a white solid. The imidate 64 (1.47 g, 2.17 mmol), Benzyl alcohol (0.45 mL, 4.34 mmol), molecular sieve MS-4 Å and DCM (100 mL) was stirred at room temperature for 30 min. The mixture was cooled to −70° C., followed by addition of TfOH (38 µL, 0.43 mmol). The reaction mixture was stirred for 1 hour from −70 to −20° C. and at −60° C. and then was quenched with Triethylamine (0.2 mL). The mixture was diluted with DCM (300 mL), washed with a saturated aqueous solution of NaHCO$_3$, H$_2$O and then dried over Na$_2$SO$_4$, filtered and concentrated. Silica gel column chromatography (5:1:1 hexanes-EtOAc-DCM) afforded 65 as a white solid (1 g, 74%). $^1$H-NMR (500 MHz, CDCl$_3$): δ 3.45-3.52 (m, 2H, H-2, H-4), 3.76-3.89 (m, 2H, H-6a, H-6b), 4.00-4.04 (m, 1H, H-5), 4.41 (dd, 1H, J=10.0, 3.6 Hz, H-3), 4.62 (d, 1H, J=12.0 Hz, Bn), 4.70-4.76 (m, 1H, Bn, Troc), 4.81 (d, 1H, J=8.0 Hz,), 4.91-4.94 (m, 2H, Bn), 5.06 (br, 1H, NH), 5.63 (s, 1H, PhCH), 7.29-7.45 (m, 13H), 7.52-7.54 (m, 2H); $^{13}$C-NMR (75 MHz, CDCl$_3$): δ 58.1, 66.1, 68.8, 71.2, 74.5, 76.5, 82.6, 85.1, 99.8, 101.3, 126.0, 127.9, 128.0, 128.3 (×2), 128.4, 128.5, 129.1, 136.9, 137.3, 138.0, 153.9.

Compound 65 (1 g, 1.6 mmol) was dissolved in DCM (100 mL) and the solution was cooled down to −78° C., followed by sequential addition of Triethylsilane (0.82 mL, 5.1 mmol) and TfOH (0.41 mL, 4.7 mmol). The mixture was stirred at −78° C. for 1 h and then quenched by MeOH/Et$_3$N (1 mL/each). The resulting mixture was washed by saturated aqueous NaHCO$_3$ and H$_2$O and concentrated. Silica gel chromatography (4:1:1 hexanes-EtOAc-DCM) afforded compound 11 (0.92 g, 92%). $^1$H-NMR (500 MHz, CDCl$_3$): δ 2.81 (br, 1H, 4-OH), 3.44-3.52 (m, 2H, H-2, H-4), 3.74-3.84 (m, 4H, H-3, H-5, H-6a, H-6b), 4.60-4.71 (m, 6H, H-1, Bn), 4.78-4.80 (m, 2H, Troc), 4.90 (d, 1H, J=12 Hz, Bn), 5.09 (br, 1H, NH), 7.25-7.42 (m, 15H); $^{13}$C-NMR (75 MHz, CDCl$_3$): δ 57.4, 70.5, 70.7, 73.1, 73.7, 73.8, 74.3, 74.5, 80.5, 99.2, 127.8, 127.9 (×2), 128.1, 128.4, 128.5, 128.6, 137.2, 137.7, 138.2, 154.0.

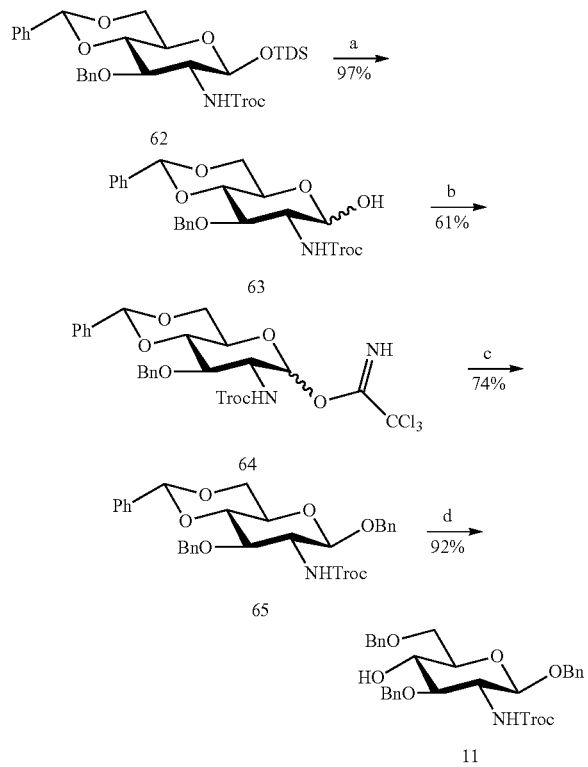

Scheme 9. Synthesis of Glucoamine acceptor 11.

Reagents: a) HF/pyridine, pyridine, rt, overnight; b) Cl$_3$CCN, DBU, DCM, rt, 1 h; c) BnOH, TfOH, DCM, MS-4Å, -70 to -20° C., 1 h; d) Et$_3$S$^i$H/TfOH, DCM, -78° C., 1 h

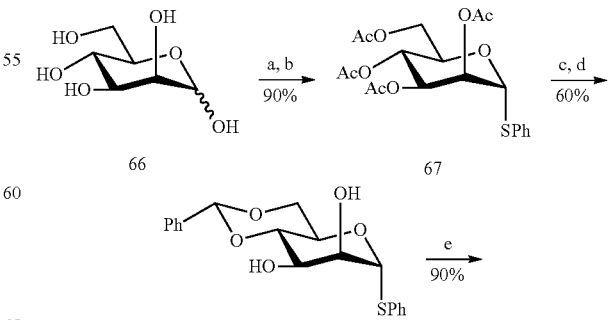

Scheme 10. Synthesis of Mannose donor 6.

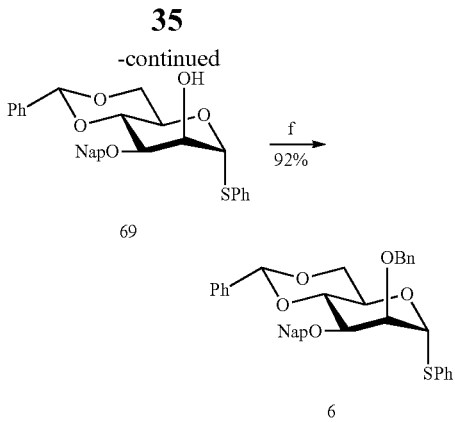

Reagents: a) Ac₂O, pyridine, rt, overnight; b) PhSH, BF₃ etherate, DCM, rt, 20 h; c) NaOMe, MeOH, rt, 4 h; d) PhCH(OMe)₂, CSA, DMF, 70° C., overnight; e) Bu₂SnO, Toluene, reflux, 3 h, then NapBr, CsF, DMF, rt, overnight; f) NaH, BnBr, DMF, rt, 2 h A solution of β-D-mannose 66 (20 g, 0.11 mol) in pyridine (250 mL) was cooled down to 0° C., followed by slow addition of acetic anhydride (105 ml, 1.1 mol). The mixture was stirred at room temperature overnight and quenched by ethanol (100 mL) at 0° C. The mixture was concentrated and then diluted with DCM (500 mL). The resulting solution was washed with saturated aqueous solution of $NaHCO_3$, 10% of HCl, water and then dried over $Na_2SO_4$, filtered and concentrated to dryness under vacuo without further purification. The obtained solid and thiophenol (13.9 ml, 0.13 mol) were dissolved in DCM (250 mL). The mixture was cooled down to 0° C., followed by addition of boron trifluoride diethyl etherate (42 ml, 0.33 mol). The mixture was stirred at room temperature for 20 h and diluted with dichloromethane (200 mL). The resulting solution was washed with saturated aqueous solution of $NaHCO_3$ and water and then dried over $Na_2SO_4$, filtered and concentrated to dryness. Silica gel column chromatography (3:2 hexanes-EtOAc) afforded compound 67 as white solid (44 g, 90% for 2 steps). Compound 67 (36 g, 81.7 mmol) was dissolved in methanol (500 mL) and then sodium (0.94 g, 41 mmol) was added in portions and the mixture was stirred for 4 hours at room temperature and was neutralized with Amberlite IR-120 until the pH was around 7 and then filtered, concentrated and dried under vacuum. The resulting residue, benzaldehyde dimethylacetal (8.1 mL, 0.13 mol) and camphorsulfonic acid (2.3 g, 9.8 mmol) in anhydrous DMF (100 mL) was stirred at 70° C. overnight and then the reaction was quenched by Et₃N. The reaction mixture was diluted with DCM (500 mL) and washed with saturated aqueous solution of $NaHCO_3$, water and then dried over $Na_2SO_4$, filtered and concentrated. Silica gel column chromatography (4:1 hexanes-EtOAc) afforded 68 as white solid (10.6 g, 60%). Compound 68 (5.85 g, 16.2 mmol), di-butyltin oxide (4.24 g, 17 mmol) and toluene (110 mL) were refluxed for 3 h, followed by removal of solvents under vacuo. The mixture of the resulting solid, cesium fluoride (2.59 g, 16.2 mmol), 2-(bromomethyl)naphthalene (3.77 g, 16.2 mmol) and DMF (50 mL) was stirred at room temperature overnight. DMF was removed by vacuum and the mixture was diluted with DCM (200 mL). The mixture was washed with saturated aqueous solution of $NaHCO_3$, water and then dried over $Na_2SO_4$, filtered and concentrated. Silica gel column chromatography (3:1 hexanes-EtOAc) afforded compound 69 as white solid (7.3 g, 90%). ¹H-NMR (500 MHz, CDCl₃): δ 3.11 (br, 1H, 2-OH), 3.91 (t, 1H, J=10.0 Hz, H-6b), 4.06 (dd, 1H, $J_{3,4}$=10.0 Hz, $J_{2,3}$=3.0 Hz, H-3), 4.25-4.29 (m, 2H, H-6a, H-4), 4.35-4.42 (m, 2H, H-2, H-5), 4.95 (d, 1H, J=12.0 Hz, Nap), 5.06 (d, 1H, J=12.0 Hz, Nap), 5.64 (br, 1H, H-1), 5.68 (s, 1H, PhCH), 7.29-7.35 (m, 3H), 7.42-7.59 (m, 10H), 7.79-7.81 (m, 1H), 7.86-7.89 (m, 3H); ¹³C-NMR (75 MHz, CDCl₃): δ 64.6, 68.5, 71.3, 73.1, 75.7, 78.9, 87.8, 101.7, 125.6, 126.1 (×2), 126.2, 126.7, 127.6, 127.7, 127.9, 128.2, 128.3, 129.0, 129.1, 131.7, 133.1, 133.2 (×2), 135.1, 137.4. gHMQC (without ¹H decoupling): $^1J_{C1,H1}$=170.0 Hz.

69 (7.0 g, 14 mmol) was dissolved in DMF (100 mL) and the solution was cooled to 0° C. NaH (0.67 g, 60% NaH in mineral oil, 16.8 mmol) was added in portions, followed by addition of Benzyl bromide (1.99 mL, 16.8 mmol). The mixture was stirred at room temperature under N₂ overnight for 2 h and then the solvent was removed under vacuum. The mixture was diluted with EtOAc (200 mL) and washed with saturated $NaHCO_3$, water, and then the organic layer was dried over $Na_2SO_4$, filtered and concentrated. Silica gel column chromatography (8:1 hexane-EtOAc) afforded compound 6 as a white solid (7.6 g, 92%). ¹H-NMR (600 MHz, CDCl₃): δ 4.02 (t, 1H, J=8.0 Hz, H-6b), 4.18 (dd, 1H, $J_{3,4}$=8.0 Hz, $J_{2,3}$=3.0 Hz, H-3), 4.21-4.44 (m, 1H, H-2), 4.35-4.38 (m, 1H, H-6a), 4.43-4.47 (m, 1H, H-5), 4.51 (t, 1H, J=8.0 Hz, H-4), 4.85 (br, 2H, Nap), 4.93 (d, 1H, J=10.0 Hz, Bn), 5.07 (d, 1H, J=10.0 Hz, Bn), 5.67 (d, 1H, J=1.0 Hz, H-1), 5.79 (s, 1H, PhCH), 7.34-7.44 (m, 6H), 7.47-7.52 (m, 7H), 7.55-7.58 (m, 3H), 7.68-7.69 (m, 2H), 7.83-7.85 (m, 1H), 7.90-7.94 (m, 3H); ¹³C-NMR (125 MHz, CDCl₃): δ 65.4, 68.4, 72.8, 72.9, 76.1, 77.9, 78.9, 86.9, 101.5, 125.5, 125.7, 125.9, 126.1 (×2), 127.5 (×2), 127.7, 127.8, 128.0, 128.1, 128.3, 128.8, 129.0, 131.5, 132.8, 133.2, 133.6, 135.7, 137.5, 137.6.

Scheme 11. Synthesis of Disaccharide 8.

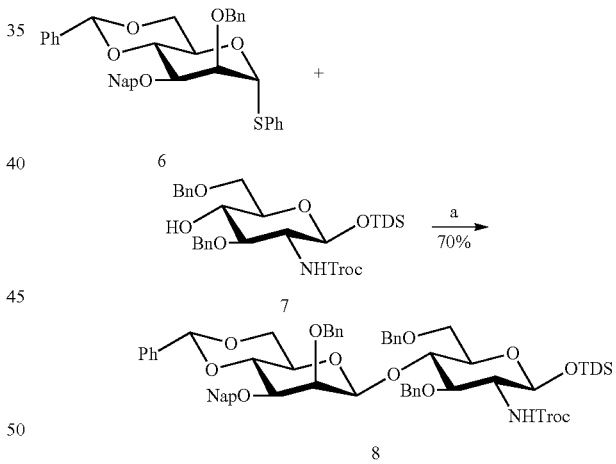

Reagents: a) BSP/TTBP, Tf₂O, MS-4Å, DCM, -60° C., 1 h.

After the donor 6 (500 mg, 0.85 mmol) and activated molecular sieve MS-4 Å (500 mg) were stirred for 30 minutes at room temperature in DCM (20 mL), the solution was cooled to -60° C., followed by addition of 1-benzenesulfinyl piperidine (190 mg, 0.89 mmol) and 2,4,6-Tri-tert-butylpyrimidine (0.42 g, 1.7 mmol). The mixture was stirred for 5 minutes at -60° C. and then Tf₂O (0.15 mL, 0.89 mmol) was added. The mixture was vigorously stirred for 10 minutes at -60° C., followed by addition of a solution of acceptor 7 (544 mg, 0.81 mmol) in DCM (5 mL). The reaction mixture was stirred for 1 hour at -60° C. and then was quenched with Et₃N (1 mL). The mixture was diluted with DCM (150 mL), washed with a saturated aqueous solution of NaHCO₃, H₂O and then dried over Na₂SO₄, filtered and concentrated. Silica gel column chromatography (15:1:1 hexanes-EtOAc-DCM) afforded 8 as a white solid (690 mg, 70%). $^1$H-NMR (500 MHz, CDCl₃): δ 0.19-0.23 (m, 6H, TDS), 0.90-0.94 (m, 12H, TDS), 1.66-1.71 (m, 1H, TDS), 3.21-3.25 (m, 1H, H-6b), 3.29-3.34 (m, 1H, H-2), 3.47-3.49 (m, 1H, H-6b'), 3.55-3.63 (m, 2H, H-3', H-6a'), 3.65-3.70 (m, 2H, H-5', H-6a), 3.88-3.89 (m, 1H, H-2'), 3.92-3.97 (m, 1H, H-5), 4.01-4.04 (m, 1H, H-3), 4.17-4.24 (m, 2H, H-4, H-4'), 4.44 (d, 1H, J=12.0 Hz, Bn), 4.59-4.67 (m, 3H, H-1', Bn), 4.72 (br, 2H, Troc), 4.80 (d, 1H, J=12.0 Hz, Bn), 4.92 (d, 1H, J=12.0 Hz, Bn), 4.97-4.98 (m, 3H, H-1, Nap), 5.10 (d, 1H, J=12.0 Hz, Bn), 5.17 (br, 1H, NH), 5.63 (s, 1H, PhCH), 7.23-7.41 (m, 13H), 7.42-7.58 (m, 10H), 7.73-7.75 (m, 1H), 7.84-7.90 (m, 3H); $^{13}$C-NMR (75 MHz, CDCl₃): δ −3.4, −1.9, 18.5, 18.6, 20.0, 20.1, 24.8, 34.0, 59.6, 67.4, 68.6, 68.9, 72.4, 73.5, 74.2, 74.5, 74.7, 75.0, 76.6, 78.2, 78.3, 78.7, 95.2, 95.4, 101.4, 101.7, 125.5, 125.8, 126.0, 126.1, 126.2, 126.9, 127.1, 127.4, 127.5, 127.6 (×2), 127.7, 127.8 (×2), 127.9 (×2), 128.0, 128.1, 128.2 (×2), 128.3 (×2), 128.4, 128.9, 132.9, 133.3, 135.9, 137.7, 137.8, 138.6, 138.9, 153.8. gHMQC (without $^1$H decoupling): $^1J_{C1,H1}$=160.5 Hz, 157.5 Hz.

mixture was cooled to −70° C., followed by addition of TfOH (28 μL, 0.32 mmol). The reaction mixture was stirred for 1 hour from −70 to −20° C. and then was quenched with Et₃N (0.1 mL). The mixture was diluted with DCM (200 mL), washed with a saturated aqueous solution of NaHCO₃, H₂O and then dried over Na₂SO₄, filtered and concentrated. Silica gel column chromatography (3:1:1 hexanes-EtOAc-DCM) afforded 12 as a white solid (2.4 g, 92%). $^1$H-NMR (500 MHz, CDCl₃): δ 3.16-3.21 (m, 1H), 3.29-3.31 (m, 1H), 3.38-3.40 (m, 1H), 3.48-3.55 (m, 3H), 3.58-3.71 (m, 4H), 3.75-3.78 (m, 2H), 3.88-3.92 (m, 2H), 4.03-4.07 (m, 1H), 4.10-4.20 (m, 2H), 4.23-4.26 (m, 2H), 4.42-4.49 (m, 2H), 4.52-4.54 (m, 2H, H-1"), 4.59-4.74 (m, 8H, H-1, H-1'), 4.82-4.90 (m, 3H), 4.94-5.07 (m, 5H), 5.13-5.17 (m, 2H), 5.64 (s, 1H, PhCH), 7.21-7.62 (m, 38H), 7.77-7.79 (m, 1H), 7.88-7.93 (m, 3H); $^{13}$C-NMR (75 MHz, CDCl₃): δ 56.6, 57.3, 60.3, 67.2, 67.9, 68.3, 68.5, 70.4, 72.2, 72.6, 73.2 (×2), 73.4, 73.9, 74.2, 74.3, 74.9, 76.5, 76.6, 77.5, 77.8, 78.0, 78.5, 78.6, 79.4, 95.4, 95.5, 99.5, 100.3, 101.3, 101.4, 125.3, 125.8, 125.9 (×2), 126.0 (×2), 126.3, 126.6, 127.2, 127.3, 127.5 (×3), 127.6 (×2), 127.7 (×2), 127.9, 128.0, 128.1 (×2), 128.2, 128.3, 128.4, 128.6, 128.8, 128.9, 132.8, 133.1, 135.8, 137.2, 137.5 (×2), 137.8, 138.4, 138.5, 138.6, 138.8,

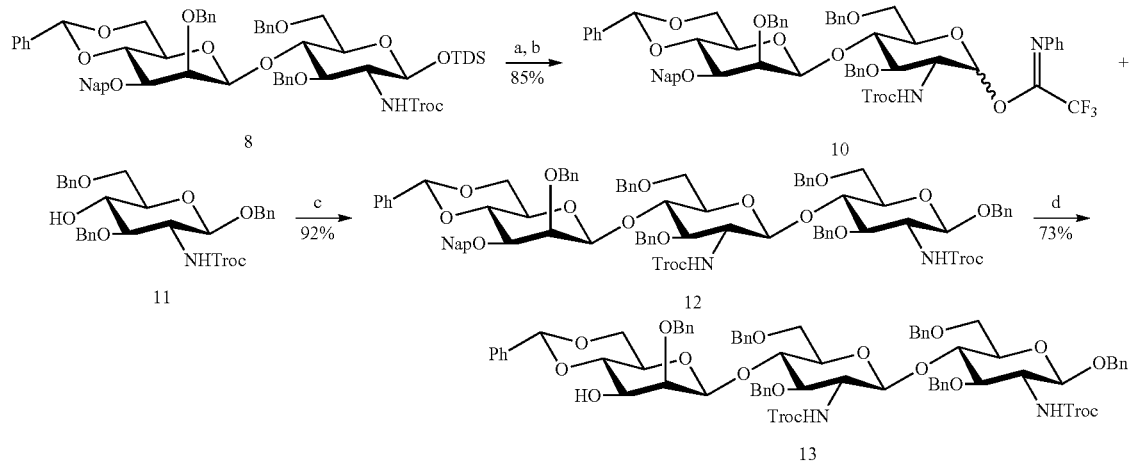

Scheme 12. Synthesis of Trisaccharide acceptor 13.

Reagents: a) HF/pyridine, pyridine, rt, overnight; b) CF₃C(NPh)Cl, DBU, DCM, rt, 1 h; c) TfOH, DCM, MS-4Å, −70° C. to −20° C., 1 h; d) DDQ, DCM/H₂O, rt, 3 h.

Compound 8 (4.5 g, 3.88 mmol) was dissolved in pyridine (68 mL). The mixture was cooled to 0° C., followed by addition of HF (34 mL, 65-70% in pyridine). The mixture was stirred at room temperature overnight and then was diluted in EtOAc (200 mL), washed with 10% of CuSO₄, saturated aqueous NaHCO₃ and H₂O. The organic layer was dried over Na₂SO₄, filtered and concentrated. Silica gel column chromatography (2:1 hexane-EtOAc) afforded the corresponding hemiacetal as a white solid (3.94 g, 99%). The mixture of the obtained solid (3.9 g, 3.84 mmol), N-phenyltrifluoroacetimidoyl chloride (3.1 mL, 19.2 mmol) and DCM (150 mL) was cooled down to 0° C. DBU (0.58 mL, 3.84 mmol) was added and the mixture was stirred at room temperature for 1 hour. The mixture was concentrated. Silica gel column chromatography (4:1 hexanes-EtOAc) afforded the corresponding imidate 10 as a white solid (3.9 g, 86%). Imidate donor 10 (1.9 g, 1.6 mmol), acceptor 11 (950 mg, 1.52 mmol), molecular sieve MS-4 Å and DCM (120 mL) were stirred at room temperature for 30 min. The 153.8, 153.9. gHMQC (without $^1$H decoupling): $^1J_{C1,H1}$= 162.5 Hz, 159.8 Hz, 164.6 Hz.

Compound 12 (1.6 g, 0.99 mmol) was dissolved in a mixture of DCM/H₂O (35 mL/3.5 mL) and the solution was cooled to 0° C. 2,3-Dichloro-5,6-dicyano-p-benzoquinone (0.27 g, 1.19 mmol) was added to the solution and the mixture was stirred at room temperature for 3 h. The mixture was filtered, diluted with DCM (100 mL) and the organic phase was washed with H₂O until the solution became colorless. Silica gel column chromatography (3:2 hexanes-EtOAc) afforded compound 13 as a white solid (1.07 g, 73%). $^1$H-NMR (500 MHz, CDCl₃): δ 2.44 (d, 1H, J=8.5 Hz), 3.08-3.13 (m, 1H), 3.23-3.25 (m, 1H), 3.32-3.34 (m, 1H), 3.44-3.65 (m, 7H), 3.71-3.77 (m, 4H), 3.85-3.87 (m, 1H), 4.01-4.12 (m, 3H), 4.33-4.39 (m, 2H), 4.46-4.56 (m, 4H, H-1"), 4.61-4.70 (m, 7H, H-1, H-1'), 4.73-4.84 (m, 3H), 4.93-5.01 (m, 2H), 5.06-5.09 (m, 3H), 5.48 (s, 1H, PhCH), 7.20-7.47 (m, 33H), 7.50-7.52 (m, 2H); $^{13}$C-NMR (75 MHz, CDCl₃): δ 56.8, 57.3, 66.8, 68.0, 68.3, 68.5, 70.6, 70.8 73.5

(×2), 74.1, 74.2, 74.3, 74.4, 75.6, 77.9, 78.6, 78.8, 79.0, 79.6, 95.4, 95.6, 99.5, 100.3, 101.6, 101.9, 126.2, 127.3, 127.4 (×2), 127.6, 127.7, 127.8, 127.9 (×2), 128.0, 128.1, 128.2 (×2), 128.3, 128.5 (×2), 128.7, 128.9, 129.1, 137.2 (×2), 137.5, 137.9, 138.1, 138.7 (×2), 153.9 (×2).

Scheme 13. Synthesis of Mannose building block 76.

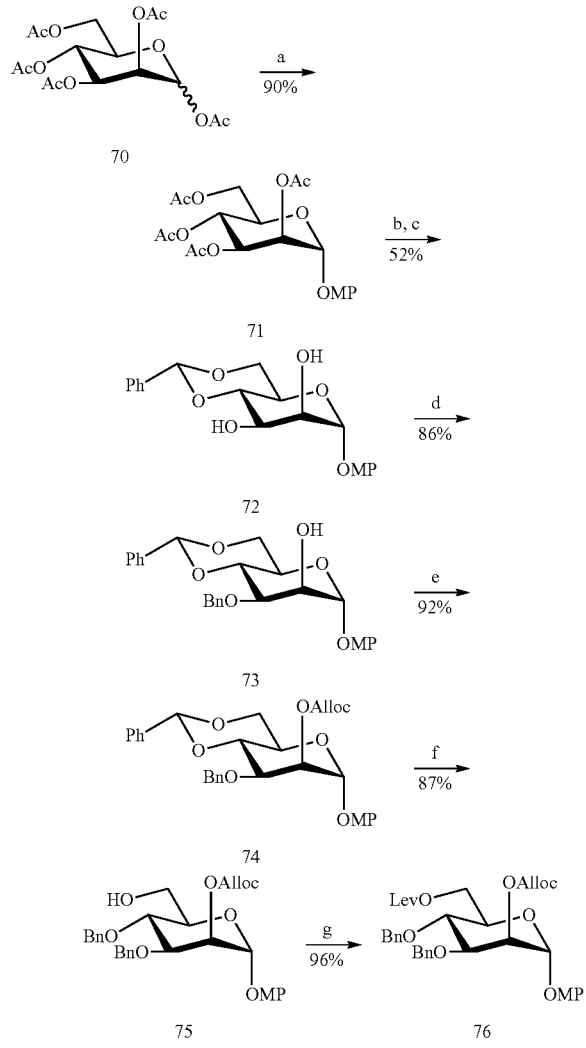

Reagents: a) p-methoxyphenol, BF₃ etherate, DCM, rt, overnight; b) NaOMe, MeOH/DCM, rt, 2 h; c) PhCH(OMe)₂, CSA, DMF, 70° C., overnight; d) Bu₂SnO, Toluene, reflux, 3 h, then BnBr, CsF, DMF, rt, overnight; e) AllocCl, TMEDA, rt, 4 h; f) Et₃SiH/PhBCl₂, DCM, -78° C., 1 h; g) LevOH, EDC·HCl, DMAP, DCM, rt, overnight.

Pentaacetylated Mannose 70 (20 g, 51.2 mmol) and p-methoxyphenol (7.3 g, 58.9 mmol) were dissolved in DCM (200 mL). The mixture was cooled down to 0° C., followed by addition of Boron trifluoride diethyl etherate (19.3 ml, 153.7 mmol). The mixture was stirred at room temperature overnight and then diluted with dichloromethane (300 mL). The resulting solution was washed with saturated aqueous solution of NaHCO₃ and water and then dried over Na₂SO₄, filtered and concentrated to dryness. Silica gel column chromatography (3:2 hexanes-EtOAc) afforded compound 71 as white solid (21.1 g, 90%). $^1$H-NMR (500 MHz, CDCl₃): δ 2.03 (s, 3H, COCH₃), 2.04 (s, 3H, COCH₃), 2.06 (s, 3H, COCH₃), 2.19 (s, 3H, COCH₃), 3.76 (s, 3H, MP), 4.08-4.10 (m, 1H, H-5), 4.13-4.16 (m, 1H, H-6b), 4.26-4.30 (m, 1H, H-6a), 5.36 (t, 1H, J=10.0 Hz, H-4), 4.42 (d, 1H, J=1.5 Hz, H-1), 5.43-5.45 (m, 1H, H-2), 5.54 (dd, 1H, J=10.0 Hz, 3.5 Hz, H-3), 6.81-6.84 (m, 2H), 7.01-7.04 (m, 2H); $^{13}$C-NMR (75 MHz, CDCl₃): δ 20.4 (×2), 20.6, 55.3, 62.0, 65.8, 68.7, 68.8, 69.2, 96.4, 114.4, 117.6, 149.4, 155.2, 169.5, 169.6, 169.7, 170.2; gHMQC (without $^1$H decoupling): $^1J_{C1,H1}$=179.1 Hz.

71 (11 g, 24.2 mmol) was dissolved in a mixture of DCM/MeOH (100 mL each) and NaOMe (30%, 5.4 mL, 96.8 mmol) was added to the solution at room temperature. The mixture was stirred for 2 h at room temperature under N₂ and then the mixture was neutralized by conc. HCl until the pH was around 4. The mixture was concentrated and dried under vacuum. The mixture of the obtained compound (6.7 g, 23.4 mmol), camphorsulfonic acid (1.09 g, 4.68 mmol) and benzaldehyde dimethylacetal (3.86 mL, 25.7 mmol) in DMF (80 mL) was stirred at 70° C. overnight and then quenched by Et₃N (5 mL). The mixture was concentrated to dryness under vacuum and then was diluted with DCM (500 mL). The mixture was washed with a saturated aqueous solution of NaHCO₃, water, and then the organic layer was dried over Na₂SO₄, filtered and concentrated. Silica gel column chromatography (2:1 hexane-EtOAc) afforded compound 72 as a white solid (4.68 g, 52% for 2 steps). Compound 72 (3.6 g, 9.62 mmol), di-butyltin oxide (2.5 g, 10.1 mmol) and Toluene (100 mL) were refluxed for 3 h, followed by removal of solvent under vacuo. The mixture of the resulting solid, cesium fluoride (1.53 g, 10.1 mmol), Benzyl bromide (1.2 mL, 10.1 mmol) and DMF (50 mL) was stirred at room temperature overnight. DMF was removed by vacuum and the mixture was diluted with DCM (200 mL). The mixture was washed with saturated aqueous solution of NaHCO₃, water and then dried over Na₂SO₄, filtered and concentrated. Silica gel column chromatography (3:1 hexanes-EtOAc) afforded compound 73 as white solid (3.8 g, 86%). $^1$H-NMR (500 MHz, CDCl₃): δ 3.26 (br, 1H, 2-OH), 3.81 (s, 3H, MP), 3.81-3.97 (m, 1H, H-4), 4.03-4.08 (m, 1H, H-3), 4.16-4.18 (m, 1H, H-5), 4.21-4.22 (m, 1H, H-2), 4.25-4.28 (m, 2H, H-6a, H-6b), 4.82 (d, 1H, J=12.0 Hz, Bn), 4.98 (d, 1H, J=12.0 Hz, Bn), 5.51 (br, 1H, H-1), 5.68 (s, 1H, PhCH), 6.88-6.90 (m, 2H), 7.02-7.04 (m, 2H), 7.34-7.47 (m, 8H), 7.57-7.58 (m, 2H); $^{13}$C-NMR (75 MHz, CDCl₃): δ 55.5, 63.9, 68.6, 69.8, 73.2, 75.5, 78.7, 98.8, 101.5, 114.6, 117.6, 126.0, 127.8, 127.9, 128.1, 128.4, 128.8, 137.4, 137.9, 149.7, 155.0.

The mixture of compound 73 (1.85 g, 3.98 mmol), Allyl chloroformate (0.51 mL, 4.78 mmol), Tetramethylethylenediamine (0.89 mL, 5.97 mmol) and DCM (50 mL) were stirred at room temperature for 4 h and then was diluted with DCM (200 mL). The organic layer was washed with saturated aqueous solution of NaHCO₃, water and then dried over Na₂SO₄, filtered and concentrated. Silica gel column chromatography (2:1 hexanes-EtOAc) afforded compound 74 as white solid (2.01 g, 92%). $^1$H-NMR (500 MHz, CDCl₃): δ 3.80 (br, 3H, MP), 3.90 (t, 1H, J=10.0 Hz, H-4), 4.08-4.12 (m, 1H, H-3), 4.23-4.32 (m, 3H, H-5, H-6a, H-6b), 4.72 (d, 2H, J=5.5 Hz, Alloc), 4.86 (br, 2H, Alloc), 5.33 (d, 1H, J=10.5 Hz, Bn), 5.44 (d, 1H, J=10.5 Hz, Bn), 5.49 (m, 1H, H-2), 5.58 (br, 1H, H-1), 5.69 (s, 1H, PhCH), 5.96-6.04 (m, 1H, Alloc), 6.88-6.90 (m, 2H), 7.03-7.05 (m, 2H), 7.33-7.48 (m, 8H), 7.57-7.58 (m, 2H); $^{13}$C-NMR (75 MHz, CDCl₃): δ 55.5, 64.4, 68.4, 68.9, 72.4, 75.5, 73.7, 78.1, 97.5, 101.5, 114.6, 117.8, 119.1, 126.0, 127.5 (×2), 128.1, 128.2, 128.8, 131.2, 137.3, 138.0, 149.5, 154.4, 155.3.

Compound 74 (0.7 g, 1.27 mmol) was dissolved in DCM (50 mL) and the solution was cooled down to −78° C., followed by sequential addition of Triethylsilane (0.31 mL, 1.91 mmol) and Dichlorophenylborane (0.28 mL, 2.16 mmol). The mixture was stirred at −78° C. for 1 h and then quenched by MeOH/Et₃N (0.5 mL/each). The resulting mixture was washed by saturated aqueous NaHCO₃ and H₂O and concentrated. Silica gel chromatography (2:1 hexanes-EtOAc) afforded compound 75 (0.61 g, 87%). ¹H-NMR (500 MHz, CDCl₃): δ 2.05 (t, 1H, J=6.5 Hz, 6-OH), 3.78 (br, 3H, MP), 3.82-3.83 (m, 2H, H-6a, H-6b), 3.88-3.90 (m, 1H, H-5), 4.01 (t, 1H, J=10.0 Hz, H-4), 4.24 (dd, 1H, J=8.5 Hz, 3.0 Hz, H-3), 4.68-4.72 (m, 4H, Alloc), 4.87 (d, 1H, J=11.0 Hz, Bn), 4.98 (d, 1H, J=11.0 Hz, Bn), 5.30 (d, 1H, J=11.0 Hz, Bn), 5.39-5.43 (m, 2H, H-2, Bn), 5.55 (br, 1H, H-1), 5.93-6.01 (m, 1H, Alloc), 6.84-6.86 (m, 2H), 6.99-7.01 (m, 2H), 7.27-7.44 (m, 10H); ¹³C-NMR (75 MHz, CDCl₃): δ 55.5, 61.8, 68.9, 72.0, 72.3, 72.6, 73.9, 75.4, 77.8, 96.8, 114.6, 117.9, 119.2, 127.7, 127.8, 127.9, 128.0, 128.3, 128.4, 131.3, 137.9, 138.2, 149.6, 154.5, 155.3.

75 (0.49 g, 0.89 mmol) was dissolved in DCM (20 mL), followed by addition of levulinoyl acid (0.13 g, 1.25 mmol), N-(3-Dimethylaminopropyl)-N'-ethylcarbodiimide hydrochloride (0.27 g, 1.42 mmol) and 4-(Dimethylamino)pyridine (11 mg, 0.09 mmol). The mixture was stirred at room temperature overnight and then was diluted with DCM (100 mL). The organic phase was washed with saturated NaHCO₃ and then dried over Na₂SO₄, filtered and the solvents were removed in vacuum. Silica gel column chromatography (3:1 hexanes-EtOAc) afforded compound 76 as white solid (0.56 g, 96%). ¹H-NMR (500 MHz, CDCl₃): δ 2.19 (s, 3H, Lev), 2.57-2.61 (m, 2H, Lev), 2.67-2.77 (m, 2H, Lev), 3.80 (br, 3H, MP), 4.89 (t, 1H, J=10.0 Hz, H-4), 4.01-4.04 (m, 1H, H-5), 4.24 (dd, 1H, J=9.5 Hz, 3.0 Hz, H-3), 4.32-4.38 (m, 2H, H-6a, H-6b), 4.63-4.71 (m, 4H, Alloc), 4.86 (d, 1H, J=11.0 Hz, Bn), 4.97 (d, 1H, J=11.0 Hz, Bn), 5.31 (d, 1H, J=10.5 Hz, Bn), 5.39-5.43 (m, 2H, H-2, Bn), 5.55 (br, 1H, H-1), 5.94-6.02 (m, 1H, Alloc), 6.84-6.87 (m, 2H), 7.00-7.03 (m, 2H), 7.29-7.43 (m, 10H); ¹³C-NMR (75 MHz, CDCl₃): δ 27.9, 29.7, 378, 55.6, 63.1, 68.9, 70.3, 72.0, 72.2, 73.8, 75.3, 77.9, 96.5, 114.6, 117.8, 119.2, 127.8 (×2), 127.9, 128.1, 128.4 (×2), 131.3, 137.7, 137.9, 149.7, 154.5, 155.2, 172.3, 206.4.

Scheme 14. Synthesis of Mannose donor 14.

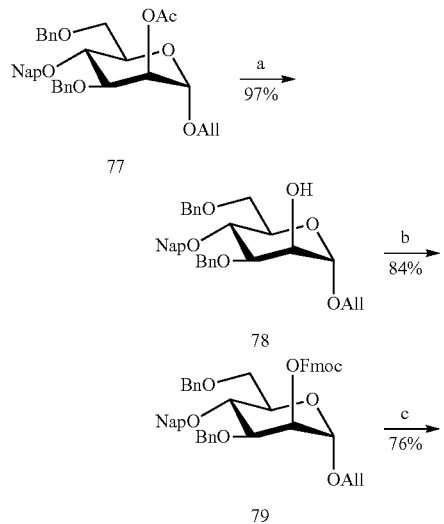

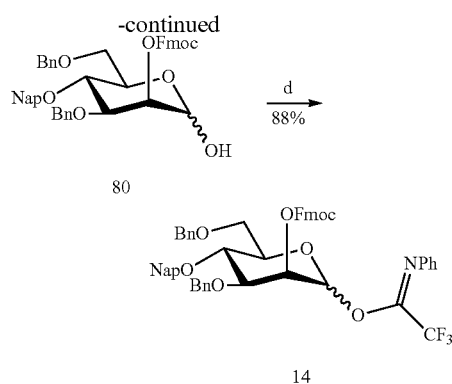

Reagents: a) NaOMe, MeOH/DCM, rt, 2 h; b) FmocCl, pyridine, DCM, rt, 4 h; c) PdCl₂, NaOAc, DCM/AcOH/H₂O, rt, overnight; d) CF₃C(NPh)Cl, 60% NaH, DCM, rt, 1 h.

77 (1.65 g, 2.83 mmol) was dissolved in a mixture of DCM/MeOH (20 mL each) and NaOMe (30%, 0.32 mL, 5.66 mmol) was added to the solution at room temperature. The mixture was stirred for 2 h at room temperature under N₂ and was neutralized with conc.HCl until the pH was around 7 and then the mixture was concentrated. Silica gel column chromatography (3:1 hexanes-EtOAc) afforded compound 78 as white solid (1.49 g, 97%). ¹H-NMR (500 MHz, CDCl₃): δ 2.45 (s, 1H, 2-OH), 3.63-3.65 (m, 1H, H-6b), 3.70-3.75 (m, 2H, H-5, H-6a), 3.83-3.88 (m, 2H, H-4, All), 3.90-3.94 (m, 1H, H-3), 4.00 (br, 1H, H-2), 4.09-4.13 (m, 1H, All), 4.43 (d, 1H, J=12.0 Hz, Bn), 4.57-4.66 (m, 4H, Bn, Nap), 4.89-4.91 (m, 2H, H-1, Nap), 4.09-5.11 (m, 1H, All), 5.17-5.21 (m, 1H, All), 5.77-5.85 (m, 1H, All), 7.15-7.29 (m, 11H), 7.36-7.39 (m, 2H), 7.53 (br, 1H), 7.66-7.68 (m, 2H), 7.72-7.74 (m, 1H); ¹³C-NMR (75 MHz, CDCl₃): δ 68.0, 68.4, 68.9, 71.1, 72.0, 73.4, 74.3, 75.2, 80.3, 98.4, 117.5, 119.2, 125.8, 126.0 (×2), 126.5, 127.6 (×2), 127.8, 127.9 (×2), 128.0 128.3, 128.5, 132.9, 133.3, 133.7, 135.8, 137.9, 138.2.

78 (0.82 g, 1.52 mmol) was dissolved in DCM (30 mL). 9-Fluorenylmethoxycarbonyl chloride (0.78 g, 3.04 mmol) and pyridine (1.22 mL, 15.2 mmol) were added sequentially and the mixture was stirred for 4 h at room temperature under N₂. The mixture was diluted with DCM (100 mL) and the organic phase was washed with saturated NaHCO₃ and then dried over Na₂SO₄, filtered and the solvents were removed in vacuum. Silica gel column chromatography (7:1 hexanes-EtOAc) afforded compound 79 as white solid (0.98 g, 84%). ¹H-NMR (500 MHz, CDCl₃): δ 3.87-3.89 (m, 1H, H-6b), 3.95-4.03 (m, 2H, H-5, H-6a), 4.11-4.22 (m, 3H, H-3, H-4, All), 4.30-4.38 (m, 2H, Fmoc, All), 4.42-4.45 (m, 1H, Fmoc), 4.54-4.57 (m, 1H, Fmoc), 4.64 (d, 1H, J=12.0 Hz, Bn), 4.72 (d, 1H, J=12.0 Hz, Bn), 4.79-4.83 (m, 2H, Bn, Nap), 4.90 (d, 1H, J=11.5 Hz, Bn), 5.15-5.18 (m, 2H, H-1, Nap), 5.31 (d, 1H, J=10.0 Hz, All), 5.37-5.41 (m, 2H, H-2, All), 5.96-6.04 (m, 1H, All), 7.27-7.49 (m, 15H), 7.53-7.57 (m, 2H), 7.72-7.77 (m, 3H), 7.84-7.86 (m, 4H), 7.89-7.91 (m, 1H); ¹³C-NMR (75 MHz, CDCl₃): δ 46.6, 68.1, 68.9, 70.2, 71.6, 71.8, 72.7, 73.4, 74.4, 75.3, 78.3, 96.6, 117.8, 119.9, 120.0, 125.2, 125.4, 125.8, 125.9, 126.5, 127.1, 127.5, 127.6 (×2), 127.7, 127.8, 127.9, 128.0, 128.2, 128.3, 132.9, 133.2, 133.3, 135.8, 137.9, 138.2, 141.1, 141.2, 143.2, 143.5, 154.8.

79 (1.66 g, 2.18 mmol) was dissolved in a mixture of DCM/MeOH/H₂O (20 mL/20 mL/1 mL). NaOAc (1.07 g, 13.1 mmol) and PdCl₂ (0.77 g, 4.36 mmol) were added to the solution at room temperature. The mixture was stirred at room temperature under N$_2$ overnight and then was concentrated to dryness. The residue was diluted with DCM (200 mL) and the organic phase was washed with H$_2$O and then dried over Na$_2$SO$_4$, filtered and the solvents were removed in vacuum. Silica gel column chromatography (3:1 hexanes-EtOAc) afforded the corresponding hemiacetal 80 as a colorless gel (1.2 g, 76%). The mixture of the obtained solid (1.2 g, 1.66 mmol), N-phenyltrifluoroacetimidoyl chloride (1.35 mL, 8.3 mmol) and DCM (80 mL) was cooled down to 0° C. NaH (60%, 66 mg, 1.66 mmol) was added and the mixture was stirred at room temperature for 1 h. The mixture was concentrated. Silica gel column chromatography (8:1 hexanes-EtOAc) afforded the corresponding imidate 14 as a white solid (1.3 g, 88%).

(75 MHz, CDCl$_3$): δ 13.6, 20.9, 46.4, 56.7, 57.3, 60.3, 64.2, 66.8, 67.9, 68.2, 68.3, 69.1, 70.1, 70.5, 71.5, 72.1, 72.3, 73.2, 73.4, 73.5, 74.0, 74.1, 74.2, 74.3, 74.5, 75.2, 75.3, 75.5, 77.3, 77.4, 77.8, 78.3, 78.5, 78.6, 79.4, 95.4, 95.5, 98.3, 99.5, 100.3, 101.0, 101.1, 119.9 (×2), 125.1, 125.3, 125.8 (×2), 125.9, 126.0, 126.4, 127.1, 127.3, 127.4, 127.5, 127.6 (×2), 127.7 (×3), 127.8, 127.9 (×2), 128.0, 128.1, 128.2 (×2), 128.3 (×2), 128.5, 128.7, 128.9, 132.8, 133.1, 135.8, 137.1, 137.2, 137.6, 137.7, 137.8, 138.0, 138.3, 138.6, 138.7, 141.1 (×2), 143.2, 143.4, 153.8, 153.9, 154.5. gHMQC (without $^1$H decoupling): $^1J_{C1,H1}$=163.6, 163.4, 161.9, 176.6 Hz.

Compound 15 (100 mg, 45.7 µmol) was dissolved in DCM (8 mL) and the solution was cooled down to −78° C., followed by sequential addition of Triethylsilane (11 µL, 68.56 µmol) and Dichlorophenylborane (10.2 µL, 77.7

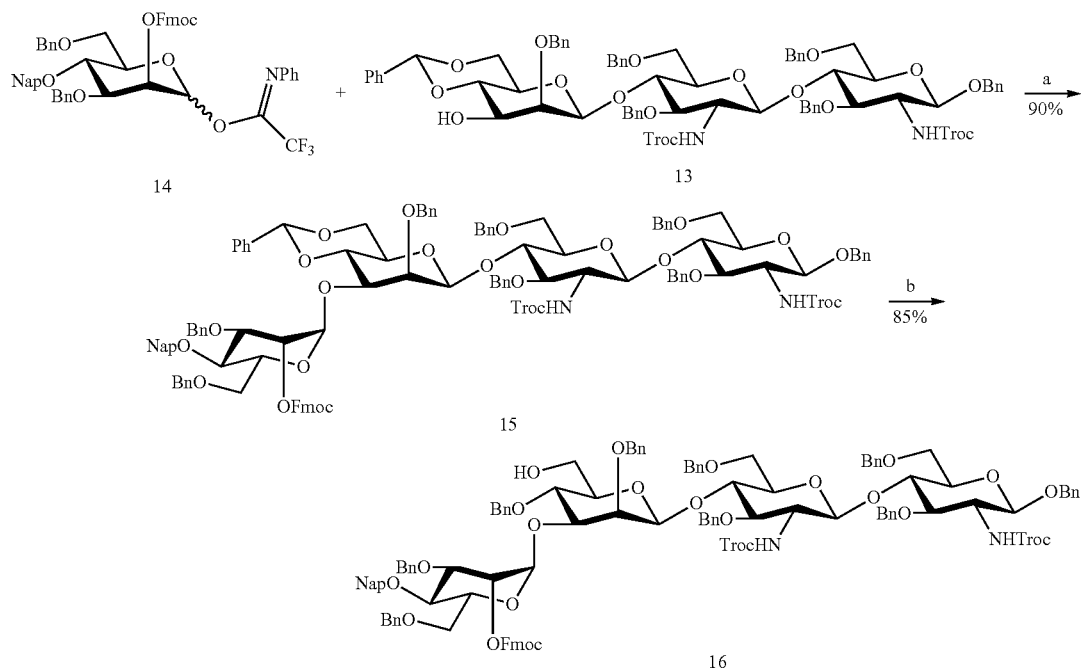

Scheme 15. Synthesis of tetrasaccharide 16.

Reagents: a) TfOH, DCM, MS-4Å, -60° C. to -20° C., 1 h; c) Et$_3$SiH/PhBCl$_2$, DCM, -78° C., 1 h.

The obtained imidate 14 (97 mg, 0.11 mmol), acceptor 13 (80 mg, 0.055 mmol), molecular sieve MS-4 Å and DCM (10 mL) was stirred at room temperature for 30 min. The mixture was cooled to −60° C., followed by addition of TfOH (1.9 µL, 0.022 mmol). The reaction mixture was stirred for 1 hour from −60 to −20° C. and then was quenched with solid NaHCO$_3$ (20 mg). The mixture was diluted with DCM (50 mL), washed with a saturated aqueous solution of NaHCO$_3$, H$_2$O and then dried over Na$_2$SO$_4$, filtered and concentrated. Silica gel column chromatography (4:1:1 hexanes-EtOAc-DCM) afforded 15 as a white solid (110 mg, 90%). $^1$H-NMR (500 MHz, CDCl$_3$): δ 2.88-2.93 (m, 1H), 3.07-3.09 (m, 1H), 3.16-3.18 (m, 1H), 3.29-3.42 (m, 4H), 3.44-3.49 (m, 2H), 3.55-3.64 (m, 3H), 3.70-3.72 (m, 4H), 3.78-3.81 (m, 1H), 3.83-3.98 (m, 6H), 4.10-4.15 (m, 3H), 4.17-4.23 (m, 1H), 4.26-4.36 (m, 4H), 4.38-4.48 (m, 6H), 4.52-4.70 (m, 9H), 4.73-4.83 (m, 4H), 4.90-4.92 (m, 2H), 4.97-5.00 (m, 1H), 5.33-5.34 (m, 2H), 5.40 (s, 1H, PhCH), 7.03-7.27 (m, 42H), 7.30-7.41 (m, 10H), 7.50-7.55 (m, 3H), 7.64-7.69 (m, 4H), 7.73-7.76 (m, 1H); $^{13}$C-NMR µmol). The mixture was stirred at −78° C. for 40 minutes and then quenched with solid NaHCO$_3$ and MeOH. The resulting mixture was washed by saturated aqueous NaHCO$_3$ and H$_2$O and concentrated. Silica gel chromatography (3:1:1 hexanes-EtOAc-DCM) afforded compound 16 (85.1 mg, 85%). $^1$H-NMR (500 MHz, CDCl$_3$): δ 3.02-3.03 (m, 1H), 3.17-3.22 (m, 2H), 3.36-3.38 (m, 1H), 3.43-3.47 (m, 2H), 3.51-3.78 (m, 10H), 3.85-4.07 (m, 8H), 4.27-4.34 (m, 4H), 4.38-4.49 (m, 4H), 4.51-4.68 (m, 11H), 4.71-4.81 (m, 4H), 4.83-4.97 (m, 4H), 5.02-5.11 (m, 4H), 5.35-5.38 (m, 2H), 7.18-7.42 (m, 44H), 7.44-7.54 (m, 8H), 7.65-7.70 (m, 3H), 7.78-7.84 (m, 4H), 7.87-7.89 (m, 1H); $^{13}$C-NMR (75 MHz, CDCl$_3$): δ 14.1, 21.0, 46.5, 56.7, 57.3, 60.3, 61.7, 68.0, 68.3, 69.2, 70.3, 70.6, 71.8, 72.5, 72.6, 73.3, 73.4, 73.6, 74.1 (×2), 74.3, 74.4, 74.6, 74.8, 74.9, 75.1, 75.6, 76.6, 77.5, 77.6, 77.9, 78.1, 78.6, 79.7, 80.4, 95.5 (×2), 99.3, 99.6, 100.5 (×2), 120.0 (×2), 125.2, 125.4, 125.8, 125.9, 126.0, 126.3, 126.9, 127.0, 127.1, 127.3, 127.5 (×2), 127.6, 127.7 (×2), 127.8 (×2), 127.9 (×2), 128.1, 128.2 (×2), 128.3 (×2), 128.4, 128.5, 128.7, 128.8, 129.1, 132.9, 133.2, 133.9, 135.8, 137.2, 137.6, 137.7, 137.8 (×2), 138.0, 138.6 (×2), 138.7, 141.2 (×2), 143.2, 143.5, 154.1, 154.6.

Scheme 16. Synthesis of Pentasaccharide 1.

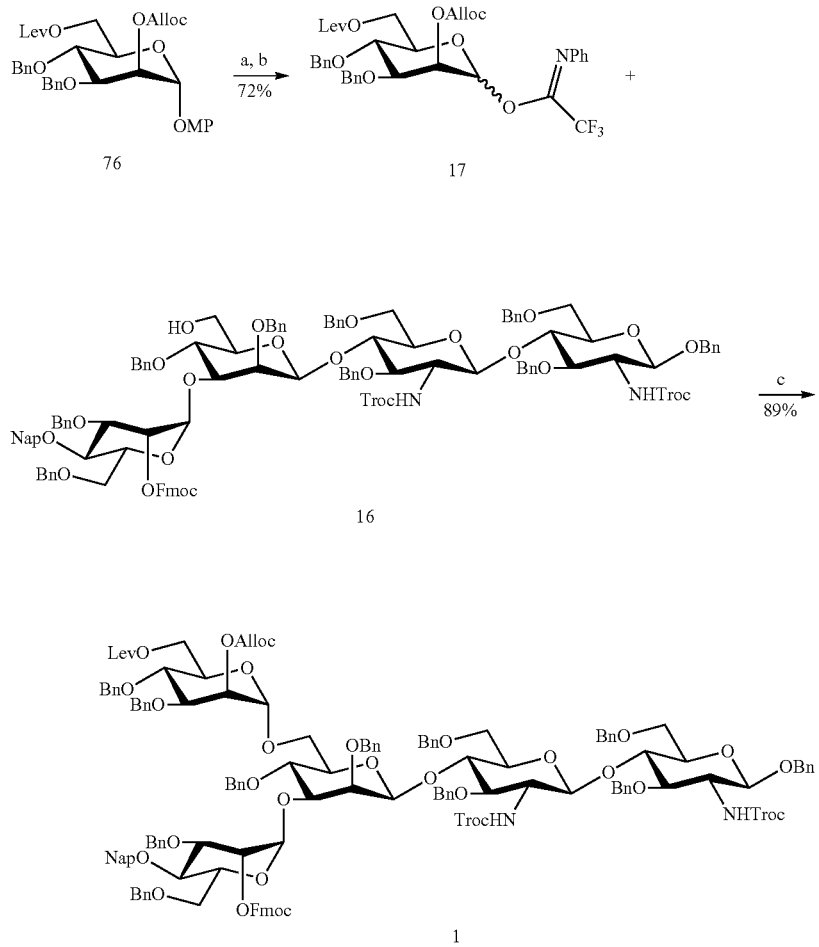

Reagents: a) CAN, CH₃CN/H₂O, rt, 2 h; b) CF₃C(NPh)Cl, 60% NaH, DCM, rt, 1 h; c) TfOH, DCM, MS-4Å, -60° C. to -20° C., 1 h.

76 (1.0 g, 1.54 mmol) was dissolved in a mixture of CH$_3$CN//H$_2$O (30 mL/7.5 mL). Ceric ammonium nitrate (2.54 g, 4.62 mmol) was added to the solution at 0° C. and then the mixture was stirred at room temperature under N$_2$ for 2 h. The mixture was concentrated to dryness and the residue was diluted with DCM (100 mL) and the organic phase was washed with H$_2$O and then dried over Na$_2$SO$_4$, filtered and the solvents were removed in vacuum. Silica gel column chromatography (3:2 hexanes-EtOAc) afforded the corresponding hemiacetal. The compound obtained (0.74 g, 1.36 mmol), N-phenyltrifluoroacetimidoyl chloride (1.1 mL, 6.8 mmol) and DCM (70 mL) were cooled down to 0° C. NaH (60%, 54 mg, 1.36 mmol) was added and the mixture was stirred at room temperature for 1 h, concentrated and purified via Silica gel column chromatography (4:1 hexanes-EtOAc) to afforded the corresponding imidate 17 as a white solid (790 mg, 72% for 2 steps). Imidate 17 (0.65 g, 0.91 mmol), tetrasaccharide acceptor 16 (1.0 g, 0.46 mmol), molecular sieve MS-4 Å and DCM (120 mL) were stirred at room temperature for 30 min. The mixture was cooled to -60° C., followed by addition of TfOH (16.1 µL, 0.18 mmol). The reaction mixture was stirred for 1 hour from -60 to -20° C. and then was quenched with solid NaHCO$_3$. The mixture was diluted with DCM (100 mL), washed with a saturated aqueous solution of NaHCO$_3$, H$_2$O and then dried over Na$_2$SO$_4$, filtered and concentrated. Silica gel column chromatography (2.5:1:1 hexanes-EtOAc-DCM) afforded pentasaccharide 1 as a white solid (1.1 g, 89%). $^1$H-NMR (500 MHz, CDCl$_3$): δ 2.02 (s, 3H, Lev), 2.37-2.40 (m, 2H, Lev), 2.51-2.55 (m, 2H, Lev), 3.01-3.08 (m, 2H), 3.20-3.24 (m, 1H), 3.29-3.34 (m, 3H), 3.44-3.65 (m, 12H), 3.75-3.89 (m, 7H), 3.94-4.05 (m, 3H), 4.13-4.22 (m, 5H), 4.27-4.61 (m, 24H), 4.65-4.68 (m, 1H), 4.72-4.80 (m, 5H), 4.89-4.98 (m, 4H), 5.06 (br, 1H), 5.13 (d, 1H, J=10.5 Hz), 5.18-5.24 (m, 3H), 5.72-5.80 (m, 1H, Alloc), 7.01-7.25 (m, 56H), 7.31-7.40 (m, 6H), 7.52-7.57 (m, 3H), 7.64-7.71 (m, 4H), 7.74-7.76 (m, 1H); $^{13}$C-NMR (75 MHz, CDCl$_3$): δ 14.1, 27.8, 29.7, 37.8, 46.5, 48.6, 52.4, 56.4, 57.4, 60.3, 63.1, 66.6, 68.1, 68.4, 68.6, 69.2, 69.9, 70.3, 70.5, 71.3, 71.8, 71.9, 72.5, 72.6, 73.2, 73.4, 73.7, 74.3, 74.1, 74.2, 74.3 (×2), 74.5, 74.8, 75.1 (×2), 76.3, 77.3, 77.7, 78.0, 78.1, 78.6, 81.1, 95.5, 95.6, 97.4, 99.3, 99.5 (×2), 100.3, 101.3, 118.9, 119.9, 120.0 (×2), 125.1, 125.4, 125.8, 125.9, 126.0, 126.3, 127.1, 127.3, 127.4, 127.5, 127.6, 127.7 (×3), 127.8, 127.9, 128.0 (×2), 128.2 (×3), 128.3 (×3), 128.4, 128.5 (×2), 131.4, 132.9, 133.2, 135.8, 137.2, 137.7, 137.8, 137.9, 138.0, 138.2, 138.6, 138.8, 139.0, 141.2 (×2), 143.2, 143.5, 153.8 (×2), 154.2, 154.6, 171.1, 206.5. gHMQC (without $^1$H decoupling): $^1J_{C1,H1}$=158.3, 162.0, 165.5, 169.3, 171.4 Hz.

Scheme 17. Versatility of core Pentasaccharide 1: deprotection of Fmoc group.

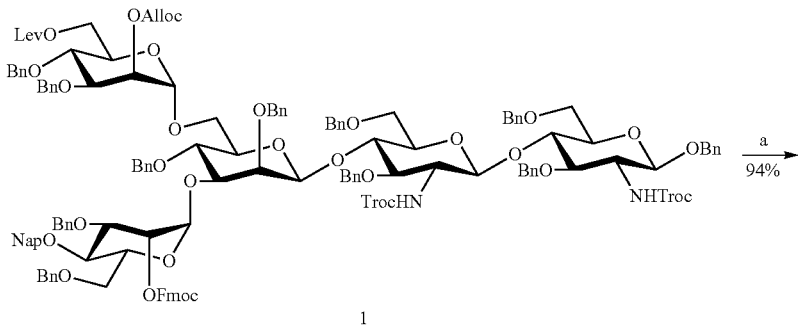

Reagents: a) Et₃N, DCM, rt, 4 h

Pentasaccharide 1 (20 mg, 7.37 μmmol) was dissolved in DCM (2 mL). Et$_3$N (0.5 mL) was added to the solution and then the mixture was stirred at room temperature under N$_2$ for 4 h. The mixture was concentrated to dryness and then the residue was co-evaporated with toluene (3×5 mL). The solvents were removed in vacuum. Silica gel column chromatography (1.5:1:1 hexanes-EtOAc-DCM) afforded compound 18 (17.3 mg, 94%). $^1$H-NMR (600 MHz, CDCl$_3$): δ 2.04 (s, 3H, Lev), 2.31 (br, 1H, OH), 2.38-2.40 (m, 2H, Lev), 2.49-2.56 (m, 2H, Lev), 2.99-3.01 (m, 1H), 3.06-3.08 (m, 1H), 3.18-3.21 (m, 1H), 3.28-3.44 (m, 3H), 3.44-3.50 (m, 4H), 3.53-3.65 (m, 8H), 3.72-3.89 (m, 9H), 3.98-4.00 (m, 1H), 4.03-4.05 (m, 1H), 4.18-4.22 (m, 3H), 4.25-4.27 (m, 1H), 4.43-4.41 (m, 7H), 4.43-4.62 (m, 16H), 4.73-4.80 (m, 5H), 4.89-4.95 (m, 4H), 5.06 (br, 1H), 5.13 (d, 1H, J=10.8 Hz), 5.23 (d, 1H, J=11.4 Hz), 5.75-5.80 (m, 1H, Alloc), 7.00-7.03 (m, 1H), 7.07-7.26 (m, 53H), 7.36-7.41 (m, 4H), 7.53 (br, 1H), 7.64-7.69 (m, 2H), 7.74-7.76 (m, 1H); $^{13}$C-NMR (75 MHz, CDCl$_3$): δ 14.1, 27.8, 29.7, 37.8, 46.5, 48.6, 52.4, 56.4, 57.4, 60.3, 63.1, 66.6, 68.1, 68.4, 68.6, 69.2, 69.9, 70.3, 70.5, 71.3, 71.8, 71.9, 72.5, 72.6, 73.2, 73.4, 73.7, 74.3, 74.1, 74.2, 74.3 (×2), 74.5, 74.8, 75.1 (×2), 76.3, 77.3, 77.7, 78.0, 78.1, 78.6, 81.1, 95.5, 95.6, 97.4, 99.3, 99.5, 100.3, 101.4 (×2), 119.0, 125.8, 125.9, 126.0, 126.3, 127.2, 127.3 (×2), 127.4 (×2), 127.5 (×2), 127.7 (×3), 127.8 (×2), 127.9 (×2), 128.0, 128.1 (×2), 128.2, 128.3 (×2), 128.4, 128.5 (×2), 128.6 (×2), 128.7, 131.4, 132.9, 133.2, 135.9, 137.3, 137.8 (×3), 137.9, 138.0, 138.2, 138.9, 139.0, 153.9 (×2), 154.3, 172.3, 206.6.

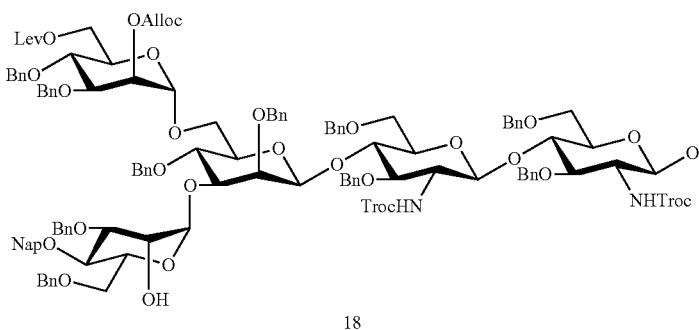

Scheme 18. Versatility of core Pentasaccharide 1: deprotection of Nap group.

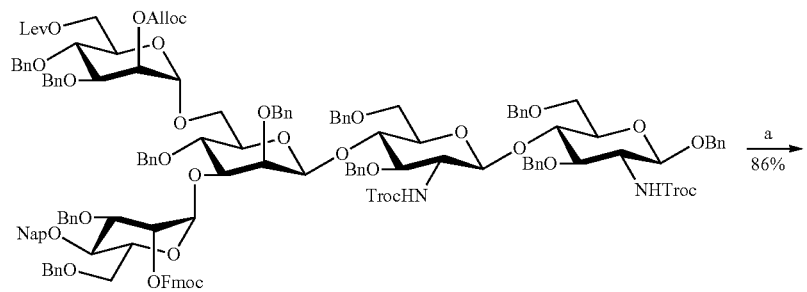

-continued

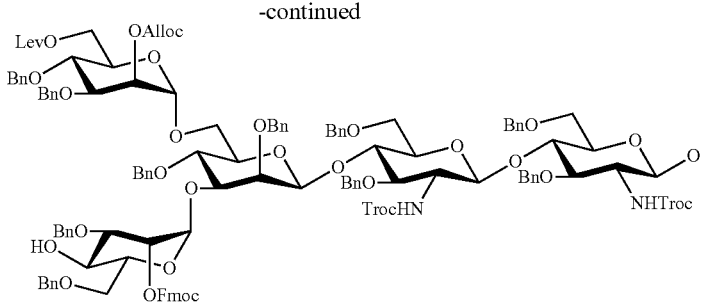

19

Reagents: a) DDQ, DCM/H₂O, rt, 3 h

Pentasaccharide 1 (30 mg, 11.1 μmol) was dissolved in a mixture of DCM//H₂O (3 mL/0.3 mL) and the solution was cooled to 0° C. DDQ (3.0 mg, 13.3 μmol) was added to the solution and the mixture was stirred at room temperature under N₂ for 3 h. The mixture was diluted with DCM (30 mL) and the organic phase was washed with H₂O until the solution became colorless. The organic phase was dried over Na₂SO₄, filtered and the solvents were removed in vacuum. Silica gel column chromatography (2.5:1:1 hexanes-EtOAc-DCM) afforded compound 19 (24.6 mg, 86%). ¹H-NMR (600 MHz, CDCl₃): δ 2.03 (s, 3H, Lev), 2.38 (br, 1H, OH), 2.39-2.40 (m, 2H, Lev), 2.51-2.56 (m, 2H, Lev), 2.99-3.01 (m, 1H), 3.06-3.07 (m, 1H), 3.20-3.23 (m, 1H), 3.29-3.33 (m, 3H), 3.43-3.45 (m, 1H), 3.47-3.53, (m, 3H), 3.55-3.65 (m, 7H), 3.68-3.71 (m, 2H), 3.76-3.79 (m, 2H), 3.81-3.89 (m, 5H), 3.96-4.05 (m, 2H), 4.12-4.21 (m, 5H), 4.28-4.54 (m, 21H), 4.60-4.70 (m, 3H), 4.73-4.82 (m, 5H), 4.91-4.96 (m, 3H), 5.07 (br, 1H), 5.12-5.23 (m, 4H), 5.74-5.79 (m, 1H, Alloc), 7.01-7.06 (m, 3H), 7.11-7.28 (m, 52H), 7.32-7.38 (m, 4H), 7.50-7.54 (m, 2H), 7.70-7.71 (m, 1H); ¹³C-NMR (125 MHz, CDCl₃): δ 27, 29.7, 37.9, 46.6, 57.4, 63.2, 66.6, 67.2, 68.1, 68.4, 68.7, 69.9, 70.1, 70.4, 70.5, 71.3, 71.7, 71.8, 71.9, 72.3, 73.2, 73.5, 73.6, 73.7, 73.8, 74.4, 74.5 (×2), 74.6, 74.8 75.2, 77.4, 77.8, 78.1, 78.2, 78.6, 81.1, 95.6, 97.5, 99.5, 99.6, 100.3, 101.3, 104.3, 119.0, 120.0 (×2), 125.2, 125.3, 127.2 (×3), 127.3, 127.4, 127.5 (×2), 127.6, 127.7 (×2), 127.8 (×2), 127.9 (×2), 128.0, 128.1 (×2), 128.2 (×2), 128.3 (×2), 128.4 (×3), 128.5, 128.6 (×3), 131.4, 137.2, 137.5, 137.7, 137.8 (×2), 137.9, 138.0, 138.2, 138.6, 138.9, 139.0, 141.2 (×2), 143.2, 143.4, 153.9 (×2), 154.3, 154, 172.3, 206.6.

Scheme 19. Versatility of core Pentasaccharide 1: deprotection of Alloc group.

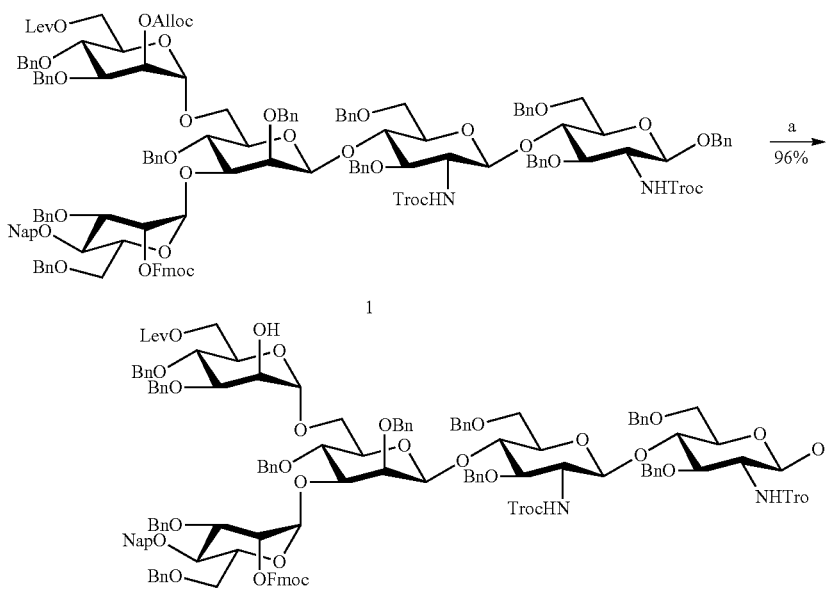

Reagents: a) Pd(PPh₃)₄, THF/H₂O, rt, overnight

Pentasaccharide 1 (30 mg, 11.1 μmol) was dissolved in a mixture of THF//H$_2$O (3 mL/0.3 mL). Palladium-tetrakis (triphenylphosphine) (6.4 mg, 5.6 μmol) was added to the solution and then the mixture was stirred at room temperature overnight. The mixture was concentrated and then the residue was co-evaporated with toluene (3×5 mL). The solvents were removed in vacuum. Silica gel column chromatography (3:2:1 hexanes-EtOAc-DCM) afforded compound 20 (27.8 mg, 96%). $^1$H-NMR (600 MHz, CDCl$_3$): δ 2.02 (s, 3H, Lev), 2.16 (br, 1H, OH), 2.37-2.39 (m, 2H, Lev), 2.51-2.54 (m, 2H, Lev), 3.02-3.03 (m, 2H), 3.12-3.15 (m, 1H), 3.29-3.31 (m, 1H), 3.33-3.38 (m, 2H), 3.46-3.68 (m, 13H), 3.76-3.80 (m, 3H), 3.85-3.89 (m, 4H), 3.94-3.96 (m, 1H), 3.99-4.09 (m, 2H), 4.13-4.20 (m, 4H), 4.23-4.24 (m, 1H), 4.30-4.34 (m, 4H), 4.36-4.40 (m, 4H), 4.45-4.47 (m, 6H), 4.50-4.54 (m, 4H), 4.57-4.67 (m, 5H), 4.7-4.75 (m, 2H), 4.78-4.81 (m, 3H), 4.92-4.98 (m, 4H), 5.19 (br, 1H), 5.25 (br, 1H), 7.02-7.27 (m, 56H), 7.32-7.41 (m, 6H), 7.52-7.57 (m, 3H), 7.63-7.71 (m, 4H), 7.74-7.75 (m, 1H); $^{13}$C-NMR (125 MHz, CDCl$_3$): δ 27.8, 29.7, 29.8, 37.8, 46.5, 56.5, 57.2, 60.4, 63.2, 66.2, 67.6, 68.1, 68.4, 69.1, 69.7, 70.3, 70.5, 71.2, 71.8, 72.5, 72.6, 73.3, 73.5 (×2), 73.7 (×2), 73.9, 74.3, 74.4, 74.5, 74.7, 74.8, 75.0, 75.2, 76.6, 77.5, 77.7, 78.0, 78.1, 78.6, 79.4 (×2), 80.9, 95.6 (×2), 99.3, 99.6 (×2), 100.5, 101.0, 120.0 (×2), 125.2, 125.4, 125.8, 125.9, 126.4, 127.2, 127.3 (×2), 127.5, 127.6 (×4), 127.7 (×2), 127.8 (×3), 127.9 (×3), 128.1, 128.2 (×3), 128.3 (×3), 128.4 (×2), 128.6 (×2), 128.8, 132.9, 133.2, 135.8, 137.2, 137.7, 137.8 (×3), 138.0, 138.2, 138.7, 138.8, 141.2 (×3), 143.5, 153.9, 154.0, 154.6, 172.4, 206.7.

Pentasaccharide 1 (30 mg, 11.1 μmol) was dissolved in a mixture of DCM/MeOH (3 mL/0.3 mL). Hydrazine acetate (1.22 mg, 13.3 μmol) was added and then the mixture was stirred at room temperature under N$_2$ for 5 h. The mixture was concentrated to dryness. Silica gel column chromatography (2.5:1:1 hexanes-EtOAc-DCM) afforded compound 21 (24.5 mg, 85%). $^1$H-NMR (500 MHz, CDCl$_3$): δ 2.31 (br, 1H, OH), 3.02-3.04 (m, 1H), 3.0-3.10 (m, 1H), 3.27-3.31 (m, 3H), 3.37-3.38 (m, 2H), 3.47-3.7 (m, 14H), 3.72-3.74 (m, 1H), 3.79-3.80 (m, 1H), 3.87-3.88 (m, 2H), 3.93-3.97 (m, 2H), 4.05-4.08 (m, 1H), 4.14-4.28 (m, 5H), 4.30-4.63 (m, 24H), 4.67-4.69 (m, 1H), 4.72-4.84 (m, 4H), 4.93-4.98 (m, 4H), 5.04-5.14 (m, 3H), 5.2 (br, 1H), 5.24-5.26 (m, 2H), 5.77-5.82 (m, 1H, Alloc), 7.06-7.26 (m, 56H), 7.32-7.35 (m, 4H), 7.39-7.41 (m, 2H), 7.52-7.57 (m, 3H), 7.64-7.71 (m, 4H), 7.74-7.76 (m, 1H); $^{13}$C-NMR (125 MHz, CDCl$_3$): δ 29.7, 46.5, 56.5, 57.8, 61.3, 67.1, 67.9, 68.4, 68.8, 69.2, 69.9, 70.3, 70.5, 71.5 (×2), 71.9, 72.2, 72.5, 72.6, 72.7, 73.3 (×2), 73.4, 73.9, 74.0, 74.3 (×2), 74.5, 74.9 (×2), 75.0, 75.1, 75.4, 76.5, 77.4, 77.8, 78.0 (×2), 78.4, 81.2, 95.6, 97.2, 99.5 (×2), 100.0, 101.0, 119.2, 120.0 (×2), 125.2, 125.4, 125.8, 125.9, 126.0, 126.3, 127.2, 127.3, 127.4 (×2), 127.5, 127.6 (×2), 127.7 (×4), 127.8 (×3), 127.9 (×2), 128.0 (×2), 128.1 (×2), 128.2, 128.3 (×2), 128.4 (×2), 128.5, 128.6 (×2), 131.4, 132.9, 133.2, 135.9, 137.3, 137.5, 137.6, 137.8, 138.0 (×2), 138.1, 138.5, 138.6, 139.0, 141.2, 141.3, 143.2, 143.5, 153.8, 153.9, 154.2, 154.7.

Scheme 21. Synthesis of glucosamine building block 87

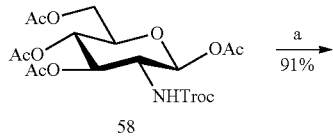

58

Scheme 20. Versatility of core Pentasaccharide 1: deprotection of Lev group.

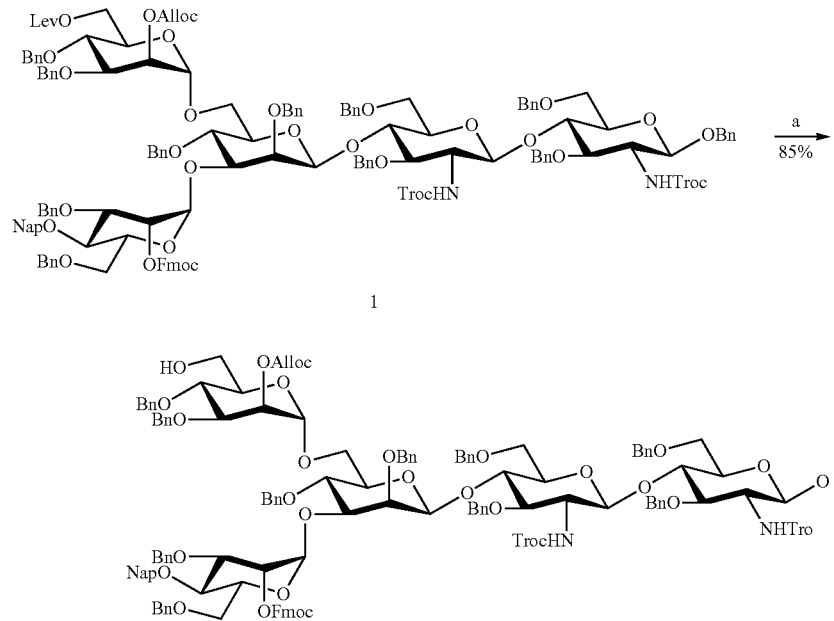

21

Reagents: a) NH$_2$NHOAc, DCM/MeOH, rt, 5 h

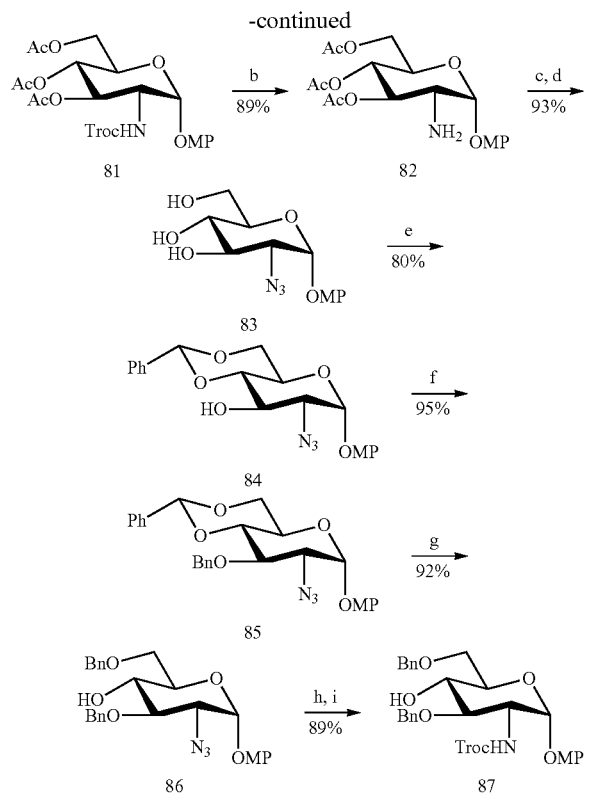

Reagents: a) p-methoxyphenol, BF₃ etherate, DCM, rt, overnight; b) Zn dust, AcOH/DCM/MeOH, rt, 1 h; c) NaOMe(5.3M), MeOH/DCM, rt, 2 h; d) K₂CO₃/ZnCl₂, TfN₃, DCM/MeOH/H₂O, rt, overnight; e) PhCH(OCH₃)₂, CSA, toluene, rt, 2 h; f) NaH, BnBr, DMF, 2 h; g) Et₃SiH/TfOH, DCM, -78° C., 1 h; h) PMe₃(1M), NaOH, THF/H₂O, rt, overnight; i) TrocCl, solid NaHCO₃, THF, 4 h; j) BnBr, NaH, DMF, rt, 2 h.

58 (22 g, 42.1 mmol) and p-methoxylphenol (6 g, 48.4 mmol) were dissolved in DCM (200 mL). The mixture was cooled down to 0° C., followed by addition of trifluoroborine etherate (15.9 ml, 126.3 mmol). The mixture was stirred at room temperature overnight and diluted with dichoromethane (200 mL). The resulting solution was washed with saturated aqueous solution of NaHCO₃ and water and then dried over Na₂SO₄, filtered and concentrated to dryness. Silica gel column chromatography (3:2 hexanes-EtOAc) afforded 81 as white solid (22.5 g, 91%). ¹H-NMR (500 MHz, CDCl₃): δ 2.05 (br, 6H, Ac), 2.06 (br, 3H, Ac), 3.78 (s, 3H, MP), 4.07-4.15 (m, 2H, H-6a, H-6b), 4.19-4.27 (m, 2H, H-2, H-3), 4.63 (d, 1H, J=12.0 Hz, Troc), 4.82 (d, 1H, J=12.0 Hz, Troc), 5.20 (t, 1H, J=10.0 Hz, H-4), 5.43-5.46 (m, 2H, H-5, NH), 5.48 (d, 1H, J=3.0 Hz, H-1), 6.83-6.85 (m, 2H), 7.02-7.04 (m, 2H); ¹³C-NMR (75 MHz, CDCl₃): δ 20.5, 20.6 (×2), 54.0, 55.5, 61.7, 68.0, 68.2, 70.7, 74.5, 95.2, 96.7, 114.6, 117.8, 149.8, 154.2, 155.5, 169.3, 170.4, 170.9. gHMQC (without ¹H decoupling): $^1J_{C1,H1}$= 174.4 Hz.

81 (12 g, 20.5 mmol) was dissolved in MeOH (45 mL), AcOH (24 mL) and DCM (24 mL). Zn powder (24.1 g, 369 mmol) was added slowly at 0° C. and the mixture was stirred under N₂ at room temperature for 1 hour. The mixture was filtered and concentrated to dryness. The resulting residue was diluted with DCM (300 mL), washed with a saturated aqueous solution of NaHCO₃ until the pH was around 7 and then the organic layer was dried over Na₂SO₄, filtered and concentrated. Silica gel column chromatography (6:1 DCM-MeOH) afforded 82 as a white solid (7.2 g, 89%). Compound 82 (7.2 g, 17.5 mmol) was dissolved in MeOH (35 mL) and DCM (35 mL). 5.33 M NaOMe (9.9 mL, 52.5 mmol) was added to the solution and the mixture was stirred at room temperature for 2 h. The mixture was neutralized by conc. HCl until the pH was around 7 and then concentrated and dried under vacuum. The resulting residue, K₂CO₃ (4.8 g, 35 mmol) and a catalytic amount of ZnCl₂ (120 mg, 0.9 mmol) were dissolved in MeOH (40 mL) and H₂O (10 mL). Freshly prepared TfN₃ (50 mL in DCM, 52.5 mmol) was added to the solution and the mixture was stirred at room temperature overnight. The solvent was evaporated and the resulting residue was diluted with EtOAc (200 mL). The mixture was neutralized by conc. HCl until the pH value was 6-7 and then concentrated to dryness. Silica gel column chromatography (10:1 DCM-MeOH) afforded 83 as a white solid (5.05, 93% over two steps). The obtained compound 83 (5 g, 16.1 mmol), camphorsulfonic acid (1.12 g, 4.83 mmol) and benzaldehyde dimethylacetal (2.89 mL, 19.3 mmol) in anhydrous toluene (100 mL) was stirred at room temperature for 2 h and then diluted with EtOAc (200 mL). The mixture was washed with a saturated aqueous solution of NaHCO₃, water, and then the organic layer was dried over Na₂SO₄, filtered and concentrated. Silica gel column chromatography (2:1 hexane-EtOAc) afforded compound 84 as a white solid (5.13 g, 80%). ¹H-NMR (500 MHz, CDCl₃): δ 3.17 (br, 1H, OH), 3.41 (dd, 1H, J=10.0 Hz, 3.5 Hz, H-2), 3.61 (t, 1H, J=9.5 Hz, H-4), 3.75-3.79 (m, 1H, H-6b), 3.82 (br, 1H, MP), 4.05-4.10 (m, 1H, H-6a), 4.27-4.30 (m, 1H, H-5), 4.41 (t, 1H, J=10.0 Hz, H-3), 4.45 (d, 1H, J=3.5 Hz, H-1), 5.58 (s, 1H, PhCH), 6.88-6.91 (m, 2H), 7.05-7.08 (m, 2H), 7.41-7.44 (m, 3H), 7.53-7.55 (m, 2H); ¹³C-NMR (75 MHz, CDCl₃): δ 55.6, 62.9, 63.0, 68.6, 68.7, 81.7, 98.3, 102.1, 114.7, 118.2, 126.3, 128.4, 129.4, 136.8, 150.3, 155.5.

84 (3 g, 7.51 mmol) was dissolved in DMF (50 mL) and the solution was cooled to 0° C. NaH (0.36 g, 60% NaH in mineral oil, 9 mmol) was added in portions, followed by addition of Benzyl bromide (1.07 mL, 9 mmol). The mixture was stirred at room temperature under N₂ for 2 h and then concentrated to dryness. The residue was diluted with EtOAc (100 mL). The mixture was washed with saturated NaHCO₃, water, and then the organic layer was dried over Na₂SO₄, filtered and concentrated. Silica gel column chromatography (3:1 hexane-EtOAc) afforded 85 as a white solid (3.5 g, 95%). ¹H-NMR (500 MHz, CDCl₃): δ 3.54 (dd, 1H, J=10.0 Hz, 3.5 Hz, H-2), 3.79-3.86 (m, 5H, H-4, H-6b, MP), 4.11-4.16 (m, 1H, H-5), 4.29-4.34 (m, 2H, H-3, H-6a), 4.90 (d, 1H, J=11.0 Hz, Bn), 5.05 (d, 1H, J=11.0 Hz, Bn), 5.47 (d, 1H, J=3.0 Hz, H-1), 5.65 (s, 1H, PhCH), 6.88-6.89 (m, 2H), 7.06-7.07 (m, 2H), 7.29-7.46 (m, 8H), 7.53-7.55 (m, 2H); ¹³C-NMR (75 MHz, CDCl₃): δ 55.7, 62.9, 63.3, 68.8, 75.1, 76.0, 82.7, 98.3, 101.5, 114.7, 118.2, 126.0, 127.9, 128.2, 128.3, 128.5, 129.1, 137.1, 137.8, 150.3, 155.5.

Compound 85 (2 g, 4.09 mmol) was dissolved in DCM (200 mL) and the solution was cooled down to -78° C., followed by sequential addition of Et₃SiH (2.1 mL, 13.1 mmol) and TfOH (1.05 mL, 11.9 mmol). The mixture was stirred at -78° C. for 1 h and then quenched by MeOH/Et₃N (2 mL/each). The resulting mixture was washed by saturated aqueous NaHCO₃ and H₂O and concentrated. Silica gel chromatography (3:1:1 hexanes-EtOAc-DCM) afforded compound 86 (1.84 g, 92%). ¹H-NMR (500 MHz, CDCl₃): δ 2.89 (d, 1H, J=3.5 Hz, OH), 3.47 (dd, 1H, J=10.0 Hz, 3.5 Hz, H-2), 3.73-3.90 (m, 6H, H-5, H-6a, H-6b, MP), 4.04-4.10 (m, 1H, H-4), 4.12-4.14 (m, 1H, H-3), 4.56-4.66 (m, 2H, Bn), 4.95-5.06 (m, 2H, Bn), 5.49 (d, 1H, J=3.0 Hz, H-1), 6.89-6.91 (m, 2H), 7.15-7.16 (m, 2H), 7.36-7.47 (m, 8H), 7.51-7.53 (m, 2H); $^{13}$C-NMR (75 MHz, CDCl$_3$): δ 55.5, 62.5, 63.3, 69.4, 70.6, 71.8, 73.5, 75.0, 79.5, 97.8, 114.5, 118.2, 127.5, 127.7, 127.9, 128.0, 128.3, 128.5, 137.6, 138.0, 150.4, 155.3.

86 (0.65 g, 1.32 mmol) 1 M PMe$_3$ in THF (6.6 mL, 6.6 mmol), 1 M NaOH (3.4 mL, 3.4 mmol) and THF/H$_2$O (40 mL/10 mL) was stirred at room temperature overnight. The mixture was concentrated and the resulting residue was diluted with DCM (100 mL). The mixture was neutralized by conc. HCl until the pH was around 7. The mixture was concentrated and dried under vacuum. The resulting residue was purified by quickly passing through a short silica gel column (10:1, DCM-MeOH). The obtained solid and solid NaHCO$_3$ (0.22 g, 2.64 mmol) were put into THF (16 mL) and then 2,2,2-Trichloroethyl chloroformate (0.21 mL, 1.58 mmol) was added to the solution. The mixture was stirred at room temperature under N$_2$ for 4 hours and filtered. The filtrate was concentrated and then diluted with DCM (50 mL). The mixture was washed with water, brine, and then the organic layer was dried over Na$_2$SO$_4$, filtered and concentrated. Silica gel column chromatography (7:1 hexane-EtOAc) afforded compound 87 as a white solid (0.75 g, 89% for two steps). $^1$H-NMR (500 MHz, CDCl$_3$): δ 2.99 (d, 1H, J=2.5 Hz, OH), 3.73-3.81 (m, 5H, H-6a, H-6b, MP), 3.83-3.87 (m, 1H, H-5), 3.90-3.94 (m, 1H, H-3), 4.00-4.03 (m, 1H, H-4), 4.15-4.21 (m, 1H, H-2), 4.56 (d, 1H, J=12.0 Hz, Bn), 4.63 (d, 1H, J=12.0 Hz, Bn), 4.70 (d, 1H, J=12.0 Hz, Bn), 4.86-4.92 (m, 3H, Bn, Troc), 5.35 (d, 1H, J=9.5 Hz, NH), 5.47 (d, 1H, J=3.5 Hz, H-1), 6.85-6.87 (m, 2H), 7.05-7.07 (m, 2H), 7.29-7.42 (m, 10H); $^{13}$C-NMR (75 MHz, CDCl$_3$): δ 54.4, 55.5, 69.7, 70.7, 71.9, 73.5, 74.4, 74.6, 79.7, 95.3, 97.5, 114.6, 118.2, 127.5, 127.7 (×2), 127.8 (×2), 128.3, 128.5, 137.7, 138.1, 150.1, 154.2, 155.3.

Scheme 22. Synthesis of disaccharide donor 3

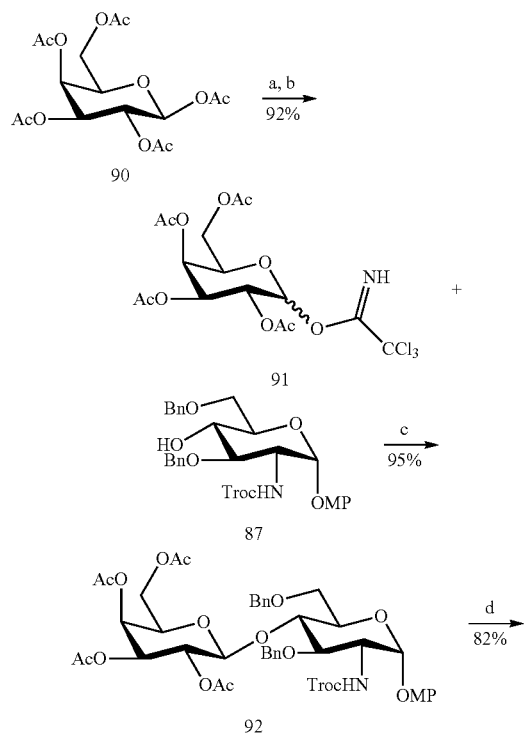
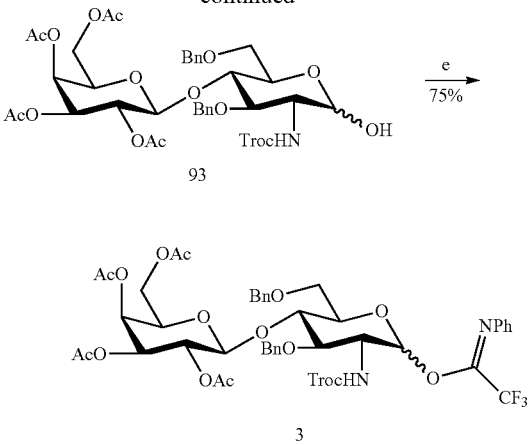

Reagents: a) NH$_2$NHOAc, DMF, rt, overnight; b) CCl$_3$CN, CsCO$_3$, DCM, rt, 1 h; c) TfOH, DCM, MS-4Å, -70° C. to -20° C., 1 h; d) CAN, CH$_3$CN/H$_2$O, rt, 2 h; e) CF$_3$C(NPh)Cl, DBU, DCM, rt, 1 h.

1,2,3,4,6-penta-O-acetyl-β-D-galactopyranoside 90 (5 g, 12.8 mmol) was dissolved in DMF (60 mL) and hydrazine acetate (1.3 g, 14.1 mmol) was added. The mixture was stirred at room temperature overnight and then concentrated to dryness. The resulting residue was diluted with EtOAc (200 mL) and then washed with saturated aqueous solution of NaHCO$_3$ and water. The organic phase was dried over Na$_2$SO$_4$, filtered and concentrated to dryness. Silica gel column chromatography (1:1 hexanes-EtOAc) afforded compound as white solid (4.27 g, 96%). The obtained solid (2.1 g, 6.03 mmol), Cl$_3$CCN (12.1 mL, 121 mmol) and DCM (40 mL) was cooled down to 0° C. Cs$_2$CO$_3$ (1.96 g, 6.03 mmol) was added and the mixture was stirred at room temperature for 1 h. The mixture was concentrated. Silica gel column chromatography (2:1 hexanes-EtOAc) afforded the corresponding imidate 91 as a white solid (2.85 g, 96%). Imidate 91 (0.88 g, 1.62 mmol), acceptor 87 (0.73 g, 1.1 mmol), molecular sieve MS-4 Å and DCM (40 mL) was stirred at room temperature for 30 min. The mixture was cooled to −70° C., followed by addition of TfOH (29 μL, 0.32 mmol). The reaction mixture was stirred for 1 hour from −70 to −20° C. and then was quenched with Et$_3$N (0.05 mL). The mixture was diluted with DCM (200 mL), washed with a saturated aqueous solution of NaHCO$_3$, H$_2$O and then dried over Na$_2$SO$_4$, filtered and concentrated. Silica gel column chromatography (3:2 hexanes-EtOAc) afforded disaccharide 92 as a white solid (1.05 g, 95%). $^1$H-NMR (500 MHz, CDCl$_3$): δ 1.96 (s, 3H, Ac), 1.98 (s, 3H, Ac), 2.01 (s, 3H, Ac), 2.10 (s, 3H, Ac), 3.58-3.63 (m, 2H, H-6a, H-6b), 3.77 (s, 3H, MP), 3.81-3.83 (m, 3H, H-3, H-5, H-6b'), 3.86-3.96 (m, 2H, H-4, H-6a'), 4.08-4.16 (m, 2H, H-2, H-5'), 4.44 (d, 1H, J=12.0 Hz, Bn), 4.50 (d, 1H, J=8.0 Hz, H-1'), 4.70 (d, 1H, J=11.0 Hz, Bn), 4.75-4.82 (m, 3H, H-3', Troc), 5.02 (d, 1H, J=12.0 Hz, Bn), 5.13 (t, 1H, J=9.5 Hz, H-2'), 5.21-5.23 (m, 1H, H-4'), 5.27 (br, 1H, NH), 5.49 (d, 1H, J=3.0 Hz, H-1), 6.82-6.84 (m, 2H), 7.00-7.02 (m, 2H), 7.26-7.43 (m, 10H); $^{13}$C-NMR (75 MHz, CDCl$_3$): δ 20.4 (×2), 20.5, 20.6, 20.9, 54.6, 55.5, 60.2, 60.5, 66.7, 67.1 69.4, 70.3, 70.8, 71.0, 73.5, 74.3, 74.4, 76.4, 77.4, 95.2, 96.9, 100.0, 114.5, 117.6, 127.4 (×2), 128.1, 128.5, 137.4, 138.4, 150.1, 154.1, 155.1, 169.1, 169.8, 170.0 (×2). gHMQC (without $^1$H decoupling): $^1J_{C1,H1}$=174.8, 163.1 Hz.

Disaccharide 92 (1.0 g, 1.03 mmol) was dissolved in a mixture of CH$_3$CN//H$_2$O (30 mL/7.5 mL). Ceric ammonium nitrate (1.69 g, 3.09 mmol) was added to the solution at 0° C. and then the mixture was stirred at room temperature under N$_2$ for 2 h. The mixture was concentrated to dryness and the residue was diluted with DCM (100 mL) and the organic phase was washed with H$_2$O and then dried over Na$_2$SO$_4$, filtered and the solvents were removed in vacuum. Silica gel column chromatography (3:2 hexanes-EtOAc) afforded the corresponding hemiacetal 93 (730 mg, 82%). Compound 93, N-phenyltrifluoroacetimidoyl chloride (0.68 mL, 4.2 mmol) and DCM (50 mL) was cooled down to 0° C. DBU (127 µL, 0.95 mmol) was added and the mixture was stirred at room temperature for 1 h. The mixture was concentrated. Silica gel column chromatography (2:1 hexanes-EtOAc) afforded the disaccharide donor 3 as a white solid (650 mg, 75%).

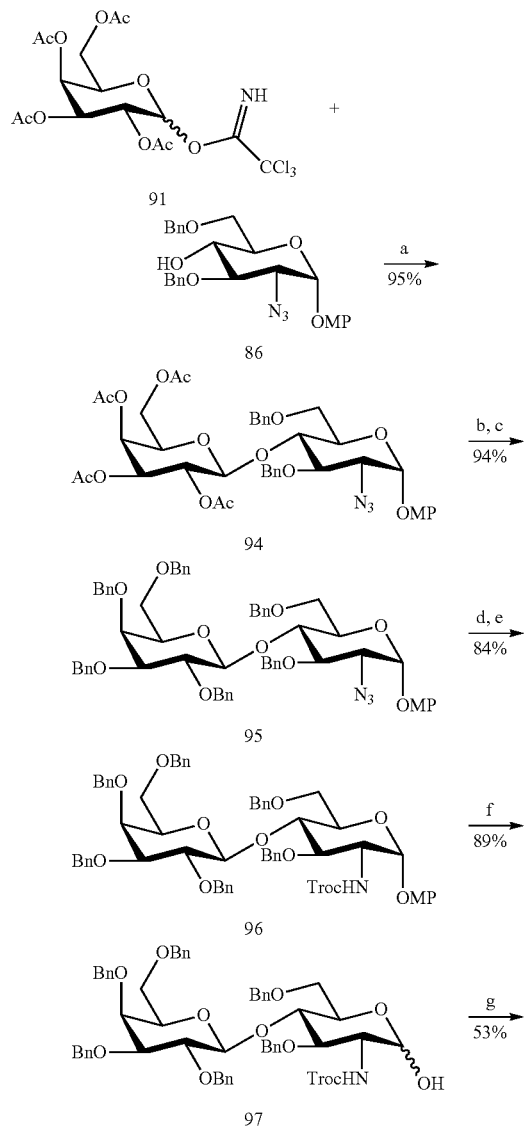

Scheme 23. Synthesis of disaccharide donor 2

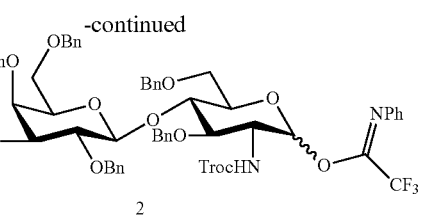

Reagents: a) TfOH, DCM, MS-4Å, -70° C. to -20° C., 1 h; b) NaOMe, DCM/MeOH, rt, 2 h; c) BnBr, NaH, DMF, rt, 2 h; d) PMe$_3$(1M), NaOH, THF/H$_2$O, rt, overnight; e) TrocCl, solid NaHCO$_3$, THF, 4 h; f) CAN, CH$_3$CN/H$_2$O, rt, 2 h; e) CF$_3$C(NPh)Cl, DBU, DCM, rt, 1 h.

Imidate donor 91 (644 mg, 1.31 mmol), acceptor 86 (450 mg, 0.92 mmol), molecular sieve MS-4 Å and DCM (40 mL) was stirred at room temperature for 30 min. The mixture was cooled to −70° C., followed by addition of TfOH (23 µL, 0.26 mmol). The reaction mixture was stirred for 1 hour from −70 to −20° C. and then was quenched with Et$_3$N (0.05 mL). The mixture was diluted with DCM (100 mL), washed with a saturated aqueous solution of NaHCO$_3$, H$_2$O and then dried over Na$_2$SO$_4$, filtered and concentrated. Silica gel column chromatography (2:1 hexanes-EtOAc) afforded 94 as a white solid (716 mg, 95%). $^1$H-NMR (500 MHz, CDCl$_3$): δ 1.96 (s, 3H, Ac), 1.98 (s, 3H, Ac), 2.02 (s, 3H, Ac), 2.12 (s, 3H, Ac), 3.51 (dd, 1H, J=10.0, 4.0 Hz, H-2), 3.56-3.59 (m, 1H, H-6b), 3.62-3.64 (m, 1H, H-5), 3.77-3.81 (m, 4H, H-6a, MP), 3.86-3.89 (m, 2H, H-6a', H-6b'), 3.99-4.03 (m, 1H, H-4), 4.08-4.17 (m, 2H, H-3, H-5'), 4.42 (d, 1H, J=11.5 Hz, Bn), 4.47 (d, 1H, J=9.0 Hz, H-1'), 4.78-4.83 (m, 3H, H-3', Bn), 5.13-5.16 (m, 2H, H-2', Bn), 5.28 (d, 1H, J=3.0 Hz, H-4'), 5.46 (d, 1H, J=4.0 Hz, H-1), 6.84-6.87 (m, 2H), 7.06-7.09 (m, 2H), 7.29-7.32 (m, 1H), 7.35-7.44 (m, 7H), 7.48-7.50 (m, 2H); $^{13}$C-NMR (75 MHz, CDCl$_3$): δ 20.7, 20.8 (×2), 21.0, 55.8, 60.7, 62.9, 67.0, 67.5, 69.7, 70.7, 71.2 (×2), 73.9, 75.3, 77.8, 77.9, 97.7, 100.2, 114.9, 118.1, 127.9, 128.2, 128.4, 128.5, 128.6, 129.0, 137.6, 138.5, 150.7, 155.6, 169.3, 170.2, 170.3, 170.4.

Compound 94 (710 mg, 0.86 mmol) was dissolved in DCM/MeOH (10 mL each). NaOMe (30%, 0.29 mL, 5.2 mmol) was added to the solution and the mixture was stirred at room temperature for 2 h. The mixture was neutralized by conc. HCl until the pH was around 7 and then concentrated and dried under vacuum. The obtained residue was dissolved in DMF (20 mL) and the solution was cooled to 0° C. NaH (210 mg, 60% NaH in mineral oil, 5.2 mmol) was added in portions, followed by addition of Benzyl bromide (0.51 mL, 4.3 mmol). The mixture was stirred at room temperature for 2 h and then quenched by EtOH. The mixture was diluted with EtOAc (100 mL) and was washed with saturated NaHCO$_3$, water, and then the organic layer was dried over Na$_2$SO$_4$, filtered and concentrated. Silica gel column chromatography (5:1 hexane-EtOAc) afforded compound 95 as a white solid (820 mg, 94% for 2 steps). $^1$H-NMR (500 MHz, CDCl$_3$): δ 3.46-3.51 (m, 3H, H-5, H-6b, H-6b'), 3.56 (dd, 1H, J=10.0, 3.5 Hz, H-2), 3.64-3.67 (m, 2H, H-6a, H-6a'), 3.88 (br, 3H, MP), 3.93 (d, 1H, J=7.5 Hz, H-2'), 4.00-4.03 (m, 2H, H-4, H-5'), 4.05 (d, 1H, J=2.5 Hz, H-4'), 4.18-4.27 (m, 2H, H-3, H-3'), 4.36 (d, 1H, J=12.0 Hz, Bn), 4.46-4.50 (m, 3H, H-1', Bn), 4.67-4.71 (m, 2H, Bn), 4.81-4.87 (m, 3H, Bn), 4.90-4.98 (m, 2H, Bn), 5.13 (d, 1H, J=11.5 Hz, Bn), 5.33 (d, 1H, J=10.5 Hz, Bn), 5.52 (d, 1H, J=3.5 Hz, H-1), 6.95-6.97 (m, 2H), 7.20-7.22 (m, 2H), 7.28-7.49 (m, 28H), 7.55-7.56 (m, 2H); $^{13}$C-NMR (75 MHz, CDCl$_3$): δ 55.5, 62.6, 67.6, 68.0, 69.7, 71.2, 72.5, 73.0, 73.2, 73.3, 73.6, 74.7, 75.2, 75.3, 76.4, 76.6, 79.9, 82.3, 97.7, 102.7, 114.6, 118.1, 127.2, 127.3, 127.4, 127.5 (×3), 127.6, 127.7, 127.8, 127.9, 128.1 (×2), 128.2, 128.3 (×2), 137.9, 138.0, 138.4 (×2), 138.6, 138.9, 150.6, 155.3.

Compound 95 (800 mg, 0.79 mmol), 1 M PMe$_3$ in THF (3.94 mL, 3.95 mmol), 1 M NaOH (2.1 mL, 2.1 mmol) and THF/H$_2$O (40 mL/10 mL) was stirred at room temperature overnight. The mixture was concentrated and the resulting residue was diluted with DCM (100 mL). The mixture was neutralized by conc. HCl until the pH was around 7. The mixture was concentrated and dried under vacuum. The resulting residue and solid NaHCO$_3$ (130 mg, 1.58 mmol) were put into THF (20 mL) and then 2,2,2-Trichloroethyl chloroformate (0.127 mL, 0.95 mmol) was added to the solution. The mixture was stirred at room temperature under N$_2$ for 4 hours and filtered. The filtrate was concentrated and then diluted with DCM (100 mL). The mixture was washed with water, brine, and then the organic layer was dried over Na$_2$SO$_4$, filtered and concentrated. Silica gel column chromatography (4:1 hexane-EtOAc) afforded compound 96 as a white solid (769 mg, 84% for two steps). $^1$H-NMR (500 MHz, CDCl$_3$): δ 3.27-3.31 (m, 3H, H-5, H-6b, H-6b'), 3.36-3.40 (m, 1H, H-6a), 3.45-3.47 (m, 1H, H-6a'), 3.68-3.71 (m, 4H, H-2', MP), 3.75-3.78 (m, 2H, H-4, H-5'), 3.82 (br, 1H, H-4'), 3.99-4.04 (m, 2H, H-3, H-3'), 4.15 (d, 1H, J=12.0 Hz, Bn), 4.24-4.29 (m, 3H, H-2, Bn), 4.43-4.46 (m, 2H, H-1', Bn), 4.53-4.75 (m, 7H, Bn, Troc), 4.86 (d, 1H, J=11.5 Hz, Bn), 5.01 (d, 1H, J=11.5 Hz, Bn), 5.07 (d, 1H, J=9.5 Hz, Bn), 5.36 (d, 1H, J=3.0 Hz), H-1), 6.72-6.73 (m, 2H), 6.92-6.94 (m, 2H), 7.13-7.25 (m, 30H); $^{13}$C-NMR (75 MHz, CDCl$_3$): δ 54.7, 55.6, 67.8, 68.1, 71.4, 72.5, 73.0, 73.1, 73.4, 73.6, 74.4, 74.6 (×2), 75.3, 77.9, 80.0, 82.4, 95.4, 97.3, 102.8, 114.6, 127.2, 118.1, 127.2, 127.3, 127.4, 127.5 (×2), 127.6, 127.7, 127.8 (×2), 128.0, 128.1, 128.3 (×2), 128.4, 138.0, 138.1, 138.4, 138.7, 138.9, 139.0, 150.4, 154.2, 155.3.

96 (1.1 g, 0.95 mmol) was dissolved in a mixture of CH$_3$CN//H$_2$O (30 mL/7.5 mL). Ceric ammonium nitrate (1.55 g, 2.85 mmol) was added to the solution at 0° C. and then the mixture was stirred at room temperature under N$_2$ for 2 h. The mixture was concentrated to dryness and the residue was diluted with DCM (100 mL) and the organic phase was washed with H$_2$O and then dried over Na$_2$SO$_4$, filtered and the solvents were removed in vacuum. Silica gel column chromatography (2.5:1 hexanes-EtOAc) afforded the corresponding hemiacetal 97 (890 mg, 89%). Compound 97, N-phenyltrifluoroacetimidoyl chloride (0.68 mL, 4.22 mmol) and DCM (40 mL) was cooled down to 0° C. DBU (126 μL, 0.95 mmol) was added and the mixture was stirred at room temperature for 1 h. The mixture was concentrated. Silica gel column chromatography (3:1 hexanes-EtOAc) afforded the corresponding imidate 2 as a white solid (550 mg, 53%).

Scheme 24. Synthesis of Heptasaccharide acceptors 23 and 28.

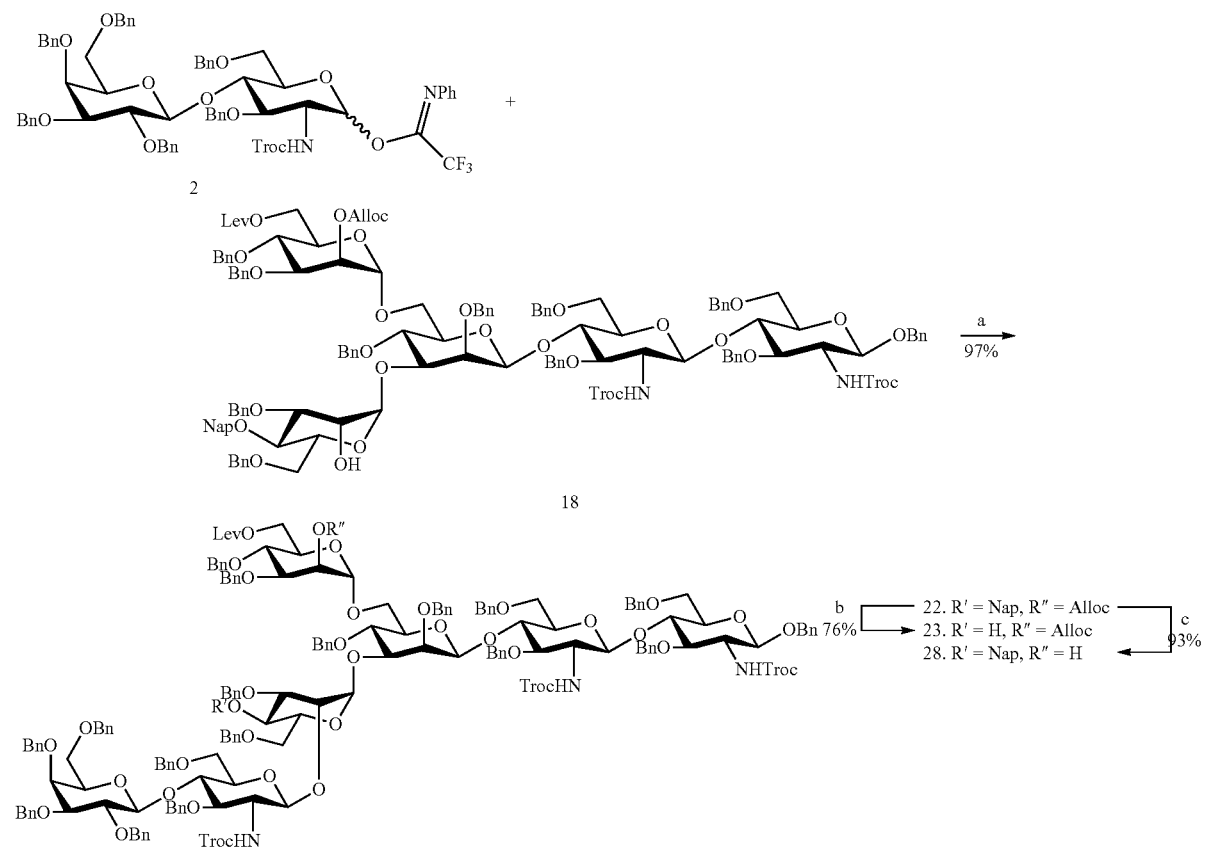

Reagents: a) TfOH, DCM, MS-4Å, -60° C. to -20° C., 1 h; b) DDQ, DCM/H$_2$O, rt, 3 h; c) Pd(PPh$_3$)$_4$, THF/H$_2$O, rt, overnigt Donor 2 (468 mg, 0.38 mmol), pentasaccharide acceptor 18 (475 mg, 0.19 mmol), molecular sieve MS-4 Å and DCM (45 mL) was stirred at room temperature for 30 min. The mixture was cooled to −60° C., followed by addition of TfOH (6.7 µL, 0.076 mmol). The reaction mixture was stirred for 1 hour from −60 to −20° C. and then was quenched with Et₃N (0.01 mL). The mixture was diluted with DCM (100 mL), washed with a saturated aqueous solution of NaHCO₃, H₂O and then dried over Na₂SO₄, filtered and concentrated. Silica gel column chromatography (2.5:1:1 hexanes-EtOAc-DCM) afforded 22 as a white solid (650 mg, 97%). ¹H-NMR (600 MHz, CDCl₃): δ 2.12 (s, 3H, Lev), 2.46-2.50 (m, 2H, Lev), 2.58-2.64 (m, 2H, Lev), 3.03-3.11 (m, 3H), 3.32-3.43 (m, 9H), 3.50-3.66 (m, 13H), 3.73-3.75 (m, 2H), 3.43-3.45 (m, 1H), 3.81-3.85, (m, 4H), 3.87-3.99 (m, 7H), 4.08-4.10 (m, 3H), 4.21-4.28 (m, 4H), 4.33-4.66 (m, 30H), 4.69-4.77 (m, 6H), 4.80-4.90 (m, 8H), 4.96-5.08 (m, 6H), 5.13 (br, 1H), 5.23 (d, 1H, J=10.2 Hz), 5.30-5.33 (m, 1H), 5.82-5.89 (m, 1H, Alloc), 7.11-7.36 (m, 84H), 7.42-7.43 (m, 2H), 7.47-7.49 (m, 2H), 7.62 (br, 1H), 7.74-7.76 (m, 2H), 7.82-7.85 (m, 1H); ¹³C-NMR (125 MHz, CDCl₃): δ 27.8, 29.7, 37.8, 56.3, 56.6, 57.4, 60.3, 63.1, 66.7, 68.1, 68.2, 68.3, 68.4, 68.6, 69.8, 70.0, 70.5, 70.8, 71.2, 71.8, 72.5, 72.7, 72.9, 73.0, 73.1 (×2), 73.4 (×2), 73.5, 73.6 (×2), 73.8, 74.2 (×2), 74.3 (×2), 74.5, 74.6, 74.8 (×2), 75.1, 76.2, 76.5, 77.7, 77.8, 78.1, 78.4, 78.6, 79.8, 80.3, 82.3, 95.5, 95.6, 95.7, 97.3, 99.5, 99.6, 99.9, 100.2, 101.1, 102.7, 118.9, 125.6, 125.9, 126.0 126.2, 126.3, 127.1, 127.3 (×3), 127.4 (×2), 127.5 (×2), 127.6 (×4), 127.7 (×2), 127.8 (×3), 127.9 (×2), 128.0 (×3), 128.1 (×2), 128.2 (×3), 128.3 (×3), 128.4, 128.5, 128.6, 131.4, 132.8, 133.2, 136.1, 137.2, 137.8 (×2), 137.9, 138.0, 138.1 (×2), 138.2, 138.4 (×2), 138.6, 138.7 (×2), 138.9, 153.8 (×2), 154.2, 172.2, 206.7. gHMQC (without ¹H decoupling): ¹J$_{C1,H1}$=173.7, 171.6, 164.5, 162.1, 161.1, 160.9, 159.1 Hz.

Heptasaccharide 22 (100 mg, 28.3 µmol) was dissolved in a mixture of DCM//H₂O (6 mL/0.6 mL) and the solution was cooled to 0° C. DDQ (7.7 mg, 34.0 µmol) was added to the solution and the mixture was stirred at room temperature under N₂ for 3 h. The mixture was diluted with DCM (30 mL) and the organic phase was washed with H₂O until the solution became colorless. The organic phase was dried over Na₂SO₄, filtered and the solvents were removed in vacuum. Silica gel column chromatography (2.5:1:1 hexanes-EtOAc-DCM) afforded acceptor 23 (72.7 mg, 76%). ¹H-NMR (600 MHz, CDCl₃): δ 2.02 (s, 3H, Lev), 2.23 (br, 1H, OH), 2.35-2.38 (m, 2H, Lev), 2.51-2.54 (m, 2H, Lev), 2.91-2.93 (m, 1H), 2.98-2.99 (m, 2H), 3.25-3.32 (m, 8H), 3.40-3.57 (m, 13H), 3.62-3.74 (m, 7H), 3.77-3.89 (m, 5H), 3.95 (br, 1H), 3.97-4.00 (m, 3H), 4.03-4.05 (m, 1H), 4.14-4.32 (m, 11H), 4.34-4.40 (m, 5H), 4.43-4.52 (m, 15H), 4.59-4.64 (m, 6H), 4.66-4.73 (m, 4H), 4.75-4.79 (m, 5H), 4.84-4.88 (m, 4H), 4.96-5.02 (m, 3H), 5.12 (d, 1H, J=10.8 Hz), 5.20-5.22 (m, 1H), 5.72-5.79 (m, 1H, Alloc), 6.98-7.01 (m, 3H), 7.06-7.25 (m, 80H), 7.32-7.33 (m, 2H); ¹³C-NMR (125 MHz, CDCl₃): δ 27.9, 29.8, 37.9, 56.4, 56.6, 57.5, 63.1, 66.8, 68.2, 68.3, 68.4, 68.5, 68.7, 69.9, 70.2, 70.5, 70.9, 71.3, 71.9, 72.6, 72.7, 73.0, 73.1, 73.4, 73.5, 73.6, 73.7, 73.9, 74.2, 74.3, 74.4, 74.6 (×3), 74.8, 75.1 (×2), 75.2, 76.2, 76.7, 76.8, 77.7, 77.9, 78.5, 79.9, 80.0, 82.4, 95.6, 95.7, 97.4, 99.6, 99.9, 100.3, 101.0, 102.9, 119.0, 126.1, 127.2, 127.3, 127.4 (×5), 127.5 (×3), 127.7 (×3), 127.8, 127.9, 128.0 (×3), 128.1, 128.2 (×3), 128.3 (×4), 128.4 (×2), 128.5 (×2), 128.6 (×2), 131.4, 137.3, 137.9 (×3), 138.0 (×3), 138.2, 138.3, 138.4, 138.5, 138.6, 138.7, 138.9 (×2), 139.0 (×2), 153.9 (×2), 154.3, 172.2, 206.7.

Heptasaccharide 22 (200 mg, 56.7 µmol) was dissolved in a mixture of THF//H₂O (20 mL/2 mL). Palladium-tetrakis (triphenylphosphine) (32.7 mg, 28.4 µmol) was added to the solution and then the mixture was stirred at room temperature overnight. The mixture was concentrated and then the residue was co-evaporated with toluene (3×5 mL). The solvents were removed in vacuum. Silica gel column chromatography (2:1 hexanes-EtOAc) afforded acceptor 28 as a white solid (182 mg, 93%). ¹H-NMR (600 MHz, CDCl₃): δ 2.04 (s, 3H, COCH₃), 2.30 (s, 3H, SPhCH₃), 3.04-3.05 (m, 1H), 3.17 (dd, 1H, J=3.6, 10.2 Hz, H-2'), 3.37-3.40 (m, 1H), 3.64-3.80 (m, 9H), 4.01-4.02 (m, 2H), 4.43-4.45 (m, 1H), 4.52 (s, 2H), 4.68-4.90 (m, 4H), 4.74 (d, 1H, J=9.6 Hz, H-1), 5.32 (t, 1H, J=9.6 Hz, H-2), 5.63 (d, 1H, J=3.6 Hz, H-1'), 6.89-6.90 (m, 2H), 7.03-7.05 (m, 2H), 7.14-7.48 (m, 16H), 7.57-7.60 (m, 1H), 8.10-8.11 (m, 2H); ¹³C-NMR (150 MHz, CDCl₃): δ 20.7, 21.1, 55.2, 62.5, 62.6, 68.2, 70.4, 70.8, 72.1, 72.7, 73.3, 74.6, 75.3, 78.9 (×2), 85.1, 85.9, 97.3, 113.7, 127.6, 127.8, 128.0, 128.1 (×2), 128.2, 128.5 (×2), 129.3, 129.5, 129.6, 129.8, 130.0, 133.3, 133.6, 137.2, 137.8, 138.3, 159.1, 165.1, 172.1.

Scheme 25. Synthesis of Nonasaccharide acceptor 25.

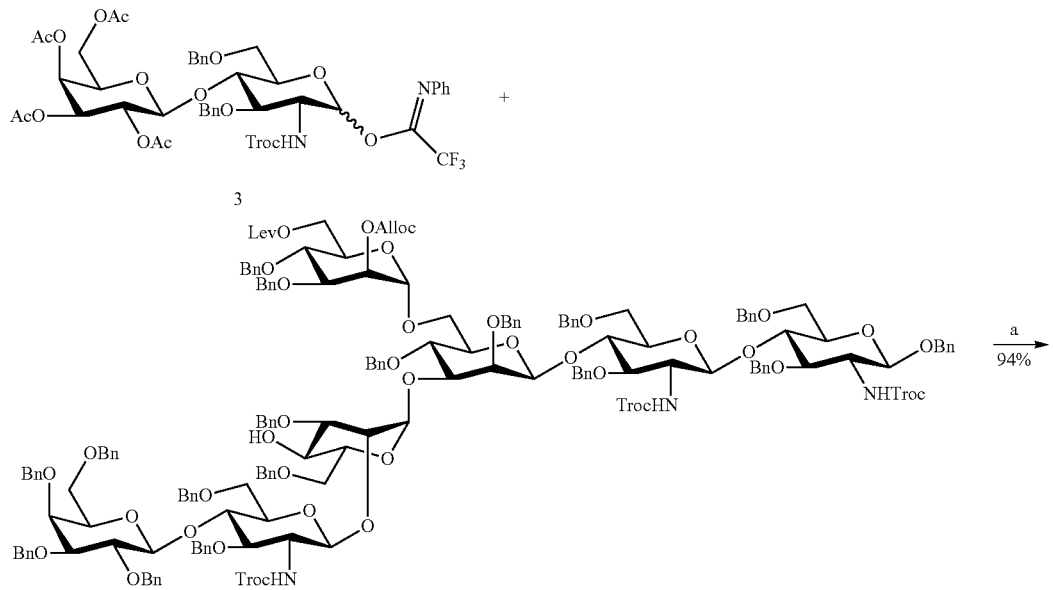

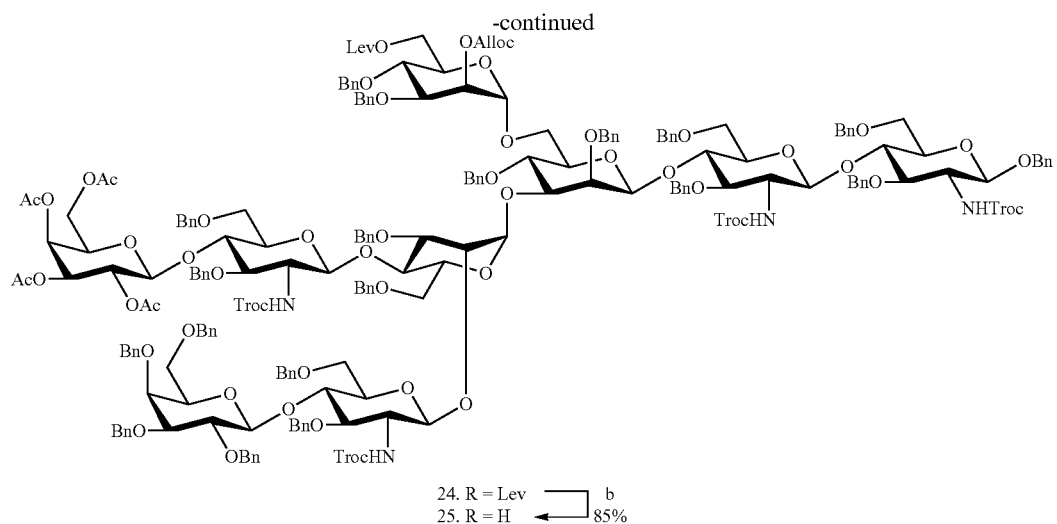

24. R = Lev ⎤ b
25. R = H ⎦ 85%

Reagents: a) TfOH, DCM, MS-4Å, -60° C. to -20° C., 1 h; b) NH₂NHOAc, DCM/MeOH, rt, 5 h.

Disaccharide donor 3 (33 mg, 31.8 μL), Heptasaccharide acceptor 23 (54 mg, 15.9 μL), molecular sieve MS-4 Å and DCM (10 mL) were stirred at room temperature for 30 min. The mixture was cooled to −60° C., followed by addition of TfOH (6.7 μL, 0.076 mmol). The reaction mixture was stirred for 1 hour from −60 to −20° C. and then was quenched with Et₃N (0.01 mL). The mixture was diluted with DCM (100 mL), washed with a saturated aqueous solution of NaHCO₃, H₂O and then dried over Na₂SO₄, filtered and concentrated. Silica gel column chromatography (2:1:1 hexanes-EtOAc-DCM) afforded 24 as a white solid (63.2 mg, 94%). $^1$H-NMR (600 MHz, CDCl₃): δ 1.87 (s, 3H, Ac), 1.88 (s, 3H, Ac), 1.89 (s, 3H, Ac), 2.00 (s, 3H, Ac), 2.02 (s, 3H, Lev), 2.738 (br, 2H, Lev), 2.51-2.52 (m, 2H, Lev), 2.88-3.04 (m, 4H), 3.16-3.55 (m, 28H), 3.62-3.66 (m, 4H), 3.73-4.03 (m, 18H), 4.15-4.17 (m, 4H), 4.22-4.79 (m, 47H), 4.83-5.02 (m, 9H), 5.11-5.15 (m, 2H), 5.50-5.23 (m, 1H), 5.73-5.78 (m, 1H, Alloc), 6.93-7.39 (m, 95H); $^{13}$C-NMR (125 MHz, CDCl₃): δ 20.5, 20.6, 20.9, 27.8, 29.6 29.8, 37.8, 56.3, 57.0, 57.4, 57.7, 60.5, 63.1, 66.7, 67.4, 68.1, 68.3, 68.6, 69.2, 69.8, 70.3, 70.5, 70.7, 71.3, 71.8, 71.9, 72.5, 72.7, 72.9, 73.1 (×2), 73.2, 73.3, 73.4, 73.5, 73.6, 73.7, 74.1, 74.2, 74.3, 74.4, 74.5, 74.6, 74.8, 75.1 (×2), 75.4, 76.6, 77.9, 78.3, 78.4, 78.6, 78.8, 79.9, 82.2, 95.6, 95.7, 97.3, 99.5 (×2), 100.2, 100.8, 101.1, 102.7, 118.9, 126.1, 127.0, 127.1, 127.2, 127.3 (×2), 127.4, 127.5 (×2), 127.6 (×2), 127.7 (×2), 127.8 (×2), 127.9, 128.0 (×2), 128.1 (×3), 128.2 (×3), 128.3 (×2), 128.4 (×2), 128.5 (×2), 128.6 (×2), 128.9, 129.4, 131.4, 137.2, 137.8 (×2), 138.0, 138.2 (×2), 138.3, 138.4, 138.6 (×2), 138.7, 139.0 (×2), 153.8 (×2), 154.2, 169.4, 170.0, 170.1 (×2), 172.2, 206.6. gHMQC (without $^1$H decoupling): $^1J_{C1,H1}$=173.7, 171.6, 164.5, 162.1, 161.1, 160.9, 159.1 Hz.

Nonasaccharide 24 (50 mg, 11.8 μmol) was dissolved in a mixture of DCM/MeOH (5 mL/0.5 mL). Hydrazine acetate (1.3 mg, 14.2 μmol) was added and then the mixture was stirred at room temperature under N₂ for 5 h. The mixture was concentrated to dryness. Silica gel column chromatography (2.5:1:1 hexanes-EtOAc-DCM) afforded acceptor 25 (41.3 mg, 85%). $^1$H-NMR (800 MHz, CDCl₃): δ 1.95 (s, 3H, Ac), 1.96 (s, 3H, Ac), 1.97 (s, 3H, Ac), 2.08 (s, 3H, Ac), 2.95-3.02 (m, 2H), 3.12-3.13 (m, 1H), 3.26-3.30 (m, 5H), 3.35-3.68 (m, 24H), 3.72-3.77 (m, 3H), 3.81-3.95 (m, 11H), 4.00-4.12 (m, 2H), 4.14-4.27 (m, 2H), 4.30-4.33 (m, 4H), 4.38-4.57 (m, 27H), 4.65-4.74 (m, 11H), 4.76-4.87 (m, 10H), 4.91-4.95 (m, 3H), 4.99-5.05 (m, 5H), 5.13 (br, 1H), 5.20-5.23 (m, 2H), 5.26-5.34 (m, 1H), 5.86-5.90 (m, 1H, Alloc), 7.03 (br, 2H), 7.08-7.35 (m, 91H), 7.45-7.46 (m, 2H).

Scheme 26. Synthesis of glucoseamine donor 4

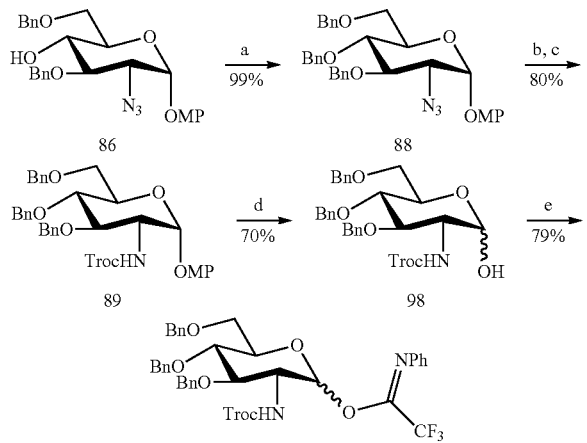

Reagents: a) BnBr, NaH, DMF, rt, 2 h; b) PMe₃(1M), NaOH, THF/H₂O, rt, overnight;
c) TrocCl, solid NaHCO₃, THF, 4 h; d) CAN, CH₃CN/H₂O, rt, 2 h;
e) CF₃C(NPh)Cl, DBU, DCM, rt, 1 h.

86 (400 mg, 0.81 mmol) was dissolved in DMF (20 mL) and the solution was cooled to 0° C. NaH (49 mg, 60% NaH in mineral oil, 13.8 mmol) was added in portions, followed by addition of Benzyl bromide (1.65 mL, 1.2 mmol). The mixture was stirred at room temperature for 2 h and then diluted with EtOAc (100 mL). The mixture was washed with saturated NaHCO$_3$, water, and then the organic layer was dried over Na$_2$SO$_4$, filtered and concentrated. Silica gel column chromatography (7:1 hexane-EtOAc) afforded compound 88 as a white solid (470 mg, 99%). $^1$H-NMR (500 MHz, CDCl$_3$): δ 3.62-3.65 (m, 1H, H-2), 3.78-3.80 (m, 1H, H-6b), 3.86 (br, 3H, MP), 3.91-3.93 (m, 1H, H-6a), 3.96-4.00 (m, 1H, H-4), 4.16-4.18 (m, 1H, H-5), 4.35-3.39 (m, 1H, H-3), 4.59 (d, 1H, J=12.0 Hz, Bn), 4.70-4.76 (m, 2H, Bn), 4.99 (d, 1H, J=11.0 Hz, Bn), 5.06-5.12 (m, 2H, Bn), 5.61 (d, 1H, J=2.5 Hz, H-1), 6.95-6.97 (m, 2H), 7.21-7.23 (m, 2H), 7.32-7.34 (m, 2H), 7.40-7.50 (m, 11H), 7.55-7.56 (m, 2H); $^{13}$C-NMR (75 MHz, CDCl$_3$): δ 55.4, 63.1, 68.1, 71.1, 73.3, 74.9, 75.3, 78.0, 80.0, 97.6, 114.5, 118.0, 127.6 (×2), 127.7 (×3), 127.9, 128.0, 128.2, 128.3 (×2), 137.6, 137.8 (×2), 150.3, 155.2.

88 (600 mg, 1.03 mmol), 1 M PMe$_3$ in THF (5.2 mL, 5.2 mmol), 1 M NaOH (2.68 mL, 2.7 mmol) and THF/H$_2$O (40 mL/10 mL) was stirred at room temperature overnight. The mixture was concentrated and the resulting residue was diluted with DCM (100 mL). The mixture was neutralized by conc. HCl until the pH was around 7. The mixture was concentrated and dried under vacuum. The resulting residue and solid NaHCO$_3$ (170 mg, 2.06 mmol) were put into THF (15 mL) and then 2,2,2-Trichloroethyl chloroformate (0.167 mL, 1.24 mmol) was added to the solution. The mixture was stirred at room temperature under N$_2$ for 4 hours and filtered. The filtrate was concentrated and then diluted with DCM (50 mL). The mixture was washed with water, brine, and then the organic layer was dried over Na$_2$SO$_4$, filtered and concentrated. Silica gel column chromatography (5:1:1 hexane-EtOAc-DCM) afforded compound 89 as a white solid (610 mg, 80% for two steps). $^1$H-NMR (500 MHz, CDCl$_3$): δ 3.73-3.75 (m, 1H, H-6b), 3.82 (br, 3H, MP), 3.85-3.87 (m, 1H, H-6a), 3.92-3.94 (m, 1H, H-5), 3.99-4.07 (m, 2H, H-3, H-4), 4.24-4.28 (m, 1H, H-2), 4.55 (d, 1H, J=12.0 Hz, Bn), 4.64 (d, 1H, J=11.0 Hz, Bn), 4.69-4.73 (m, 2H, Bn), 4.87-4.92 (m, 3H, Bn, Troc), 4.98 (d, 1H, J=11.0 Hz, Bn), 5.28 (d, 1H, J=9.5 Hz, NH), 5.55 (d, 1H, J=3.5 Hz, H-1), 6.88-6.89 (m, 2H), 7.07-7.09 (m, 2H), 7.26-7.29 (m, 2H), 7.34-7.43 (m, 13H); $^{13}$C-NMR (75 MHz, CDCl$_3$): δ 55.0, 55.5, 68.2, 71.4, 73.3, 74.6, 75.0, 75.2, 78.1, 80.1, 95.3, 97.4, 114.6, 118.0, 127.7, 127.8 (×3), 128.0, 128.3 (×2), 128.4, 137.8 (×2), 138.0, 150.0, 154.2, 155.3.

Compound 89 (100 mg, 0.136 mmol) was dissolved in a mixture of CH$_3$CN/H$_2$O (4 mL/1 mL). Ceric ammonium nitrate (225 mg, 0.408 mmol) was added to the solution at 0° C. and then the mixture was stirred at room temperature under N$_2$ for 2 h. The mixture was concentrated to dryness and the residue was diluted with DCM (50 mL) and the organic phase was washed with H$_2$O and then dried over Na$_2$SO$_4$, filtered and the solvents were removed in vacuum. Silica gel column chromatography (3:1 hexanes-EtOAc) afforded the corresponding hemiacetal 98 (60.2 mg, 70%). The obtained compound 98 (40 mg, 64 µmol), N-phenyltrifluoroacetimidoyl chloride (52 µL, 0.32 mmol) and DCM (5 mL) was cooled down to 0° C. DBU (9.6 µL, 64 µmol) was added and the mixture was stirred at room temperature for 1 h. The mixture was concentrated. Silica gel column chromatography (3:1 hexanes-EtOAc) afforded the corresponding imidate donor 4 as a white solid (40.3 mg, 70%).

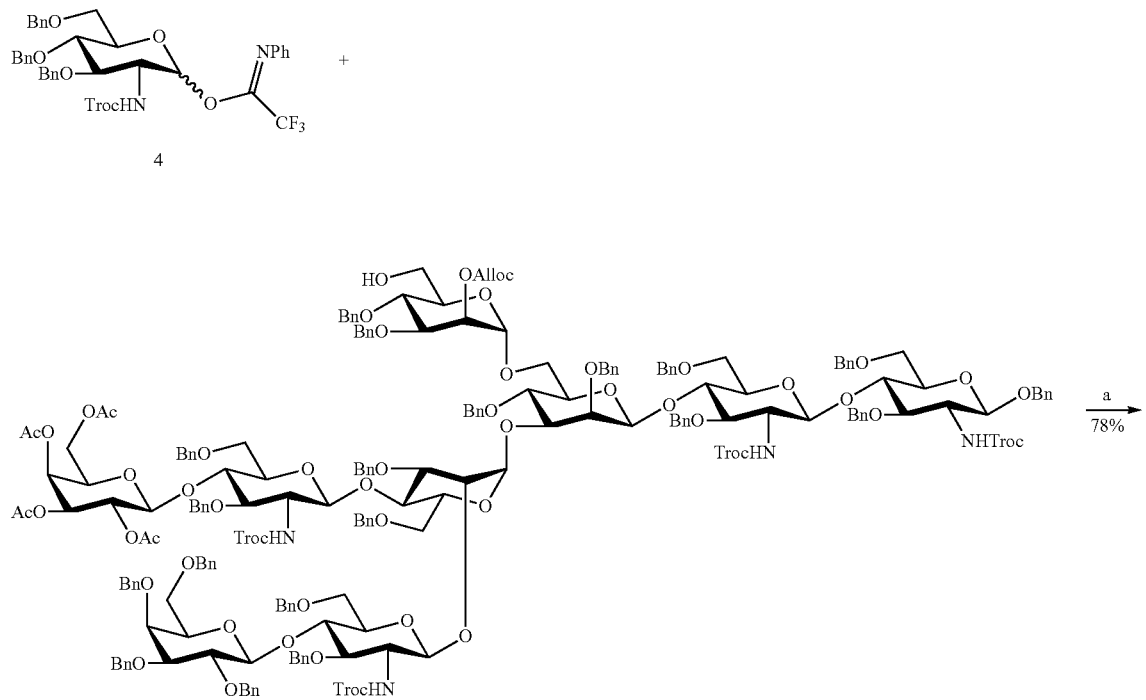

Scheme 27. Synthesis of decasaccharide 26.

-continued

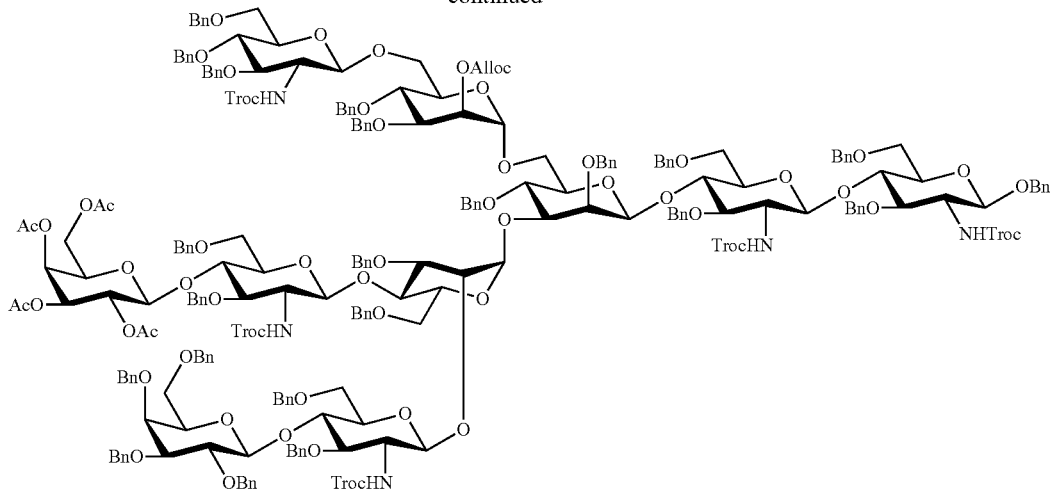

26

Reagents: a) TfOH, DCM, MS-4Å, −60° C. to −20° C., 1 h.

Glucosamine donor 4 (46.2 mg, 58.0 µL), nonasaccharide acceptor 25 (120 mg, 29 µL), molecular sieve MS-4 Å and DCM (8 mL) was stirred at room temperature for 30 min. The mixture was cooled to −60° C., followed by addition of TfOH (6.7 µL, 0.076 mmol). The reaction mixture was stirred for 1 hour from −60 to −20° C. and then was quenched with Et$_3$N (0.01 mL). The mixture was diluted with DCM (100 mL), washed with a saturated aqueous solution of NaHCO$_3$, H$_2$O and then dried over Na$_2$SO$_4$, filtered and concentrated. Silica gel column chromatography (2:1 hexanes-EtOAc) afforded decasaccharide 26 as a white solid (108 mg, 78%). $^1$H-NMR (600 MHz, CDCl$_3$): δ 1.94 (s, 3H, Ac), 1.96 (s, 3H, Ac), 1.97 (s, 3H, Ac), 2.08 (s, 3H, Ac), 2.97-3.00 (m, 1H), 3.10-3.23 (m, 3H), 3.29-3.60 (m, 27H), 3.66-3.75 (m, 7H), 3.82-3.99 (m, 18H), 4.09-4.24 (m, 6H), 4.30-4.37 (m, 8H), 4.44-4.86 (m, 51H), 4.91-5.05 (m, 8H), 5.09 (br, 1H), 5.18-5.19 (m, 1H), 5.22-5.27 (d, 1H, J=3.0 Hz), m, 1H), 5.28-5.31 (m, 1H), 5.79-5.85 (m, 1H), 7.01-7.37 (m, 108H), 7.47-7.48 (m, 2H); $^{13}$C-NMR (200 MHz, CDCl$_3$): δ 20.5, 20.6, 20.9, 29.7, 56.3, 57.0, 57.3, 57.5, 57.8, 60.5, 66.6, 66.7, 67.4, 67.6, 68.1, 68.3, 68.6, 68.9, 69.3, 69.7, 70.3, 70.5, 70.8, 71.2, 71.7, 72.0, 72.5, 72.8, 72.9, 73.1, 73.4, 73.9, 74.0, 74.2, 74.4, 74.5, 74.6, 74.8, 75.1, 75.5, 76.3, 76.6, 78.1, 78.3, 78.6, 78.9, 79.9, 80.5, 82.2, 95.6, 95.7, 97.4, 99.5 (×2), 97.3, 100.4, 100.9, 101.2, 102.7, 119.0, 127.1, 127.0, 127.1, 127.3 (×2), 127.4 (×2), 127.5, 127.6 (×2), 127.7 (×2), 127.8 (×2), 127.9, 128.0 (×2), 128.1 (×2), 128.2 (×2), 128.3 (×2), 128.4 (×2), 128.5 (×2), 128.6, 128.7, 131.4, 137.3, 137.8, 138.0 (×2), 138.2 (×2), 138.4, 138.6, 138.8, 139.0, 139.1, 153.8 (×2), 154.3, 169.4, 170.0, 170.1, 170.2. gHMQC (without $^1$H decoupling): $^1J_{C1,H1}$=173.7, 171.6, 164.5, 162.1, 161.1, 160.9, 159.1 Hz.

Scheme 28. Deprotection of Alloc to give compound 99.

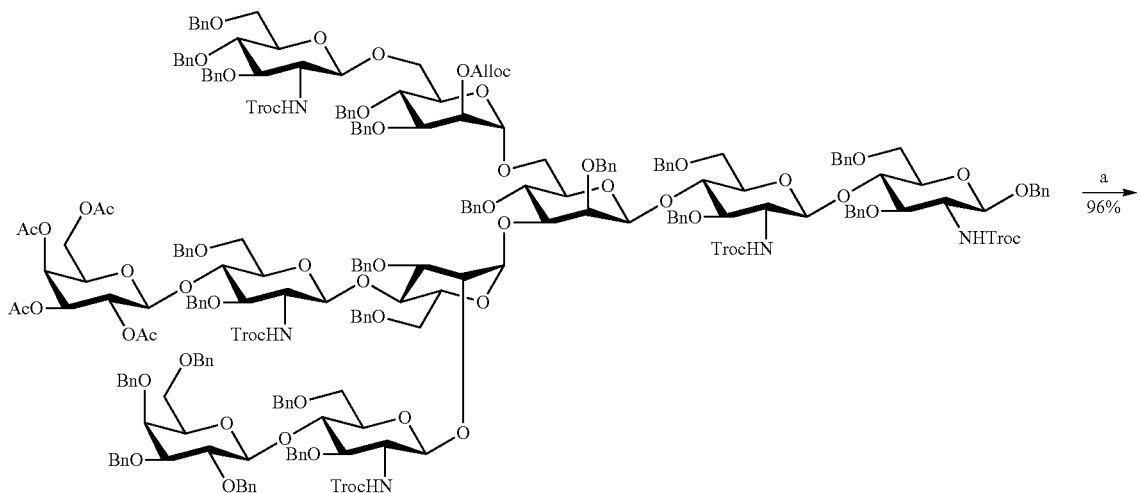

26

-continued

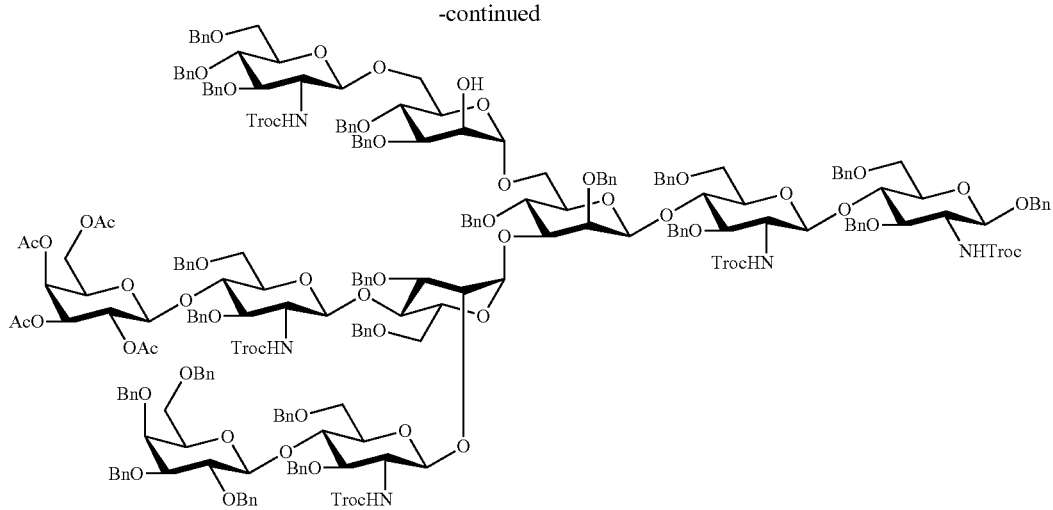

99

Reagents: a) Pd(PPh₃)₄, THF/H₂O, rt, overnight

Decasaccharide 26 (100 mg, 21.1 μmol) was dissolved in a mixture of THF//H₂O (20 mL/2 mL). Palladium-tetrakis (triphenylphosphine) (12.2 mg, 10.6 μmol) was added to the solution and then the mixture was stirred at room temperature overnight. The mixture was concentrated and then the residue was co-evaporated with toluene (3×5 mL). The solvents were removed in vacuum. Silica gel column chromatography (2:1 hexanes-EtOAc) afforded 99 as a white solid (94 mg, 96%). $^1$H-NMR (600 MHz, CDCl₃): δ 1.87 (s, 3H, Ac), 1.88 (s, 3H, Ac), 1.89 (s, 3H, Ac), 2.00 (s, 3H, Ac), 2.89-293 (m, 2H), 3.03-3.13 (m, 3H), 3.17-3.24 (m, 5H), 3.27-3.29 (m, 5H), 3.32-3.41 (m, 8H), 3.43-3.53 (m, 9H), 3.58-3.60 (m, 4H), 3.64-3.67 (m, 4H), 3.70-3.91 (m, 17H), 4.11-4.26 (m, 5H), 4.21-4.33 (m, 11H), 4.39-4.52 (m, 27H), 4.56-4.73 (m, 19H), 4.78 (d, 1H, J=12 Hz), 4.83-4.98 (m, 7H), 5.02-5.03 (m, 1H), 5.15 (d, 1H, J=3.6 Hz), 6.94-7.27 (m, 108H), 7.38-7.40 (m, 2H).

Scheme 29. Deproctection of NHTroc and Benzyl ethers to give Decasaccharide 27.

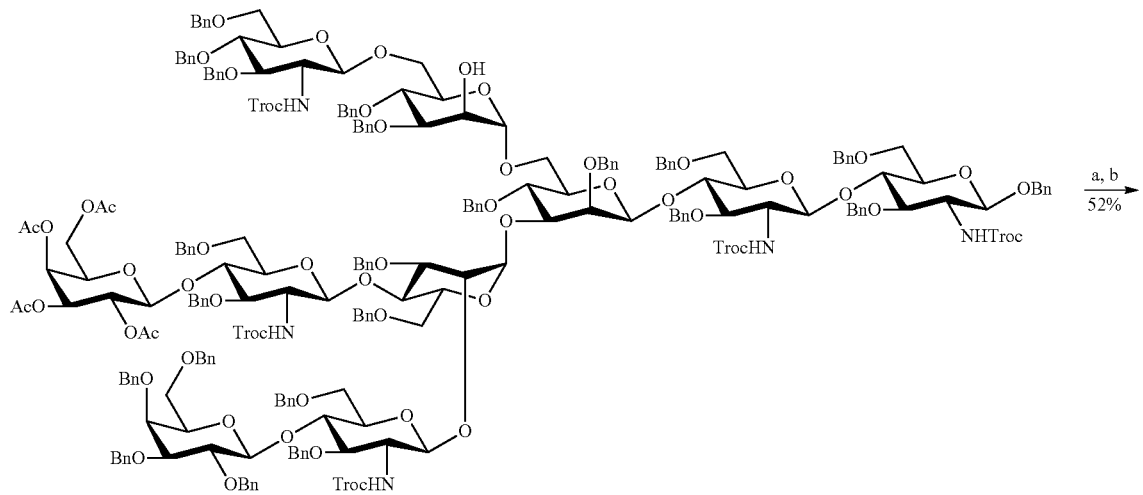

99

-continued

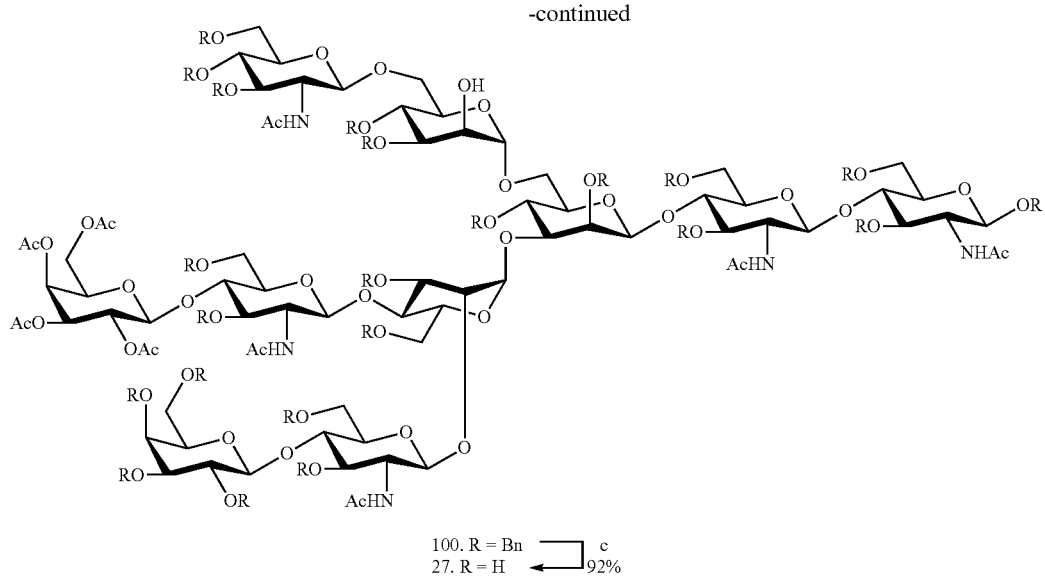

100. R = Bn ⎤ c
27. R = H ⎦ 92%

Reagents: a) Zn/AcOH, DCM/MeOH, rt, 2 h; b) Ac₂O, MeOH, rt, overnight; c) H₂, Pd(OH)₂, MeOH/H₂O, rt, overnight.

Compound 99 (90 mg, 19.3 μmol) was dissolved in MeOH (6 mL), AcOH (3 mL) and DCM (3 mL). Zn powder (0.25 g, 3.86 mmol) was added slowly at 0° C. and the mixture was stirred under $N_2$ at room temperature for 2 hour. The mixture was filtered and concentrated to dryness. The resulting residue was diluted with DCM (50 mL), washed with a saturated aqueous solution of $NaHCO_3$ until the pH was around 7 and then the organic layer was dried over $Na_2SO_4$ and filtered. The solvent was evaporated to dryness under vacuo without further purification. The mixture of the obtained solid, methanol (1 mL) and $Ac_2O$ (99 μL, 0.97 mmol) was stirred at room temperature overnight and then was quenched by adding one drop of water. The mixture was concentrated and then the residue was co-evaporated with toluene (3×5 mL). The solvents were removed in vacuum. Silica gel column chromatography (3:2 toluene-acetone) afforded the desired compound 100 (40 mg, 52% for 2 steps). The obtained compound 100 (27 mg) and $Pd(OH)_2$ (50 mg) in $MeOH/H_2O$ (8 mL/1 mL) was stirred under $H_2$ at room temperature for 36 h and then filtered. The filtrate was concentrated to dryness under vacuum and then diluted with $H_2O$ (15 mL). The aqueous phase was further washed with DCM (5 mL×3) and EtOAc (5 mL×3) and then the aqueous phase was dried under vacuum. The residue was re-dissolved in $H_2O$ (3 mL) and then was lyophilized to afford decasaccharide 27 as a white solid (12.5 mg, 92%).

Scheme 30. Synthesis of Nonasaccharide acceptor 30.

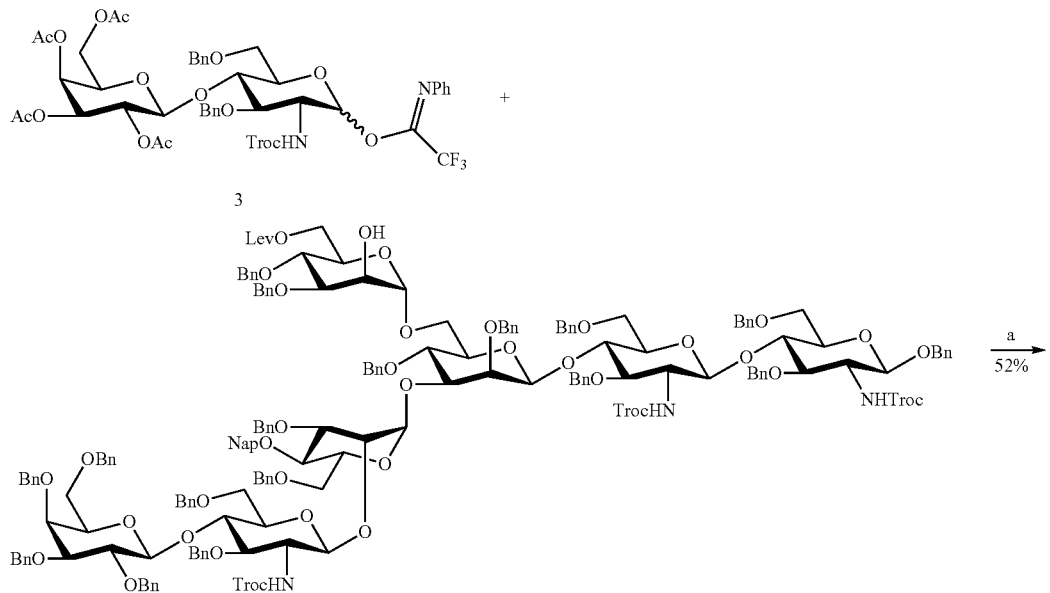

-continued

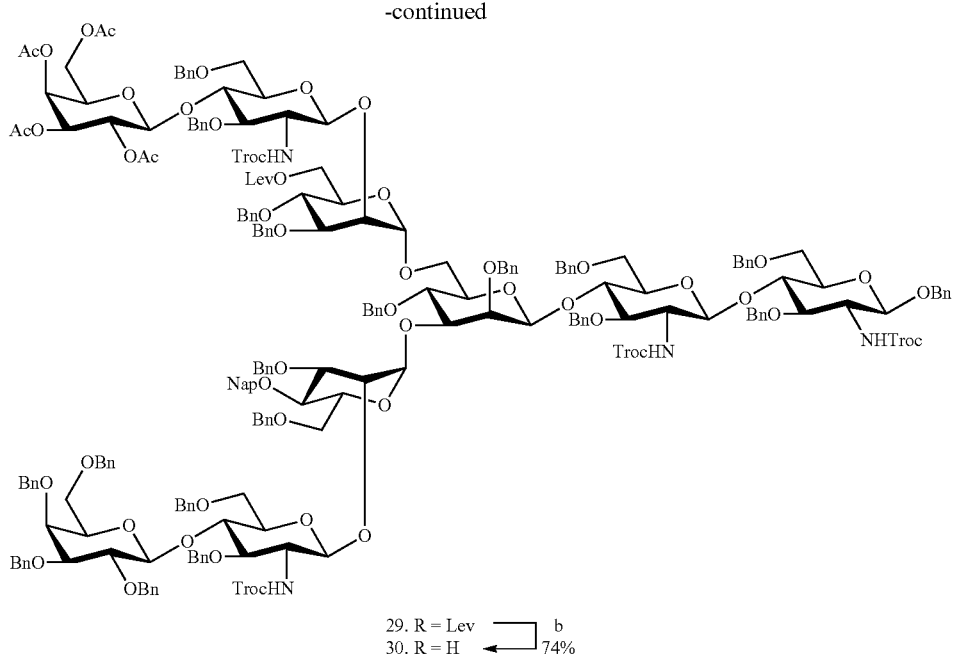

29. R = Lev ⎤ b
30. R = H  ⎦ 74%

Reagents: a) TfOH, DCM, MS-4Å, −70° C. to −20° C., 1 h; b) NH$_2$NHOAc, DCM/MeOH, rt, 5 h.

Disaccharide donor 3 (90 mg, 87 μL), heptasaccharide acceptor 28 (150 mg, 43.5 μL), molecular sieve MS-4 Å and DCM (20 mL) was stirred at room temperature for 30 min. The mixture was cooled to −70° C., followed by addition of TfOH (1.54 μL, 17.4 μmol). The reaction mixture was stirred for 1 hour from −70 to −20° C. and then was quenched with Et$_3$N (50 μL). The mixture was diluted with DCM (100 mL), washed with a saturated aqueous solution of NaHCO$_3$, H$_2$O and then dried over Na$_2$SO$_4$, filtered and concentrated. Silica gel column chromatography (2:1 hexanes-EtOAc) afforded nonasaccharide 29 as a white solid (97 mg, 52%). $^1$H-NMR (600 MHz, CDCl$_3$): δ 2.04 (s, 3H, COCH$_3$), 2.30 (s, 3H, SPhCH$_3$), 3.04-3.05 (m, 1H), 3.17 (dd, 1H, J=3.6, 10.2 Hz, H-2'), 3.37-3.40 (m, 1H), 3.64-3.80 (m, 9H), 4.01-4.02 (m, 2H), 4.43-4.45 (m, 1H), 4.52 (s, 2H), 4.68-4.90 (m, 4H), 4.74 (d, 1H, J=9.6 Hz, H-1), 5.32 (t, 1H, J=9.6 Hz, H-2), 5.63 (d, 1H, J=3.6 Hz, H-1'), 6.89-6.90 (m, 2H), 7.03-7.05 (m, 2H), 7.14-7.48 (m, 16H), 7.57-7.60 (m, 1H), 8.10-8.11 (m, 2H); $^{13}$C-NMR (150 MHz, CDCl$_3$): δ 20.7, 21.1, 55.2, 62.5, 62.6, 68.6, 70.4, 70.8, 72.1, 72.7, 73.3, 74.6, 75.3, 78.9 (×2), 85.1, 85.9, 97.3, 113.7, 127.6, 127.8, 128.0, 128.1 (×2), 128.2, 128.5 (×2), 129.3, 129.5, 129.6, 129.8, 130.0, 133.3, 133.6, 137.2, 137.8, 138.3, 159.1, 165.1, 172.1.

29 (88 mg, 20.5 μmol) was dissolved in a mixture of DCM/MeOH (5 mL/0.5 mL). Hydrazine acetate (2.3 mg, 24.6 μmol) was added and then the mixture was stirred at room temperature under N$_2$ for 5 h. The mixture was concentrated to dryness. Silica gel column chromatography (2:1 hexanes-EtOAc) afforded nonasaccharide acceptor 30 (63.8 mg, 74%). $^1$H-NMR (600 MHz, CDCl$_3$): δ 2.04 (s, 3H, COCH$_3$), 2.30 (s, 3H, SPhCH$_3$), 3.04-3.05 (m, 1H), 3.17 (dd, 1H, J=3.6, 10.2 Hz, H-2'), 3.37-3.40 (m, 1H), 3.64-3.80 (m, 9H), 4.01-4.02 (m, 2H), 4.43-4.45 (m, 1H), 4.52 (s, 2H), 4.68-4.90 (m, 4H), 4.74 (d, 1H, J=9.6 Hz, H-1), 5.32 (t, 1H, J=9.6 Hz, H-2), 5.63 (d, 1H, J=3.6 Hz, H-1'), 6.89-6.90 (m, 2H), 7.03-7.05 (m, 2H), 7.14-7.48 (m, 16H), 7.57-7.60 (m, 1H), 8.10-8.11 (m, 2H); $^{13}$C-NMR (150 MHz, CDCl$_3$): δ 20.7, 21.1, 55.2, 62.5, 62.6, 68.6, 70.4, 70.8, 72.1, 72.7, 73.3, 74.6, 75.3, 78.9 (×2), 85.1, 85.9, 97.3, 113.7, 127.6, 127.8, 128.0, 128.1 (×2), 128.2, 128.5 (×2), 129.3, 129.5, 129.6, 129.8, 130.0, 133.3, 133.6, 137.2, 137.8, 138.3, 159.1, 165.1, 172.1.

Scheme 31. Synthesis of decasaccharide 31.

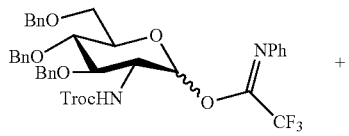

4

-continued

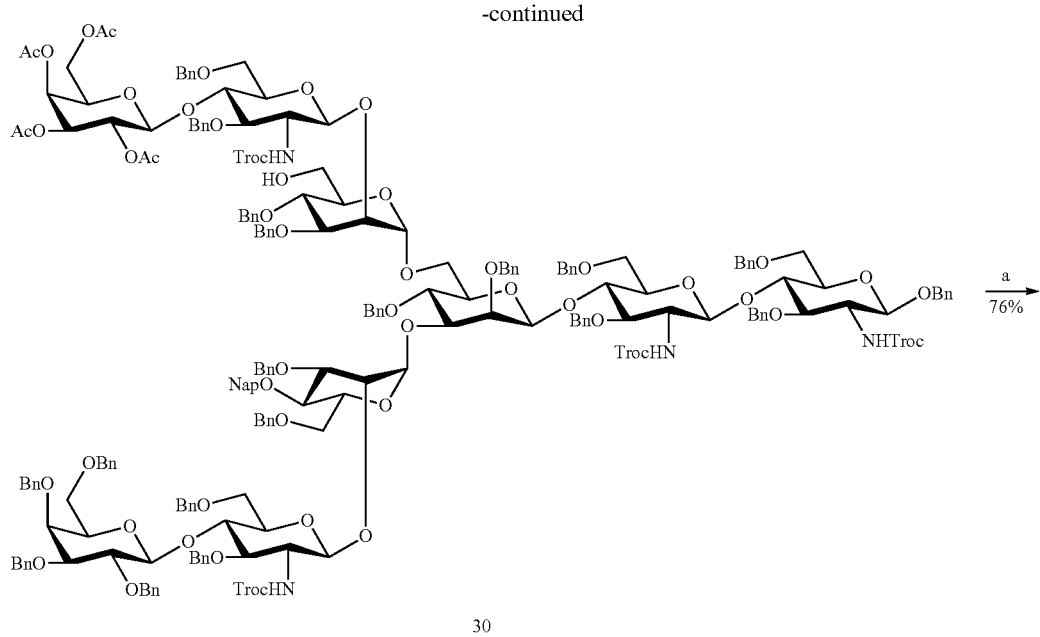

30

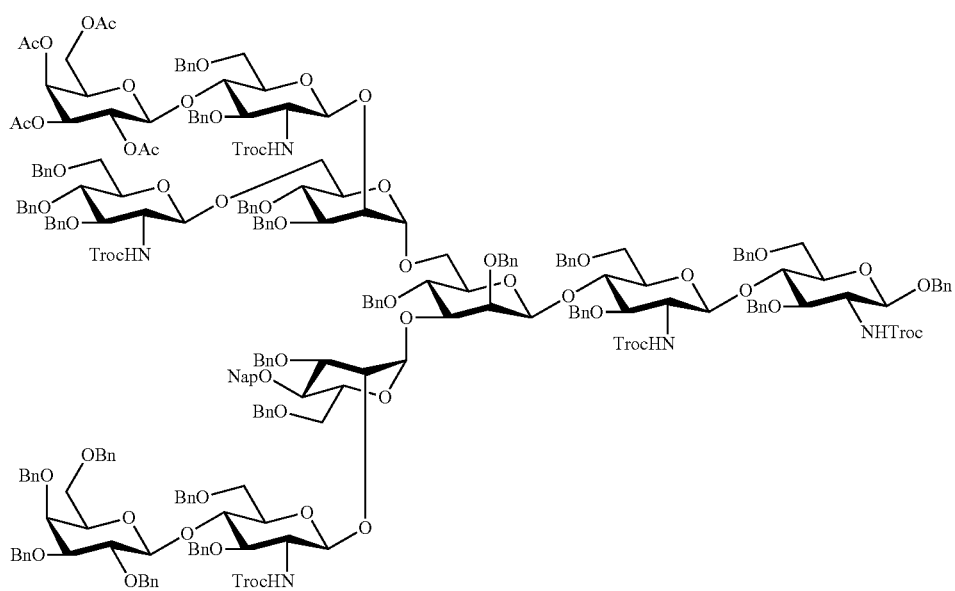

31

Reagents: a) TfOH, DCM, MS-4Å, -60° C. to -20° C., 1 h.

Glucosamine donor 4 (22.8 mg, 28.6 µmol), nonasaccharide acceptor 30 (60 mg, 14.3 µL), molecular sieve MS-4 Å and DCM (8 mL) was stirred at room temperature for 30 min. The mixture was cooled to −60° C., followed by addition of TfOH (5.72 µL, 0.5 µmol). The reaction mixture was stirred for 1 hour from −60 to −20° C. and then was quenched with $Et_3N$ (20 µL). The mixture was diluted with DCM (50 mL), washed with a saturated aqueous solution of $NaHCO_3$, $H_2O$ and then dried over $Na_2SO_4$, filtered and concentrated. Silica gel column chromatography (2:1 hexanes-EtOAc) afforded decasaccharide 31 as a white solid (52.3 mg, 76%). $^1$H-NMR (600 MHz, $CDCl_3$): δ 2.04 (s, 3H, $COCH_3$), 2.30 (s, 3H, $SPhCH_3$), 3.04-3.05 (m, 1H), 3.17 (dd, 1H, J=3.6, 10.2 Hz, H-2'), 3.37-3.40 (m, 1H), 3.64-3.80 (m, 9H), 4.01-4.02 (m, 2H), 4.43-4.45 (m, 1H), 4.52 (s, 2H), 4.68-4.90 (m, 4H), 4.74 (d, 1H, J=9.6 Hz, H-1), 5.32 (t, 1H, J=9.6 Hz, H-2), 5.63 (d, 1H, J=3.6 Hz, H-1'), 6.89-6.90 (m, 2H), 7.03-7.05 (m, 2H), 7.14-7.48 (m, 16H), 7.57-7.60 (m, 1H), 8.10-8.11 (m, 2H); $^{13}$C-NMR (150 MHz, $CDCl_3$): δ 20.7, 21.1, 55.2, 62.5, 62.6, 68.6, 70.4, 70.8, 72.1, 72.7, 73.3, 74.6, 75.3, 78.9 (×2), 85.1, 85.9, 97.3, 113.7, 127.6, 127.8, 128.0, 128.1 (×2), 128.2, 128.5 (×2), 129.3, 129.5, 129.6, 129.8, 130.0, 133.3, 133.6, 137.2, 137.8, 138.3, 159.1, 165.1, 172.1.

Scheme 32. Deproctection of NHTroc, Nap and Benzyl ethers to give Decasaccharide 32.

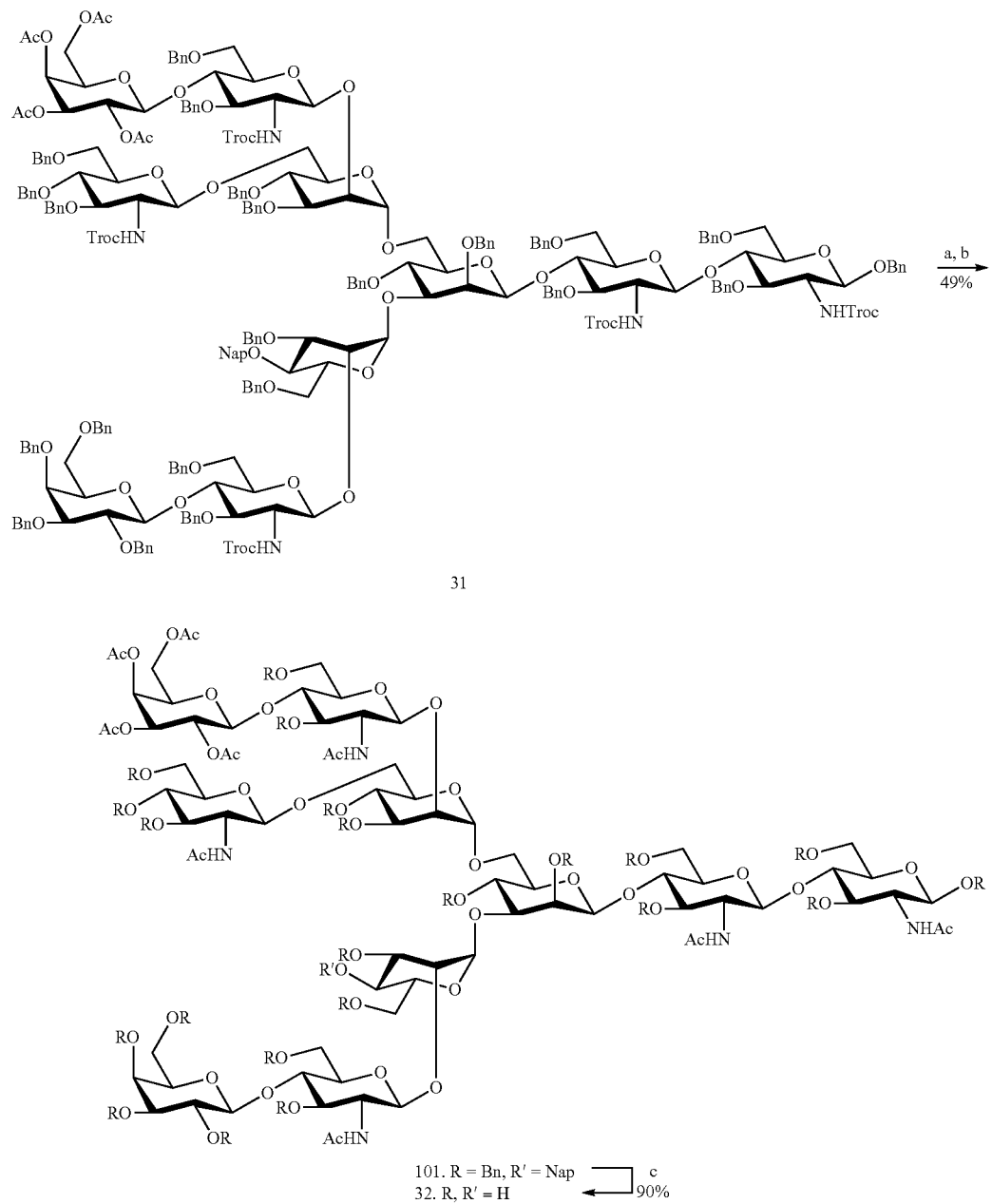

Reagents: a) Zn/AcOH, DCM/MeOH, rt, 2 h; b) Ac₂O, MeOH, rt, overnight; c) H₂, Pd(OH)₂, MeOH/H₂O, rt, 36 h.

Decasaccharide 31 (50 mg, 10.4 µmol) was dissolved in MeOH (3 mL), AcOH (1.5 mL) and DCM (1.5 mL). Zn powder (68 mg, 1.04 mmol) was added slowly at 0° C. and the mixture was stirred under $N_2$ at room temperature for 2 hour. The mixture was filtered and concentrated to dryness. The resulting residue was diluted with DCM (30 mL), washed with a saturated aqueous solution of $NaHCO_3$ until the pH was around 7 and then the organic layer was dried over $Na_2SO_4$ and filtered. The solvent was evaporated to dryness under vacuo without further purification. The mixture of the obtained solid, methanol (3 mL) and $Ac_2O$ (49 µL, 0.52 mmol) was stirred at room temperature overnight and then was quenched by adding one drop of water. The mixture was concentrated and then the residue was co-evaporated with toluene (3×5 mL). The solvents were removed in vacuum. Silica gel column chromatography (3:2 toluene-acetone) afforded the desired compound 101 (21 mg, 49% for 2 steps). Compound 101 (16.5 mg) and $Pd(OH)_2$ (30 mg) in MeOH/$H_2O$ (5 mL/0.6 mL) were stirred under $H_2$ at room temperature for 36 h and then filtered. The filtrate was concentrated to dryness under vacuum and then diluted with $H_2O$ (10 mL). The aqueous phase was further washed with DCM (5 mL×3) and EtOAc (5 mL×3) and then the aqueous phase was dried under vacuum. The residue was re-dissolved in $H_2O$ (2 mL) and then was lyophilized to afford 32 as a white solid (7.6 mg, 95%).

Scheme 33. Deproctection of acetyl esters to give Decasaccharide 49.

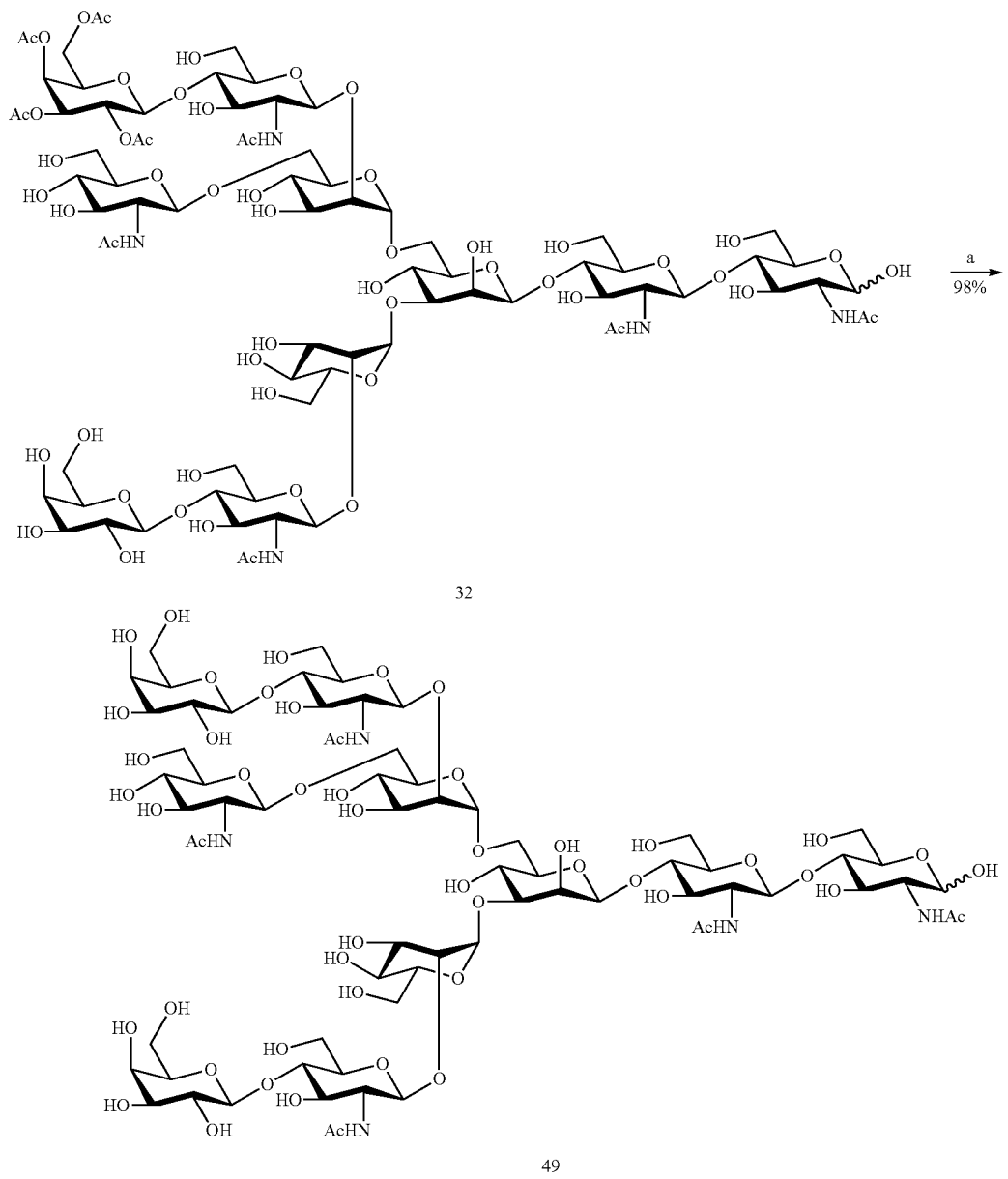

Reagents: a) NH₄OH, H₂O, rt, 3.5 h.

Decasaccharide 32 (3 mg, 1.5 μmol) was dissolved in H₂O (4 mL) and 28%-30% NH₄OH (0.4 mL) and the reaction mixture was mixed at room temperature for 3.5 hours. The completed reaction, as indicated by MALDI, was subjected to gel filtration on Sephadex G-25 (eluent 0.1M NH₄HCO₃). Fractions containing product were combined and lyophilized to yield decassacharide 49 (2.7 mg, 98%) as a white amorphous solid.

Enzymatic Syntheses

Enzymes used: HP-39 (β1-3GlcNAc Transferase, Activity=0.5 U/mL), GalT-1 (β1-4Galactosyl Transferase, Activity=3 U/mL), HPα1-3FucT (α1-3Fucosyl Transferase, Activity=1.055 U/mL), rST3Gal-III (α2-3Sialyl Transferase, Activity=1 U/mL), ST6Gal-I (α2-6Sialyl Transferase, Activity=1.777 U/mL Reactions were monitored by TLC (EtOH/H₂O/EtOAC/AcOH=5/2/2/0.1) or by MALDI-TOF MS.

Mono-Sialylation(α2-3) of compounds 27, 32, 46 and 54 to form 33, 41, 47 and 55 respectively.

A glycan (27, 32, 46 and 54) and CMP-Neu5Ac (2 eq) were dissolved in sodium cacodylate buffer (50 mM, pH 7.6) containing BSA (0.1%). CIAP (10 mU) and rST3Gal-III (5.56 mU/μmol substrate) were added to achieve a final concentration of glycan ranging from 2-5 mM. The resulting reaction mixture was incubated at 37° C. for 18 h. In case TLC or MALDI-TOF MS showed starting material remaining, additional CMP-Neu5Ac (1 eq), CIAP (10 mU) and rST3Gal-III (5.56 mU per 1 μmol of substrate) were added and incubated at 37° C. until no starting material could be detected. The reaction mixture was centrifuged and the supernatant subjected to gel filtration over Sephadex G-25 (eluent 0.1 M NH$_4$HCO$_3$). Fractions containing product as detected by MALDI-TOF MS, were combined and lyophilized to give the respective products 33, 41, 47 and 55 as white amorphous solids.

Bis-Fucosylation of compounds 34, 42, 47, 50 and 55 to form 35, 43, 48, 51 and 56 respectively:

A glycan (34, 42, 47, 50 or 55) and GDP-Fucose (2 eq per Fucose) were dissolved in Tris buffer (50 mM, pH 7.5) with MnCl$_2$ (10 mM). To this, CIAP (10 mU) and HPα1-3FucT (18 mU per 1 μmol of substrate) were added to achieve a final concentration of glycan ranging from 2-5 mM. The resulting mixture incubated at 37° C. for 18 h. In case TLC or mass analysis showed starting material or mono-fucosylated intermediate, additional GDP-Fucose (2 eq), CIAP (10 mU) and HPα1-3FucT (18 mU/μmol substrate) were added and incubated at 37° C. until no starting material or mono-fucosylated intermediate could be detected. The reaction mixture was centrifuged and the supernatant subjected to gel filtration on Sephadex G-25 (eluent 0.1 M NH$_4$HCO$_3$). Fractions containing product were combined and lyophilized to give the respective products 35, 43, 48, 51 or 56 as white amorphous solids.

Addition of Galactose to compounds 35, 37, 43, 45, 51 and 53 to form 36, 38, 44, 46, 52 and 54 respectively:

A glycan (35, 37, 43, 45, 51 or 53) and UDP-Galactose (2 eq) were dissolved in Tris buffer (50 mM, pH 7.5) with BSA (0.1%) and MnCl$_2$ (10 mM). To this, CIAP (10 mU) and GalT-1 (5.56 mU/μmol substrate) were added to achieve a final concentration of glycan ranging from 2-5 mM and incubated at 37° C. for 5 h. The resulting reaction mixture was centrifuged and the supernatant subjected to gel filtration on Sephadex G-25 (eluent 0.1 M NH$_4$HCO$_3$). Fractions containing product were combined and lyophilized to give the respective products 36, 38, 44, 46, 52 or 54 as white amorphous solids.

Addition of GlcNAc to compounds 36, 44 and 52 to form 37, 45 and 53:

A glycan (36, 44 or 52) and UDP-GlcNAc (1.5 eq) were dissolved in HEPES buffer (50 mM, pH 7.3), KCl (25 mM), MgCl$_2$ (2 mM) and DTT (1 mM). To this, CIAP (10 mU) and HP-39 (11 mU/μmol substrate) were added to achieve a final concentration of glycan ranging from 2-5 mM and incubated at 37° C. for 6 h. The reaction mixture was centrifuged and the supernatant subjected to gel filtration on Sephadex G-25 (eluent 0.1 M NH$_4$HCO$_3$). Fractions containing product were combined and lyophilized to give the respective products 37, 45 or 53 as white amorphous solids.

Mono-Sialylation(α2-6) of 38 to form 39:

Glycan 38 (500 ng, 170 nmoles) and CMP-Neu5Ac (220 ng, 340 nmoles) were dissolved in sodium cacodylate buffer (81.4 μL, 50 mM, pH 7.6) with BSA (0.1%). To this, CIAP (1.1 μL, 10 mU) and hST6Gal-I (1.6 μL, 9.4 mU/μmol substrate) were added and the resulting reaction mixture was incubated at 37° C. for 18H. The reaction mixture was centrifuged and the supernatant subjected to gel filtration on Sephadex G-25 (eluent 0.1 M NH$_4$HCO$_3$). Fractions containing product were combined and lyophilized to give 39 as a white amorphous solid.

Bis-Sialylation(α2-3) of 49 to form 50:

Glycan 49 (900 ng, 488 nmoles) and CMP-Neu5Ac (1.3 mg, 1.952 μmoles) were dissolved in sodium cacodylate buffer (90 μL, 50 mM, pH 7.6) with BSA (0.1%). To this, CIAP (1.3 μL, 10 mU) and rST3Gal-III (5.42 μL, 11 mU/μmol substrate) were added to achieve a concentration of glycan of 5 mM. The reaction mixture was incubated at 37° C. for 18 h. MALDI-TOF MS showed some starting material, and therefore additional CMP-Neu5Ac (0.5 mg), CIAP (1 μL) and rST3Gal-III (5 μL) were added and incubation was continued at 37° C. for another 18 h to achieve completion of the reaction. The reaction mixture was centrifuged and the supernatant subjected to gel filtration on Sephadex G-25 (eluent 0.1 M NH$_4$HCO$_3$). Fractions containing product were combined and lyophilized to give 50 as a white amorphous solid.

The preceding detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims. It is to be understood that the particular examples, materials, amounts, and procedures are to be interpreted broadly in accordance with the scope and spirit of the invention as set forth herein.

The complete disclosures of all patents, patent applications including provisional patent applications, and publications, and electronically available material (e.g., GenBank amino acid and nucleotide sequence submissions) cited herein are incorporated by reference. Additionally, this patent application incorporates by reference international patent publication WO2010/117803, entitled Heparan Sulfate Synthesis, published Oct. 14, 2010; U.S. Patent Publications 20090041836 A1, entitled "Glycopeptide and Uses Thereof," published Feb. 12, 2009 and 20090196916 A1, entitled "Liposome-Mediated Ligation," published Aug. 6, 2009; and International Patent Publications WO 2007/079448, entitled "Three Component Carbohydrate Vaccine," published Jul. 12, 2007; WO 2007/146070, entitled "Liposome-Mediated Native Chemical Ligation," published Dec. 21, 2007; and WO 2009/003944, entitled "Glycopeptide and Uses Thereof," published Jan. 7, 2010.

What is claimed is:

1. An orthogonally protected branched oligosaccharide having the formula (I):

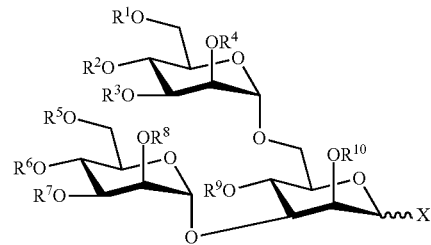

wherein each of $R^1$, $R^4$, $R^6$ and $R^8$ is independently an orthogonal protecting group or a permanent protecting group, provided that at least two of $R^1$, $R^4$, $R^6$ and $R^8$ are orthogonal protecting groups;

each of $R^2$, $R^3$, $R^5$, $R^7$, and $R^{10}$ is independently a permanent protecting group;

$R^9$ is an orthogonal protecting group, a permanent protecting group, or a glucosamine moiety;

X is —OR$^{15}$ or —SR$^{16}$;

$R^{15}$ is H, alkyl, cycloalkyl, substituted alkyl or cycloalkyl, alkenyl, substituted alkenyl, alkynyl, substituted alkynyl, aryl or substituted aryl; a protecting group; an anomeric spacer or linker; a fluorous tag; or a leaving group; and $R^{16}$ is H, alkyl, cycloalkyl, substituted alkyl or cycloalkyl, alkenyl, substituted alkenyl, alkynyl, substituted alkynyl, aryl, or substituted aryl.

2. The orthogonally protected oligosaccharide of claim 1 further comprising a glycosidically linked glucosamine moiety in place of X, wherein the ring hydroxyls on the glucosamine moiety are protected, wherein the amine at the C-2 position of the glucosamine moiety is protected, and wherein the anomeric position at the reducing end of the glucosamine moiety comprises X as in formula (I).

3. The orthogonally protected oligosaccharide of claim 1 further comprising a glycosidically linked glucosamine disaccharide in place of X, wherein the ring hydroxyls on the glucosamine disaccharide are protected, wherein the amines at both C-2 positions of the glucosamine disaccharide are protected, and wherein the anomeric position at the reducing end of the glucosamine disaccharide comprises X as in formula (I).

4. The orthogonally protected oligosaccharide of claim 2 comprising a glycosidically linked fucose moiety at position C-6 of the terminal reducing glucosamine.

5. The orthogonally protected oligosaccharide of claim 1 wherein the orthogonal protecting group is selected from the group consisting of levulinoyl (Lev); 9-fluorenylmethoxycarbonyl (Fmoc); allyloxycarbonyl (Alloc); 2-naphthylmethyl (Nap); 1-naphthylmethyl (1-Nap); benzoyl (Bz); difluorobenzoyl (dfBz); pivaloyl levulinoyl (PivLev); pivaloyl benzoyl (PivBz); para-methoxybenzyl ether (PMB); methoxy phenyl ether (MP); allyl ether (Allyl); chloroacetyl ester (ClAc); trichloroacetyl ester ($Cl_3Ac$), trifluoroacetyl ester ($F_3Ac$); and a silyl ether.

6. A method for making an oligosaccharide comprising:
deprotecting the orthogonally protected oligosaccharide of claim 1 by removing an orthogonal protecting group to yield a deprotected glycosyl acceptor; and
linking the deprotected glycosyl acceptor to a glycosyl donor to yield an extended oligosaccharide.

7. The method of claim 6 wherein the glycosyl donor is a protected or masked glucosamine or a lactosamine.

8. The method of claim 6 wherein the extended oligosaccharide comprises 4, 5, 6, 7, 8, 9, 10, 11, 12, 13 or 14 monosaccharide units.

9. The method of claim 6 wherein the extended oligosaccharide is a multi-antennary glycan comprising two, three, four or five branches.

10. The method of claim 6 comprising sequentially removing orthogonal protecting groups from the orthogonally protected oligosaccharide.

11. The method of claim 10 further comprising removing permanent protecting groups to yield a deprotected multi-antennary glycan.

12. The method of claim 11 wherein the multi-antennary glycan is asymmetric.

13. The method of claim 12 wherein the deprotected multi-antennary glycan is masked at at least one position.

14. The method of claim 12 further comprising contacting the asymmetric multi-antennary glycan with a first carbohydrate processing enzyme under conditions to yield an enzymatically extended multi-antennary glycan.

15. The method of claim 14 comprising unmasking the enzymatically extended multi-antennary glycan to yield an unmasked multi-antennary glycan, followed by contacting the unmasked multi-antennary glycan with a second carbohydrate processing enzyme under conditions to yield a multi-antennary glycan that is further extended.

16. The method of claim 15 further comprising sequentially contacting the extended multi-antennary glycan with at least one additional carbohydrate processing enzyme under conditions to further extend the multi-antennary glycan.

17. The orthogonally protected oligosaccharide of claim 3 comprising a glycosidically linked fucose moiety at position C-6 of the terminal reducing glucosamine.

* * * * *